United States Patent
Kwok et al.

(10) Patent No.: US 11,576,978 B2
(45) Date of Patent: Feb. 14, 2023

(54) HEMOGLOBIN-BASED THERAPEUTIC AGENTS

(71) Applicant: Cheer Global Limited, Hong Kong (CN)

(72) Inventors: Sui-Yi Kwok, Hong Kong (CN); Norman Fung-Man Wai, Vancouver (CA); Lan Zou, Hong Kong (CN)

(73) Assignee: Cheer Global Limited, Hong Kong (CN)

( * ) Notice: Subject to any disclaimer, the term of this patent is extended or adjusted under 35 U.S.C. 154(b) by 283 days.

(21) Appl. No.: 16/947,124

(22) Filed: Jul. 20, 2020

(65) Prior Publication Data

US 2021/0015935 A1    Jan. 21, 2021

Related U.S. Application Data

(60) Provisional application No. 62/876,005, filed on Jul. 19, 2019.

(51) Int. Cl.
| | |
|---|---|
| *A61K 47/64* | (2017.01) |
| *A61K 38/05* | (2006.01) |
| *A61K 38/12* | (2006.01) |
| *A61K 9/00* | (2006.01) |

(52) U.S. Cl.
CPC .......... *A61K 47/6445* (2017.08); *A61K 38/05* (2013.01); *A61K 38/12* (2013.01); *A61K 9/0019* (2013.01)

(58) Field of Classification Search
CPC ................................................ A61K 47/6445
See application file for complete search history.

(56) References Cited

U.S. PATENT DOCUMENTS 10,913,770 B2 * 2/2021 Kwok ...................... C07K 5/12

FOREIGN PATENT DOCUMENTS

| WO | 2014/186301 A1 | 11/2014 | |
|---|---|---|---|
| WO | WO-2014186301 A1 * | 11/2014 | ............. A61K 38/42 |
| WO | 2017/161288 A1 | 9/2017 | |

OTHER PUBLICATIONS

Bouchard et al. "Antibody-drug conjugates—A new wave of cancer drugs", Bioorganic and Medicinal Chemistry Letters, 2014, pp. 5357-5363 (Year: 2014).*
International Search Report and Written Opinion of PCT application No. PCT/CN2020/103092 issued from the International Search Authority dated Oct. 22, 2020.
Looker et al.; a Human Recombinant Haemoglobin Designed for Use as Blood Substitute; Nature; Mar. 19, 1992; vol. 356; pp. 258-260.
"GenPept: 1O1J_A," webpage https://www.ncbi.nlm.nih.gov/protein/1O1J_A, first retrieved on Jul. 2019.
"GenPept: 1O1J_B," webpage https://www.ncbi.nlm.nih.gov/protein/1O1J_B, first retrieved on Jul. 2019.

* cited by examiner

*Primary Examiner* — Lianko G Garyu
(74) *Attorney, Agent, or Firm* — S&F/WEHRW

(57) ABSTRACT

Provided herein are hemoglobin-based therapeutic agents useful for treating cancer, pharmaceutical composition including the same, and methods of use and preparation thereof.

19 Claims, 33 Drawing Sheets
(15 of 33 Drawing Sheet(s) Filed in Color)
Specification includes a Sequence Listing.

Hb-SMCC-DM1

Hb-EMCS-DM1

Hb-SMCC-DM4

Hb-EMCS-DM4

Hb-VcMMAE

| Cancer model | Liver cancer | | | |
|---|---|---|---|---|
| Cell line | Hep-55.1c | Hepa 1-6 | SK-HEP-1 | SMMC7721 |
| IC50 DM1 | 20.6 nM | 32.3 nM | 108.1 nM | 10.8 nM |
| IC50 Hb-SMCC-DM1 | 22.1 nM | 26.1 nM | 98.1 nM | 103.4 nM |
| Cancer model | Leukemia (AML) | | Acute lymphocytic leukemia | Pancreatic cancer |
| Cell line | HL-60 | C1498 | L1210 | Mia PaCa-2 |
| IC50 DM1 | 17.5 nM | 10.7 nM | 10.6 nM | 9.7 nM |
| IC50 Hb-SMCC-DM1 | 40.2 nM | 33.7 nM | 16.6 nM | 7.9 nM |
| Cancer model | Colon cancer | | | |
| Cell line | HCT116 | HT-29 | CT26 | Colo205 |
| IC50 DM1 | 7.6 nM | 10.5 nM | 10.7 nM | 6.9 nM |
| IC50 Hb-SMCC-DM1 | 62.8 nM | 56.7 nM | 14.4 nM | 85.7 nM |
| Cancer model | Lymphoma NK | | Melanoma | Breast cancer |
| Cell line | KAI-3 | KHYG-1 | B16-F10 | 4T1 |
| IC50 DM1 | 25.4 nM | 22.3 nM | 2.3 nM | 68.8 nM |
| IC50 Hb-SMCC-DM1 | 442.2 nM | 17.6 nM | 6.9 nM | 145.2 nM |

FIG. 5A

| Cell line | *MIA PaCa-2* | *HCT116* |
|---|---|---|
| Hb-SMCC-DM1 | 7.9 nM | 62.80 nM |
| Hb-SMCC-DM4 | 2.48 nM | 2.33 nM |
| Hb-EMCS-DM1 | 27.2 nM | 89.12 nM |
| Hb-EMCS-DM4 | 1.09 nM | 7.89 nM |

FIG. 5B

| Cancer model | Liver cancer | | | Pancreatic cancer | Colon cancer | |
|---|---|---|---|---|---|---|
| Cell line | Hep-55.1c | Hepa 1-6 | SK-HEP-1 | Mia PaCa-2 | HCT116 | HT-29 |
| IC50 (nM) DM1 | 20.6 | 32.3 | 108.7 | 4.1 | 8.6 | 30.4 |
| Hb-SMCC-DM1 (MDR 1.1) | 194.5 | 170.8 | 1005.4 | 97.9 | 180.1 | 157.0 |
| Hb-SMCC-DM1 (MDR 1.7) | 67.4 | 102.6 | 499.9 | 41.2 | 56.1 | 52.4 |
| Hb-SMCC-DM1 (MDR 2.1) | 50.5 | 49.3 | 151.0 | 21.9 | 33.1 | 42.5 |
| Hb-SMCC-DM1 (MDR 3.0) | 22.1 | 26.1 | 98.8 | 12.7 | 23.4 | 26.1 |

Left: null; Middle: Hb-AF750; Right: Hb-SMCC-DM1-AF750

Various kinds of organs were collected at 72hr of drug administration.

| Hb concentration (mg/ml) | Linker | Linker (equiv.) | Reaction time (h) | Conversion (%) | MDR of linker | Hb-linker concentration (mg/ml) | Drug | Drug (equiv.) | Solvent | Reaction time (h) | Conversion (%) | MDR of drug |
|---|---|---|---|---|---|---|---|---|---|---|---|---|
| 100 | SMCC | 10 | 0.5 | 100 | 12 | NA | NA | NA | NA | NA | NA | NA |
| 100 | SMCC | 10 | 1 | 100 | 13 | NA | NA | NA | NA | NA | NA | NA |
| 100 | SMCC | 10 | 1.5 | 100 | 8.3 | 10 | DM1 | 4 | DMSO | 1 | 100 | 1 |
| 100 | SMCC | 10 | 1.5 | 100 | 8.3 | 10 | DM1 | 4 | DMSO | 2 | 100 | 1.4 |
| 100 | SMCC | 10 | 1.5 | 100 | 8.3 | 10 | DM1 | 4 | DMSO | 20 | 100 | 1.4 |
| 100 | EMCS | 10 | 0.5 | 100 | 1.9 | NA | NA | NA | NA | NA | NA | NA |
| 100 | EMCS | 10 | 1 | 100 | 2 | NA | NA | NA | NA | NA | NA | NA |
| 100 | EMCS | 10 | 1.5 | 100 | 8 | 10 | DM1 | 4 | DMSO | 1 | 72 | 1.2 |
| 100 | EMCS | 10 | 1.5 | 100 | 6 | 10 | DM1 | 4 | DMSO | 2 | 78 | 1.4 |
| 100 | EMCS | 10 | 1.5 | 100 | 6 | 10 | DM1 | 4 | DMSO | 20 | 77 | 1.4 |
| 100 | SMCC | 10 | 1.5 | 100 | 8.3 | 10 | DM4 | 4 | DMSO | 2 | 100 | 2.2 |
| 100 | SMCC | 10 | 1.5 | 100 | 8.3 | 10 | DM4 | 4 | DMSO | 4 | 100 | 2.8 |
| 100 | SMCC | 10 | 1.5 | 100 | 8.3 | 10 | DM4 | 4 | DMSO | 20 | 100 | 3.4 |
| 100 | EMCS | 10 | 1.5 | 100 | 6 | 10 | DM4 | 4 | DMSO | 2 | 80 | 2 |
| 100 | EMCS | 10 | 1.5 | 100 | 6 | 10 | DM4 | 4 | DMSO | 4 | 41 | 1.4 |
| 100 | EMCS | 10 | 1.5 | 100 | 6 | 10 | DM4 | 4 | DMSO | 20 | 54 | 1.4 |

FIG. 12

| Hb concentration (mg/ml) | Drug | Drug (equiv.) | Solvent | Reaction time (h) | Conversion (%) | MDR of drug |
|---|---|---|---|---|---|---|
| 100 | SMCC-DM1 | 6 | DMSO | 16 | 15 | 3 |
| 50 | SMCC-DM1 | 8 | DMSO | 16 | 20 | 3 |
| 50 | SMCC-DM1 | 10 | DMSO | 16 | 20 | 3.4 |
| 50 | SMCC-DM1 | 15 | DMSO | 16 | 36 | 3.5 |
| 50 | SMCC-DM1 | 20 | DMSO | 16 | 32 | 3.5 |
| 2.5 | SMCC-DM1 | 8 | DMSO | 16 | 31 | 3.2 |
| 5 | SMCC-DM1 | 8 | DMSO | 16 | 30 | 3.2 |
| 10 | SMCC-DM1 | 8 | DMSO | 16 | 28 | 3.3 |
| 20 | SMCC-DM1 | 8 | DMSO | 16 | 24 | 3.4 |
| 25 | SMCC-DM1 | 8 | DMSO | 16 | 28 | 3.4 |
| 2.5 | SMCC-DM1 | 15 | DMSO | 16 | 30 | 3.1 |
| 5 | SMCC-DM1 | 15 | DMSO | 16 | 30 | 3.2 |
| 10 | SMCC-DM1 | 15 | DMSO | 16 | 28 | 3.3 |
| 20 | SMCC-DM1 | 15 | DMSO | 16 | 24 | 3.5 |
| 25 | SMCC-DM1 | 15 | DMSO | 16 | 27 | 3.4 |
| 10 | SMCC-DM1 | 4 | DMSO | 20 | 29 | 3.2 |
| 10 | SMCC-DM1 | 6 | DMSO | 20 | 23 | 3.1 |
| 10 | SMCC-DM1 | 8 | DMSO | 20 | 24 | 3.2 |
| 10 | SMCC-DM1 | 4 | DMA | 20 | 22 | 3.1 |
| 10 | SMCC-DM1 | 6 | DMA | 20 | 28 | 3.2 |
| 10 | SMCC-DM1 | 8 | DMA | 20 | 30 | 3.2 |
| 4 | SMCC-DM1 | 5 | DMSO | 20 | 32 | 0.8 |
| 4 | SMCC-DM1 | 10 | DMSO | 20 | 38 | 1 |
| 4 | SMCC-DM1 | 20 | DMSO | 20 | 42 | 1.2 |
| 5 | SMCC-DM1 | 2 | DMSO | 20 | 68 | 2.2 |
| 5 | SMCC-DM1 | 5 | DMSO | 20 | 87 | 4.6 |

FIG. 13

| Hb concentration (mg/ml) | Drug | Drug (equiv) | Solvent | Reaction time (h) | Reaction temperature | Conversion (%) | MDR of drug |
|---|---|---|---|---|---|---|---|
| 100 | VcMMAE | 2 | DMSO | 16 | 4°C | 0 | NA |
| 100 | VcMMAE | 4 | DMSO | 16 | 4°C | 0 | NA |
| 50 | VcMMAE | 6 | DMSO | 16 | 4°C | 0 | NA |
| 50 | VcMMAE | 8 | DMSO | 16 | 4°C | 11 | 1 |
| 2.5 | VcMMAE | 8 | DMSO | 16 | 4°C | 31 | 12 |
| 5 | VcMMAE | 8 | DMSO | 16 | 4°C | 44 | 13 |
| 10 | VcMMAE | 8 | DMSO | 16 | 4°C | 42 | 14 |
| 20 | VcMMAE | 8 | DMSO | 16 | 4°C | 42 | 15 |
| 25 | VcMMAE | 8 | DMSO | 16 | 4°C | 41 | 13 |
| 2.5 | VcMMAE | 4 | DMSO | 16 | 4°C | 14 | 1 |
| 5 | VcMMAE | 4 | DMSO | 16 | 4°C | 35 | 12 |
| 10 | VcMMAE | 4 | DMSO | 16 | 4°C | 45 | 14 |
| 20 | VcMMAE | 4 | DMSO | 16 | 4°C | 39 | 14 |
| 25 | VcMMAE | 4 | DMSO | 16 | 4°C | 32 | 12 |
| 10 | VcMMAE | 2 | DMSO | 20 | 4°C | 0 | 0 |
| 10 | VcMMAE | 4 | DMSO | 20 | 4°C | 12 | 1 |
| 10 | VcMMAE | 2 | DMSO | 20 | RT | 30 | 12 |
| 10 | VcMMAE | 4 | DMSO | 20 | RT | 47 | 14 |
| 10 | VcMMAE | 2 | DMA | 20 | 4°C | 0 | 0 |
| 10 | VcMMAE | 4 | DMA | 20 | 4°C | 22 | 11 |
| 10 | VcMMAE | 2 | DMA | 20 | RT | 0 | 0 |
| 10 | VcMMAE | 4 | DMA | 20 | RT | 51 | 13 |

FIG. 14

Di-alpha chain (SEQ ID NO: 1) (TBM1)

MLSPADKTNVKAAWGKVGAHAGEYGAEAFERMFLSFPTTKTYFPHFDLSHGSAQVKGQGK
KVADALTNAVAHVDDMPNALSALSDLHAHKLRVDPVNFKLLSHCLLVTLAAHLPAEFTPA
VHASLDKFLASVSTVLTSKYRGMLSPADKTNVKAAWGKVGAHAGEYGAEAFERMFLSFPT
TKTYFPHFDLSHGSAQVKGQGKKVADALTNAVAHVDDMPNALSALSDLHAHKLRVDPVNF
KLLSHCLLVTLAAHLPAEFTPAVHASLDKFLASVSTVLTSKYR

Beta chain (SEQ ID NO: 2) (TBM1)

MHLTPEEKSAVTALWGKVNVDEVGGEALGRLLVVYPWTQRFFESFGDLSTPDAVMGNPKV
KAHGKKVLGAFSDGLAHLDNLKGTFATLSELHCDKLHVDPENFRLLGNVLVCVLAHHFGK
EFTPPVQAAYQKVVAGVANALAHKYH

FIG. 15

HEMOGLOBIN-BASED THERAPEUTIC AGENTS

CROSS-REFERENCE TO RELATED APPLICATIONS

This application claims the benefit of priority of U.S. Provisional Application No. 62/876,005, filed on Jul. 19, 2019, the contents of which being hereby incorporated by reference in their entirety for all purposes.

REFERENCE TO SEQUENCE LISTING

The specification further incorporates by reference the Substitute Sequence Listing submitted herewith via EFS-Web on Aug. 12, 2020. The Substitute Sequence Listing text file, identified as Sequence_Listing_034615-000005.txt, is 4,183 bytes and was created on Jul. 20, 2020. The Substitute Sequence Listing, electronically filed herewith, is identical to the PDF copy of the Sequence Listing filed Jul. 20, 2020 and thus does not contain new matter.

TECHNICAL FIELD

The present disclosure relates to hemoglobin-based therapeutic agents useful in the treatment of cancer, pharmaceutical compositions, and methods of use and preparation thereof.

BACKGROUND

Chemotherapy is the use of anticancer drugs to treat cancerous cells. Chemotherapy has been used for many years and is one of the most common treatments for cancer. In most cases, chemotherapy works by interfering with the cancer cell's ability to grow or reproduce. Different groups of drugs work in different ways to fight cancer cells. Chemotherapy may be used alone for some types of cancer or in combination with other treatments such as radiation (or radiotherapy) or surgery. Often, a combination of chemotherapy drugs is used to fight a specific cancer. There are over 50 chemotherapy drugs that are commonly used.

Besides the traditional chemotherapy drugs, a class of cytotoxic agents, such as the maytansinoids (e.g. mertansine (DM1) and ravtansine (DM4)), the auristatins (e.g monomethylauristatin E (MMAE) and monomethylauristain F (MMAF)), and the calicheamicins (e.g calicheamicin γ), are several orders of magnitude more potent than clinically used anticancer drugs. However, due to their poor selectivity for tumors, their clinical use in cancer therapy has been greatly limited by their severe systemic side-effects. Clinical trials with maytansine have been discontinued due to serious adverse effects on the central nervous system and gastrointestinal system. Therefore, there is a need for methods for improving the selectivity of these cytotoxic agents, alleviating the side effects, while maintaining their efficacy during cancer treatment.

Hypoxia is common in cancers. Hypoxia and anemia (which contributes to tumor hypoxia) can lead to ionizing radiation and chemotherapy resistance by depriving tumor cells of the oxygen essential for the cytotoxic activities of these agents. Hypoxia may also reduce tumor sensitivity to radiation therapy and chemotherapy through one or more indirect mechanisms that include proteomic and genomic changes.

Thus, there is a need in the art for improved cancer treatments that target cancerous cells and tissues while reducing the effects of such cancer treatments on non-cancerous cells and tissues.

SUMMARY

Provided herein are hemoglobin-based therapeutic agents that are capable of selectively targeting cancer cells in order to efficiently kill cancer cells by a chemotherapeutic agent, such as maytansinoids (e.g. mertansine (DM1) and ravtansine (DM4)), the auristatins (e.g monomethylauristatin E (MMAE) and monomethylauristain F (MMAF)), and the calicheamicins (e.g calicheamicin γ). These chemotherapeutic agents are several orders of magnitude more potent than clinically used anticancer drugs making them highly cytotoxic. However, due to their poor selectivity for tumors, their clinical use in cancer therapy has been greatly limited by their severe systemic side-effects. These problems may be overcome by linking the chemotherapeutic agents to hemoglobin. When compared to the unmodified chemotherapeutic agent, the hemoglobin-based therapeutic agents of the present disclosure not only can target cancer cells, but can be much more efficacious in the treatment of tumors. Further, since the cancer-targeting hemoglobin-based therapeutic agents are more selective, the adverse side effects from the therapeutic drug can be greatly decreased.

Provided herein is a hemoglobin-based therapeutic agent comprising a hemoglobin and a chemotherapeutic agent selected from the group consisting of maytansinoid, an auristatin, and a calicheamicin, wherein the chemotherapeutic agent is covalently attached to the hemoglobin via a linker.

In a first embodiment of the first aspect, provided herein is the hemoglobin-based therapeutic agent of the first aspect, wherein the hemoglobin is selected from the group consisting of bovine hemoglobin, human hemoglobin, canine hemoglobin, porcine hemoglobin, equine hemoglobin and recombinant hemoglobin or a subunit thereof.

In a second embodiment of the first aspect, provided herein is the hemoglobin-based therapeutic agent of the first aspect, wherein the hemoglobin comprises a di-alpha chain and two beta chains, wherein the di-alpha chain comprises a polypeptide sequence having at least 98.93% sequence homology with SEQ ID NO: 1, wherein the amino acids at position 1 and position 143 of SEQ ID NO: 1 must be methionine, the amino acids at position 29 and position 171 of SEQ ID NO: 1 must be phenylalanine, and the amino acids at position 58 and position 200 of SEQ ID NO: 1 must be glutamine; and the each of the two beta chains comprises a polypeptide sequence having at least 97.94% sequence homology with SEQ ID NO: 2, wherein the amino acid at position 1 must be methionine In a third embodiment of the first aspect, provided herein is the hemoglobin-based therapeutic agent of the first aspect, wherein the molar drug ratio (MDR) of the hemoglobin-based therapeutic agent is between 1.0-5.0.

In a fourth embodiment of the first aspect, provided herein is the hemoglobin-based therapeutic agent of the first aspect, wherein the chemotherapeutic agent is selected from the group consisting of mertansine (DM1), ravtansine (DM4), and monomethylauristatin E (MMAE).

In a fifth embodiment of the first aspect, provided herein is the hemoglobin-based therapeutic agent of the first aspect, wherein the linker has the Formula 1:

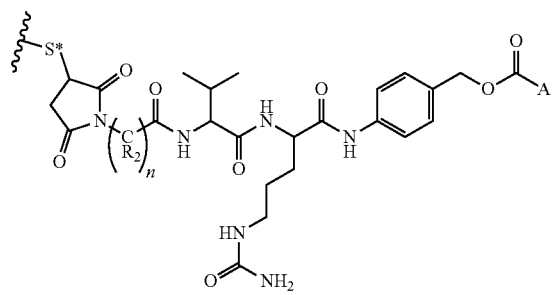

1 wherein A is the chemotherapeutic agent;

N* represents a nitrogen in a lysine side chain in the hemoglobin or a N-terminal amine in the hemoglobin;

n is a whole number selected from 1-10; and each R is hydrogen; or two R taken together with the carbons to which they are attached form a 3-7 membered cycloalkane and each remaining R is hydrogen; or the linker has the Formula 2:

2 wherein A is the chemotherapeutic;

N* represents a nitrogen in a lysine side chain in the hemoglobin or a N-terminal amine in the hemoglobin;

S* represents a sulfur in a cysteine side chain in the hemoglobin;

n is a whole number selected from 1-10; and each R is hydrogen; or two R taken together with the carbons to which they are attached form a 3-7 membered cycloalkane and each remaining R is hydrogen.

In a sixth embodiment of the first aspect, provided herein is the hemoglobin-based therapeutic agent of the fifth embodiment of the first aspect, wherein n is a whole number between 2-6 and each R is hydrogen; or n is a whole number between 4-6; two R taken together with the carbons to which they are attached form a 4-6 membered cycloalkane and each remaining R is hydrogen.

In a seventh embodiment of the first aspect, provided herein is the hemoglobin-based therapeutic agent of the first aspect, wherein the hemoglobin-based therapeutic agent is selected from the group consisting of:

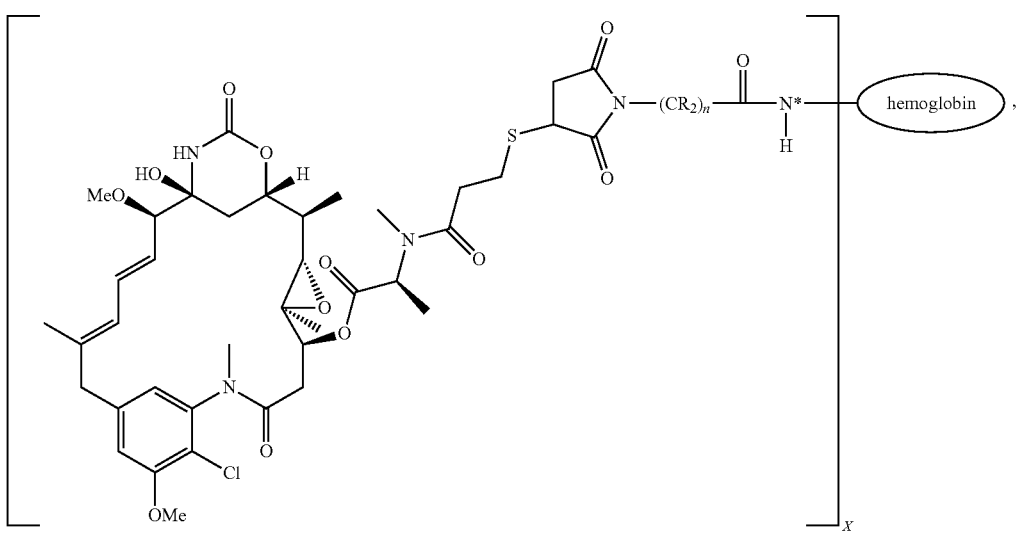

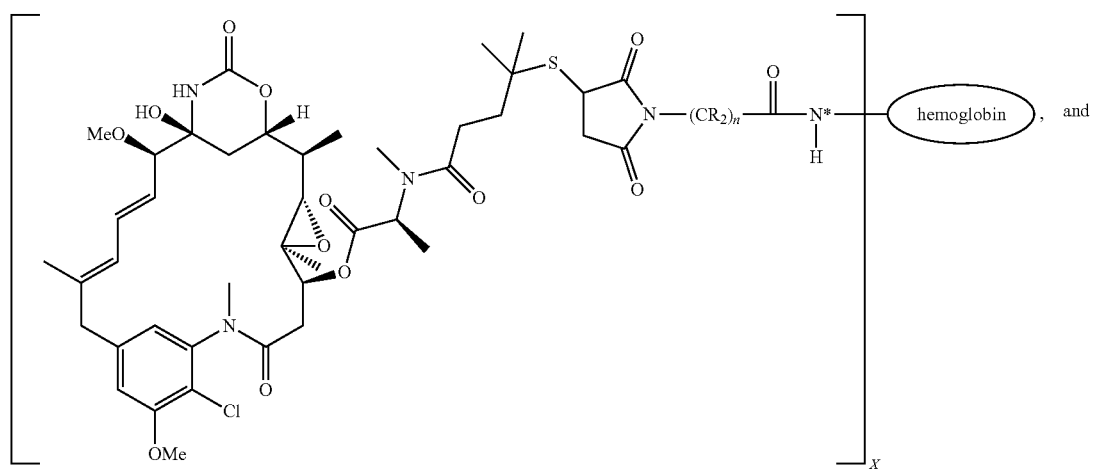

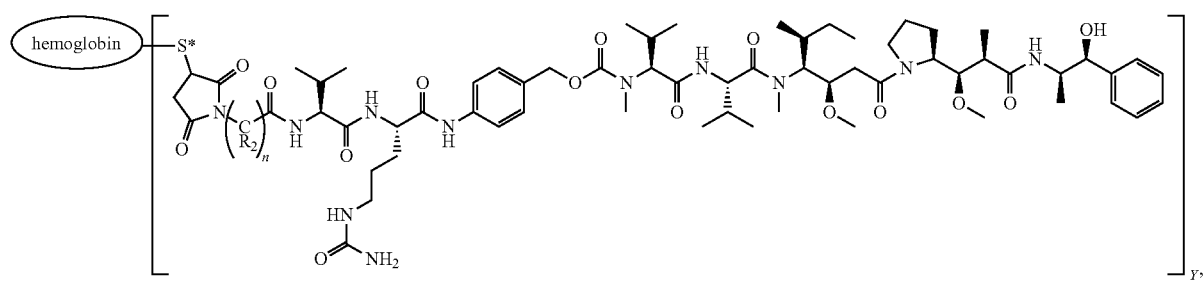

wherein each N* independently represents a nitrogen in a lysine side chain in the hemoglobin or a N-terminal amine in the hemoglobin;

each S* independently represents a sulfur in a cysteine side chain in the hemoglobin;

n is a whole number between 1-10;

each R is hydrogen; or two R taken together with the carbons to which they are attached form a 3-7 membered cycloalkane and each remaining R is hydrogen;

X is the MDR of the hemoglobin-based therapeutic agent, wherein X has a value between 1.0-5.0; and Y is the MDR of the hemoglobin-based therapeutic agent, wherein Y has a value between 1.0-2.0.

In an eighth embodiment of the first aspect, provided herein is the hemoglobin-based therapeutic agent of the first aspect, wherein the hemoglobin-based therapeutic agent is selected from the group consisting of:

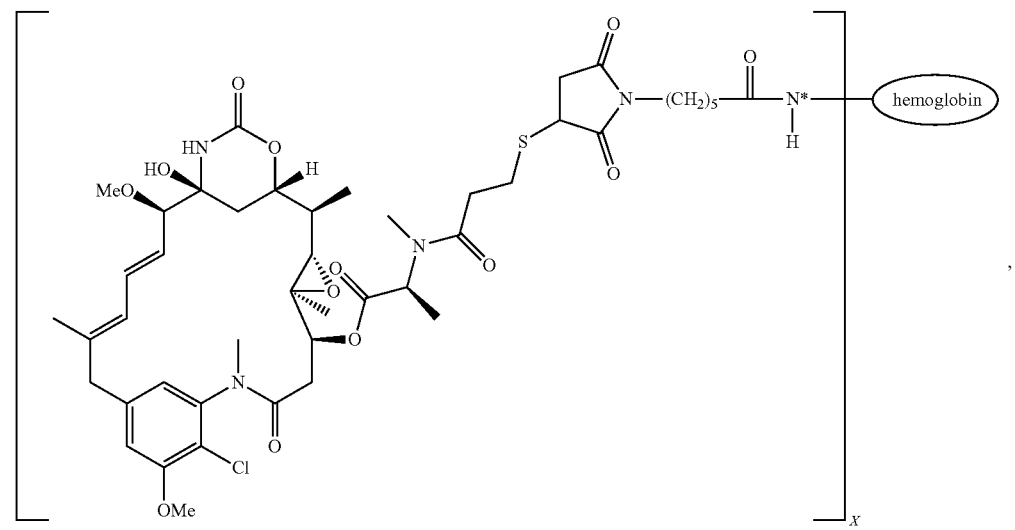

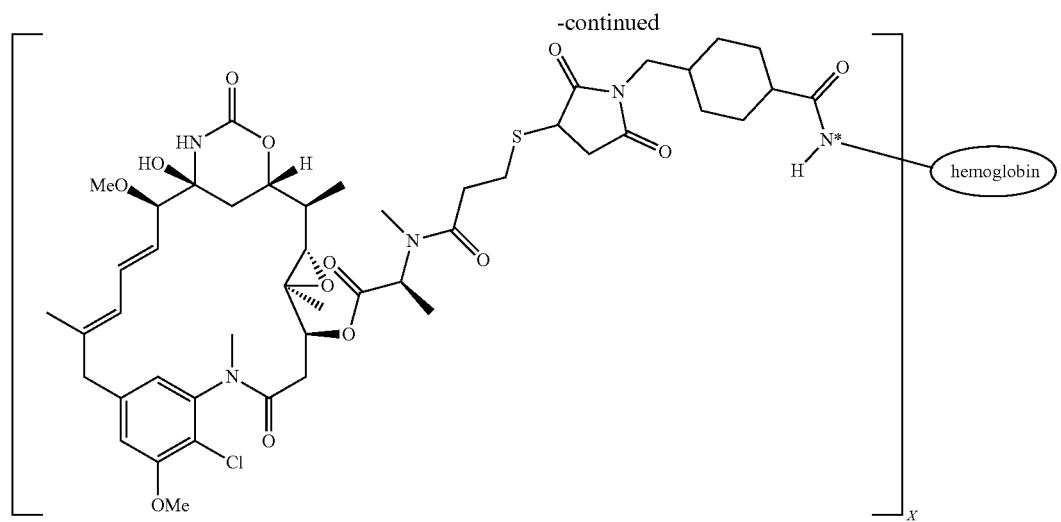
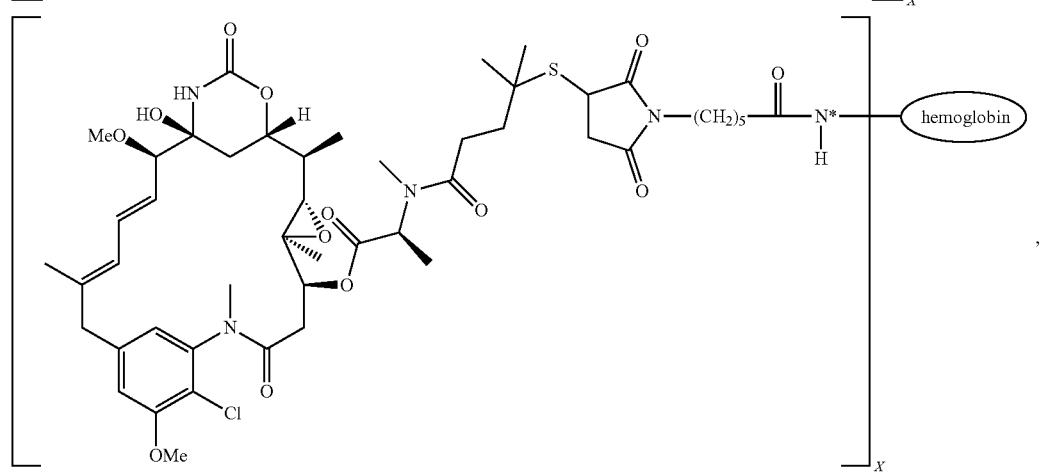
, and
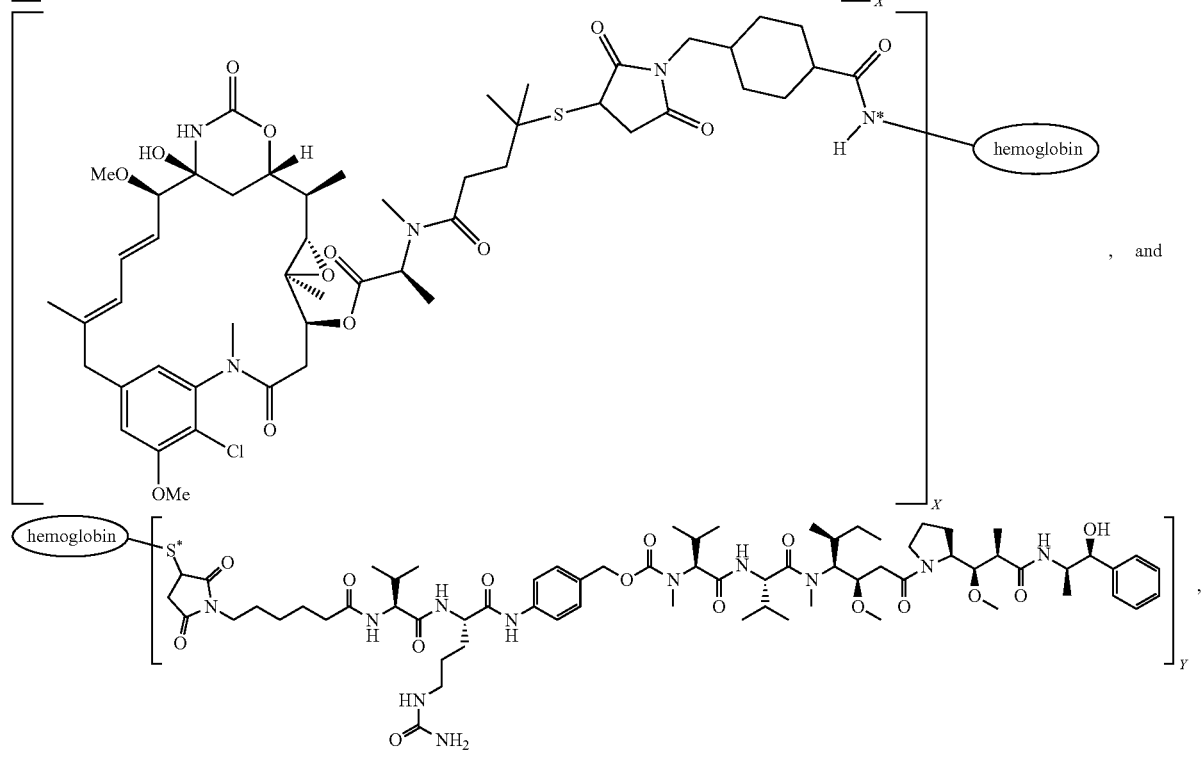

wherein each N* independently represents a nitrogen in a lysine side chain in the hemoglobin or a N-terminal amine in the hemoglobin;

each S* independently represents a sulfur in a cysteine side chain in the hemoglobin;

X is the MDR of the hemoglobin-based therapeutic agent, wherein X has a value between 1.0-5.0; and Y is the MDR of the hemoglobin-based therapeutic agent, wherein Y has a value between 1.0-2.0.

In a ninth embodiment of the first aspect, provided herein is the hemoglobin-based therapeutic agent of the first aspect, wherein the hemoglobin-based therapeutic agent has the formula:

wherein A is DM1 or DM4;

X is the MDR of the hemoglobin-based therapeutic agent, wherein X has a value between 1.0-5.0;

each N* independently represents a nitrogen in a lysine side chain in the hemoglobin or a N-terminal amine in the hemoglobin;

n is a whole number selected from 1-10; and each R is hydrogen; or two R taken together with the carbons to which they are attached form a 3-7 membered cycloalkane and each remaining R is hydrogen, the method comprising:

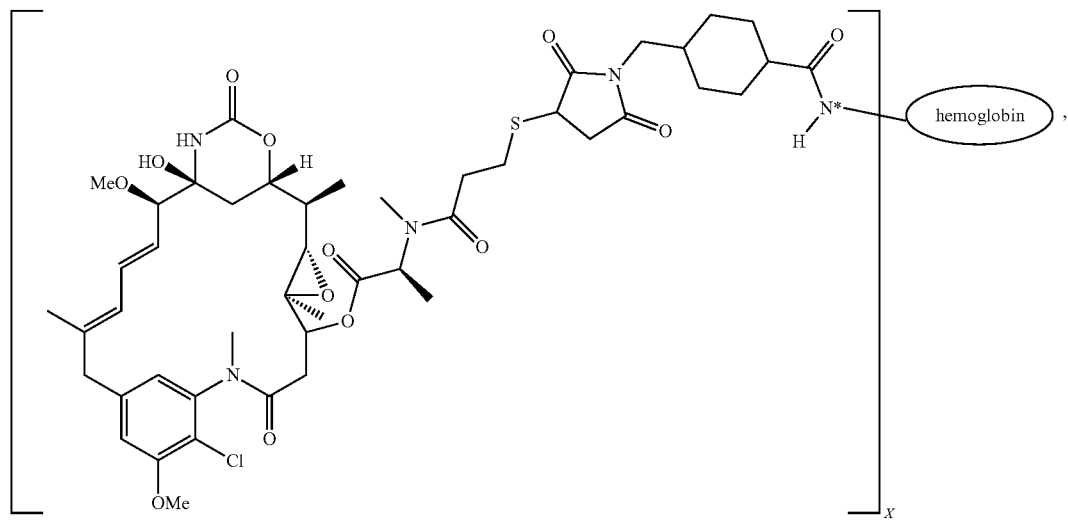

wherein each N* independently represents a nitrogen in a lysine side chain in the hemoglobin or a N-terminal amine in the hemoglobin; and X is the MDR of the hemoglobin-based therapeutic agent, wherein X has a value between 1.0-5.0.

In a tenth embodiment of the first aspect, provided herein is the hemoglobin-based therapeutic agent of the ninth embodiment of the first aspect, wherein X has a value between 2.5-3.5.

In a eleventh embodiment of the first aspect, provided herein is the hemoglobin-based therapeutic agent of the first aspect further comprising a fluorescent dye.

In a second aspect, provided herein is a method for preparing a hemoglobin-based therapeutic agent of Formula 3:

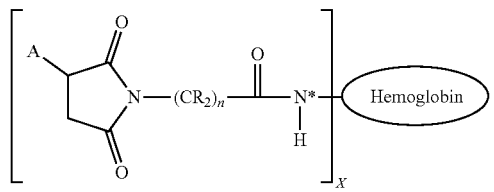

contacting a hemoglobin with a compound of Formula 4:

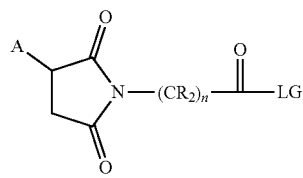

wherein LG is a leaving group, thereby forming the hemoglobin-based therapeutic agent of Formula 3.

In a first embodiment of the second aspect, provided herein is the method of the second aspect, wherein the molar ratio of hemoglobin to the compound of Formula 4 is between 1:4 to 1:6.

In a second embodiment of the second aspect, provided herein is the method of the second aspect, wherein the compound of Formula 4 has the structure:

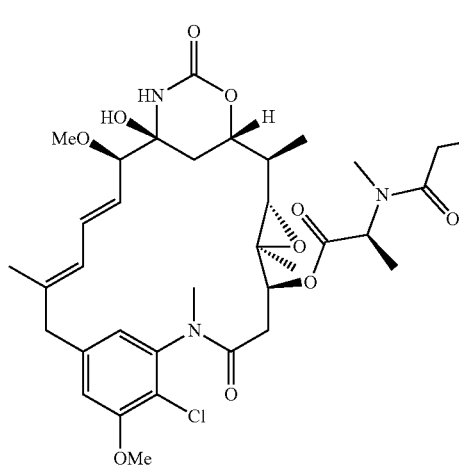
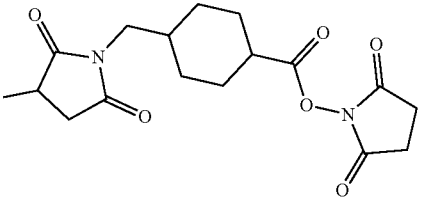

In a third aspect, provided herein is a pharmaceutical composition comprising a hemoglobin-based therapeutic agent of the first aspect and at least one pharmaceutically acceptable carrier.

In a fourth aspect, provided herein is a method of treating cancer in a subject in need thereof, the method comprising administering a therapeutically effective amount of a hemoglobin-based therapeutic agent of the first aspect to the subject.

In a first embodiment of the fourth aspect, provided herein is the method of the fourth aspect, wherein the cancer is selected from the group consisting of pancreatic cancer, leukemia, head and neck cancer, colorectal cancer, lung cancer, breast cancer, liver cancer, nasopharyngeal cancer, esophageal cancer, lymphoma, melanoma, and brain cancer.

In a second embodiment of the fourth aspect, provided herein is the method of the fourth aspect, wherein said cancer is hepatocellular carcinoma, liver cancer progenitor cells-induced tumor, glioblastoma, or triple negative progenitor cells-induced tumor.

In a third embodiment of the fourth aspect, provided herein is the method of the fourth aspect, wherein the hemoglobin-based therapeutic agent is administered intravenously, intraperitoneally, or subcutaneously.

The hemoglobin-based therapeutic agents described herein can also be linked to fluorescent probe(s) to facilitate the live-cell imaging and diagnostic imaging. Namely, the hemoglobin-based therapeutic agent conjugated with fluorescein can be uptaken into, e.g., colon cancer cells, liver cancer cells and breast cancer cells. The uptake of freshly fluorescein conjugated hemoglobin-based therapeutic agent by cells is verified by immediately employing the same to the cells in a series of live cell uptake studies as described hereinafter. The fluorescein conjugated hemoglobin-based therapeutic agent is observed to be uptaken into liver cancer cells (e.g. SMMC7721 cell line), colon cancer cells (e.g. HCT116) and breast cancer cells (e.g. 4T1) after 45 min of exposure.

The hemoglobin-based therapeutic agents described herein can also be linked to fluorescent probe(s) to facilitate live animal imaging. For example, when the hemoglobin-based therapeutic agents described herein are conjugated with Alexa Fluor 750 and intravenously injected into live mice, the fluorescent signal of the hemoglobin-based therapeutic agent conjugated with Alexa Fluor 750 can be observed after 2 h of exposure.

Therefore, the first aspect of the present disclosure is to chemically link the modified hemoglobin or crosslinked hemoglobin to a chemotherapeutic agent via a (e.g., non-cleavable) linker in order to kill the cancer cells. The therapeutic drug or active agent which can be linked to the hemoglobin molecule includes, but not limited to, chemotherapeutic agents, such as DM1, DM4, MMAE, or any other therapeutic drug or compound, which is proven to be effective for treating or alleviating cancer and capable of being readily linked to a hemoglobin molecule, through said linker to the crosslinked hemoglobin molecule or with the chemically modified hemoglobin molecule. Besides linking to therapeutic drug, the hemoglobin molecule can also be linked to cell or fluorescent labeling agent including but not limited to fluorescent proteins, non-protein organic fluorophores, fluorescent nano-particles and metal-based luminescent dye.

The therapeutic premise of hemoglobin-base therapeutic agents based on the hypothesis that target delivery of potent cytotoxic drugs to tumors will provide better tolerability and efficacy compared with non-targeted delivery, where poor tolerability can limit efficacious doses.

Preliminary toxicity studies in normal mice are present for hemoglobin-base therapeutic agents, including limited assessment of unconjugated cytotoxic drugs. Hemoglobin-based therapeutic agents described herein are well tolerated at doses up to two-fold higher of unconjugated cytotoxic drugs, supporting the premise that the hemoglobin-base therapeutic agents described herein can have improved therapeutic efficacy and decrease the toxicity.

Preliminary efficacy studies of tumor growth are present for hemoglobin-based therapeutic agents, including colorectal cancer HCT116 xenograft nude mice model, liver cancer Hep-55.1c xenograft C57 mice model, and pancreatic cancer Mia PaCa-2 xenograft nude mice model, etc. Hemoglobin-based therapeutic agents described herein can inhibit the tumor growth in these cancer models well, up to 78% inhibition of the tumor size in pancreatic cancer Mia PaCa-2 xenograft nude mice model, indicating the premise that the hemoglobin-based therapeutic agents described herein can suppress the tumor growth and have anticancer efficacy.

The present disclosure further relates to pharmaceutical compositions comprising the hemoglobin-based therapeutic agents described herein for targeted cancer treatment in humans and other animals. The pharmaceutical compositions comprise a hemoglobin-based therapeutic agent described herein and at least one of a pharmaceutically acceptable carrier, salt, buffer, water, or a combination thereof. The third aspect of the present disclosure provides a method of using pharmaceutical composition described herein for treating cancer by administering said composition to a subject in need thereof suffering from cancer. Said pharmaceutical composition can be administered to the subject by various routes including, but not limited to, intravenous injection, intraperitoneal injection, and subcutaneous injections.

Hemoglobin from different sources is a protein that targets to cancer cells. This targeting property facilitates killing cancerous cells, cancer stem cells and/or cancer progenitor cells efficiently. As such, selectivity of the conjugated cytotoxic agent can be improved.

The hemoglobin-based therapeutic agents described herein can be used in the treatment of various cancers, such as pancreatic cancer, leukemia, head and neck cancer, colorectal cancer, lung cancer, breast cancer, liver cancer, nasopharyngeal cancer, esophageal cancer, lymphoma, melanoma, and brain cancer. The present disclosure also provides hemoglobin-based therapeutic agents, methods of treating cancer, and to methods of treating and/or inhibiting metastasis of cancerous tissue and recurrence of cancerous tissue, including but not limited to liver cancer (which can be exemplified in liver cancer progenitor cells-induced tumor xenograft model), breast cancer, especially triple negative breast cancer (which can be exemplified in triple negative progenitor cells-induced tumor xenograft model). Cells within a tumor are heterogeneous in nature. It is generally thought to be made up of (1) a majority of cancer cells with limited ability to divide, and (2) a rare population of cancer stem-like cells (CSCs), also known as progenitor cells, which can form new tumor cells and are highly metastatic in nature. Due to their inherent properties of being chemoresistant and metastatic, CSCs have been postulated to be responsible for recurrence in cancer patients. The tumor progenitor cells-induced mice models as described herein are considered to be the most representative model of tumor metastasis and recurrence.

As the hemoglobin moiety is also capable of binding to and delivering oxygen to kill cancer stem cells while the conjugated cytotoxic agent moiety can kill the cancer cells, the hemoglobin-based therapeutic agents described herein is to give a synergistic effect in cancer treatment.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects and features of the present disclosure will become apparent from the following description of the disclosure, when taken in conjunction with the accompanying drawings.

FIG. 5A shows the efficacy (Cytotoxicity) of hemoglobin-based cytotoxic agents in liver cancer cell lines, leukemia (AML) cell lines, acute lymphocytic leukemia cell lines, pancreatic cancer cell lines, colon cancer cell lines, lymphoma NK cell lines, melanoma cell lines, and breast cancer cell lines in vitro. The Hb-SMCC-DM1 tested in the SMMC7721, HCT116, and HT-29 cell lines had an MDR 4.6. The Hb-SMCC-DM1 tested in all other cell lines had an MDR of 3.0.

FIG. 5B shows the efficacy (Cytotoxicity) of hemoglobin-based cytotoxic agents with different linkers (succinimidyl 4-(N-maleimidomethyl)cyclohexane-1-carboxylate (SMCC) and N-ε-malemidocaproyl-oxysuccinimide ester (EMCS)) and different cytotoxic agents (DM1 and DM4) in pancreatic cancer cell lines Mia PaCa-2 and colon cancer cell line HCT116 in vitro.

FIG. 12 shows the conversion and MDR of Hb-SMCC-DM1, Hb-EMCS-DM1, Hb-SMCC-DM4, and Hb-EMCS-DM4 under different conditions by two-step method.

FIG. 13 shows the conversion and MDR of Hb-SMCC-DM1 under different conditions by one-step method.

FIG. 14 shows the conversion and MDR of Hb-VcMMAE under different conditions by one-step method.

FIG. 15 shows the polypeptide sequences for di-alpha chain SEQ ID NO: 1 and beta chain SEQ ID NO: 2 according to certain embodiments described herein.

DETAILED DESCRIPTION

Definitions

Figure 1:
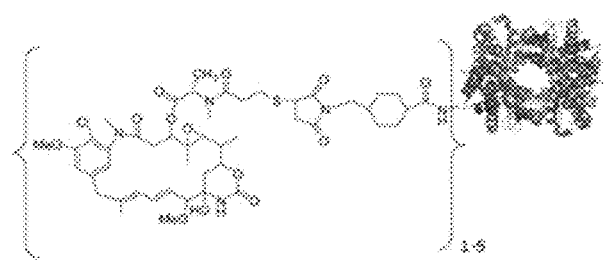
FIG. 1 shows a design approach for construction of hemoglobin-based cytotoxic agents in accordance with certain embodiments described herein. One or more cytotoxic agents can be linked to modified hemoglobin to form the hemoglobin-based therapeutic agent.
Figure 1:
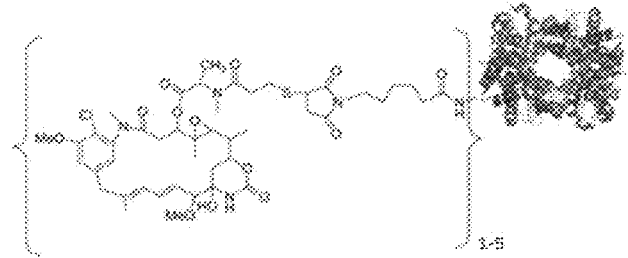
Figure 1:
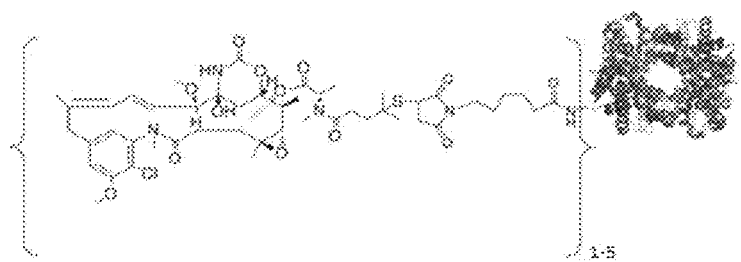
Figure 1:
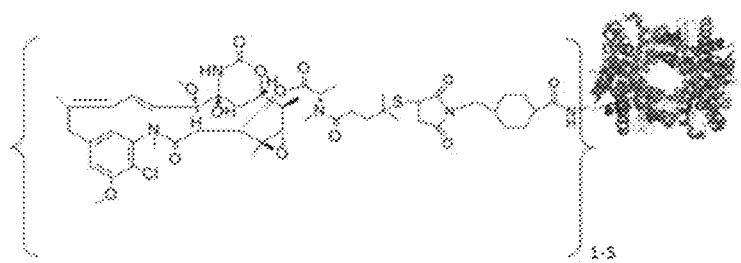
Figure 1:
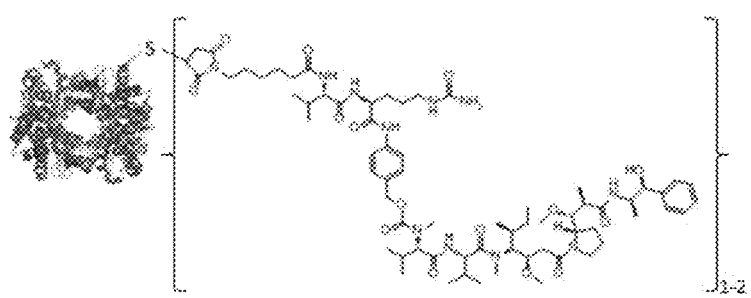

The following terms shall be used to describe the present invention. In the absence of a specific definition set forth herein, the terms used to describe the present invention shall be given their common meaning as understood by those of ordinary skill in the art.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The term "recombinant hemoglobin(s)" as used herein indicates a hemoglobin molecule and/or its variant with a molecular size of at least approximately 65 kDa and is synthesized by any standard molecular biology techniques rather than being isolated or purified from any animal or human source.

The term "protein" or "polypeptide" as used herein indicates an organic polymer composed of two or more amino acid monomers and/or analogs thereof. The term "polypeptide" includes amino acid polymers of any length including full length proteins and peptides, as well as analogs and fragments thereof. A polypeptide of three or more amino acids is also called an oligopeptide. As used herein, the term "amino acid", "amino acid monomer", or "amino acid residue" refers to any of the twenty naturally occurring amino acids including synthetic amino acids with unnatural side chains and including both D and L optical isomers. The terms "amino acid analog" and "analog" that are used interchangeably refer to an amino acid in which one or more individual atoms have been replaced, either with a different atom, isotope, or with a different functional group but is otherwise identical to its natural amino acid analog and have similar chemical and/or physical properties to its natural amino acid analog.

As used herein, the term "variant" refers to a polypeptide or polynucleotide sequence differing from a reference polypeptide or polynucleotide sequence, but retaining essential properties thereof. Generally, variants are overall closely similar, and, in many regions, identical to the reference polypeptide or polynucleotide sequence.

A variant can, for example, comprise the amino acid sequence of the parent polypeptide sequence with at least one conservative amino acid substitution. Alternatively or additionally, the variant can comprise the amino acid sequence of the parent polypeptide sequence with at least one non-conservative amino acid substitution. In this case, it is preferable for the non-conservative amino acid substitution to not interfere with or inhibit the biological activity of the functional variant. The non-conservative amino acid substitution may enhance the biological activity of the variant, such that the biological activity of the variant is increased as compared to the parent polypeptide.

The term "amino acid modification" as used herein indicates amino acid insertion, substitution, or deletion, etc. Amino acid substitutions of the described polypeptides can be conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gln, Ser, Thr, Tyr, etc.), an amino acid with a beta-branched side-chain substituted for another amino acid with a beta-branched side-chain (e.g., Ile, Thr, and Val), an amino acid with an aromatic side-chain substituted for another amino acid with an aromatic side chain (e.g., His, Phe, Trp, and Tyr), etc.

The term "percentage sequence homology", when used in reference to a polypeptide or polynucleotide sequence, refers to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions for the longer sequence in the window of comparison and multiplying the result by 100 to yield the percentage of sequence homology. Homology is evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988, Proc. Natl. Acad. Sci. USA 85(8):2444-2448; Altschul et al., 1990, J. Mol. Biol. 215(3):403-410; Thompson et al., 1994, Nucleic Acids Res. 22(2):4673-4680; Higgins et al. 1996, Methods Enzymol. 266:383-402; Altschul et al., 1990, J. Mol. Biol. 215(3):403-410; Altschul et al., 1993, Nature Genetics 3:266-272). In certain embodiments, protein and nucleic acid sequence homologies are evaluated using the Basic Local Alignment Search Tool ("BLAST") which is well known in the art (see, e.g., Karlin and Altschul, 1990, Proc. Natl. Acad. Sci. USA 87:2267-2268; Altschul et al., 1990, J. Mol. Biol. 215:403-410; Altschul et al., 1993, Nature Genetics 3:266-272; Altschul et al., 1997, Nuc. Acids Res. 25:3389-3402).

As used herein, the terms "treat", "treating", "treatment", and the like refer to reducing or ameliorating a disorder/disease and/or symptoms associated therewith. It will be appreciated, although not precluded, treating a disorder or condition does not require that the disorder, condition, or symptoms associated therewith be completely eliminated. In certain embodiments, treatment includes prevention of a disorder or condition, and/or symptoms associated therewith. The term "prevention" or "prevent" as used herein refers to any action that inhibits or at least delays the development of a disorder, condition, or symptoms associated therewith. Prevention can include primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

The term "subject" as used herein, refers to an animal, typically a mammal or a human, that will be or has been the object of treatment, observation, and/or experiment. When the term is used in conjunction with administration of a compound described herein, then the subject has been the object of treatment, observation, and/or administration of the compound described herein.

The term "therapeutically effective amount" as used herein, means that amount of the compound or pharmaceutical agent that elicits a biological and/or medicinal response in a cell culture, tissue system, subject, animal, or human that is being sought by a researcher, veterinarian, clinician, or physician, which includes alleviation of the symptoms of the disease, condition, or disorder being treated.

The term "composition" is intended to encompass a product comprising the specified ingredients in the specified amounts, as well as any product that results, directly or indirectly, from combinations of the specified ingredients in the specified amounts.

The term "fluorescent dye" refers interchangeably to molecules, groups or radicals which are fluorescent. The term "fluorescent" as applied to a molecule or compound is used to refer to the property of the compound of absorbing energy (such as UV, visible or IR radiation) and re-emitting at least a fraction of that energy as light over time. Fluorescent dyes include, but are not limited to small molecules, proteins and macromolecular complexes.

The term "pharmaceutically acceptable carrier" refers to a medium that is used to prepare a desired dosage form of a compound. A pharmaceutically acceptable carrier can include one or more solvents, diluents, or other liquid vehicles; dispersion or suspension aids; surface active agents; isotonic agents; thickening or emulsifying agents; preservatives; solid binders; lubricants; and the like. Remington's Pharmaceutical Sciences, Fifteenth Edition, E. W. Martin (Mack Publishing Co., Easton, Pa., 1975) and Handbook of Pharmaceutical Excipients, Third Edition, A. H. Kibbe ed. (American Pharmaceutical Assoc. 2000), disclose various carriers used in formulating pharmaceutical compositions and known techniques for the preparation thereof.

The present disclosure provides a hemoglobin-based therapeutic agent comprising a hemoglobin and a chemotherapeutic agent selected from the group consisting of maytansinoid, an auristatin, and a calicheamicin, wherein the chemotherapeutic agent is covalently attached to the hemoglobin via a linker.

The hemoglobin can be bovine hemoglobin, human hemoglobin, canine hemoglobin, porcine hemoglobin, equine hemoglobin and recombinant hemoglobin or a subunit thereof human hemoglobin, bovine hemoglobin, porcine hemoglobin, ovine hemoglobin, equine hemoglobin, or blood from other invertebrates and recombinant and/or transgenically produced hemoglobin.

In certain embodiments, the hemoglobin comprises a di-alpha chain and two beta chains ($2\alpha\beta_2$) as described in U.S. patent application Ser. No. 16/777,932, which is hereby incorporated by reference.

In certain embodiments, the di-alpha chain comprises a polypeptide sequence having at least 98.93% sequence homology with SEQ ID NO: 1. Polypeptides having at least 98.93% sequence homology to SEQ ID NO:1 can refer to polypeptides having at most three amino acid modifications, i.e. zero, one, two, or three amino acid modifications with respect to the SEQ ID NO: 1. In certain embodiments, the di-alpha chain comprises a polypeptide sequence having at least 99.29% sequence homology with the SEQ ID NO: 1. Polypeptides having at least 99.29% sequence homology can have at most two amino acid modifications, i.e. zero, one, or two amino acid modifications with respect to the SEQ ID NO: 1. In certain embodiments, the di-alpha chain comprises a polypeptide sequence having at least 99.64% sequence homology with the SEQ ID NO: 1. Polypeptides having at least 99.64% sequence homology can have at most one amino acid modifications, i.e. zero or one amino acid modification with respect to the SEQ ID NO: 1. In certain embodiments, the di-alpha chain comprises a polypeptide sequence of SEQ ID NO: 1. In certain embodiments, the di-alpha chain consists of a polypeptide sequence of SEQ ID NO: 1. The one, two, or three amino acid modifications can occur at any amino acid present in SEQ ID NO: 1, except the positions 1, 29, 58, 143, 171, and 200 of SEQ ID NO: 1, in which position 1 and position 143 of SEQ ID NO: 1 must be methionine, the amino acids at position 29 and position 171 of SEQ ID NO: 1 must be phenylalanine, and the amino acids at position 58 and position 200 of SEQ ID NO: 1 must be glutamine.

Each of the two beta chains can comprise a polypeptide sequence having at least 97.94% sequence homology with SEQ ID NO: 2. Polypeptides having at least 97.94% sequence homology can have at most three amino acid modifications, i.e. zero, one, two, or three amino acid modifications with respect to the SEQ ID NO: 2. In certain embodiments, each of the two beta chains comprises a polypeptide sequence having at least 98.63% sequence homology with the SEQ ID NO: 2. Polypeptides having at least 98.63% sequence homology can have at most two amino acid modifications, i.e. zero, one, or two amino acid modifications with respect to the SEQ ID NO: 2. In certain embodiments, each of the two beta chains comprises a polypeptide sequence having at least 99.31% sequence homology with the SEQ ID NO: 2. Polypeptides having at least 99.31% sequence homology can have at most one amino acid modifications, i.e. zero or one amino acid modification with respect to the SEQ ID NO: 2. In certain embodiments, each of the two beta chains comprises a polypeptide sequence of SEQ ID NO: 2. In certain embodiments, the one, two, or three amino acid modifications can occur at any amino acid present in SEQ ID NO: 2, except the position 1 of the SEQ ID NO: 2, which must be methionine.

While the examples below are generally directed to a hemoglobin-based therapeutic agent comprising a 2αβ$_2$ hemoglobin, other forms of hemoglobin are also contemplated by the present disclosure, such as naturally occurring and non-naturally occurring tetrameric hemoglobin, e.g., α$_2$β$_2$ and α$_2$γ$_2$; other trimeric forms of hemoglobin, e.g., α$_2$2β, 2αγ$_2$, and α$_2$2γ; dimeric hemoglobin, e.g., 2α2β and 2α2γ; and the like; as well as polymeric forms of hemoglobin comprising one or more monomeric forms of hemoglobin; and hemoglobin derivatives that have been subjected to other methods of chemical modification including, but not limited to, methods for conjugation to polyalkylene oxide, reaction with pyridoxal phosphate, reaction with a dialdehyde, reaction with reagents such as, bis(3,5-dibromosalicyl) fumarate (DBBF), bis(3,5-dibromosalicyl) succinate (DBBS), trimesoyl tris(3,5-dibromosalicylate) (TTDS), or nor-2-formylpyridoxal, 2,3-diphosphoglycerate (2,3-DPG) or chemically similar compounds, or reaction with bis-diaspirin ester.

The hemoglobin-based therapeutic agent can have a MDR between 0.1-5.0. In certain embodiments, the hemoglobin-based therapeutic agent has a MDR of 0.5-5.0, 0.1-2.0, 0.5-2.0, 1.0-2.0, 1.5-2.0, 1.0-5.0, 1.5-5.0, 2.0-5.0, 2.5-5.0, 2.5-4.5, 2.5-4.0, 2.5-3.5, 2.6-3.4, 2.7-3.3, 2.8-3.2, 2.9-3.1, 3.0-5.0, 3.5-5.0, 4.0-5.0, or 4.5-5.0.

The linker can have the Formula 1:

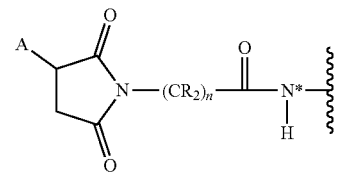

1 wherein A is the chemotherapeutic agent;
N* represents a nitrogen in a lysine side chain in the hemoglobin or a N-terminal amine in the hemoglobin;
n is a whole number selected from 1-10; and
each R is hydrogen; or two R taken together with the carbons to which they are attached form a 3-7 membered cycloalkane and each remaining R is hydrogen; or
the linker has the Formula 2:

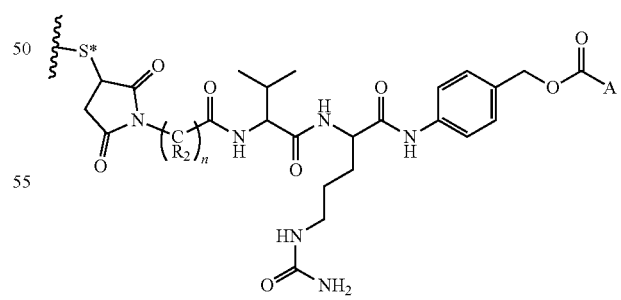

2 wherein A is the chemotherapeutic;
N* represents a nitrogen in a lysine side chain in the hemoglobin or a N-terminal amine in the hemoglobin;

S* represents a sulfur in a cysteine side chain in the hemoglobin;

n is a whole number selected from 1-10; and each R is hydrogen; or two R taken together with the carbons to which they are attached form a 3-7 membered cycloalkane and each remaining R is hydrogen.

In certain embodiments, n is a whole number selected from 1-9, 1-8, 2-8, 2-6, 3-6, or 4-6.

In instances in which two R taken together with the carbons to which they are attached form a 3-7 membered cycloalkane and each remaining R is hydrogen, the linker can be represented by the Formula 1A:

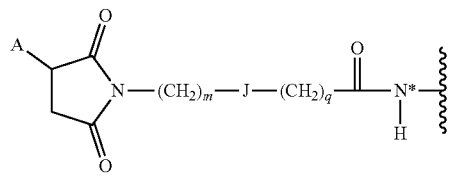

wherein J represents a 3-7 membered cycloalkane; m is an integer selected from 0-9; and q is an integer selected from 0-9, with the proviso that m+q≤9.

In certain embodiments, two R taken together with the carbons to which they are attached form a 4-7, a 3-6, a 4-6, or a 5-6 membered cycloalkane.

In instances in which the linker has the Formula 2, n can be a whole number selected from 1-10; and each R is hydrogen. In certain embodiments, the linker has Formula 2, n is a whole number selected between 1-9, 1-8, 2-8, 2-6, 3-6, or 4-6; and each R is hydrogen.

In certain embodiments, the linker is selected from the group consisting of:

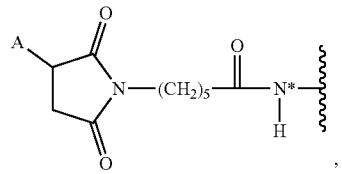

,

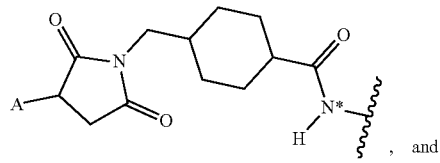

, and

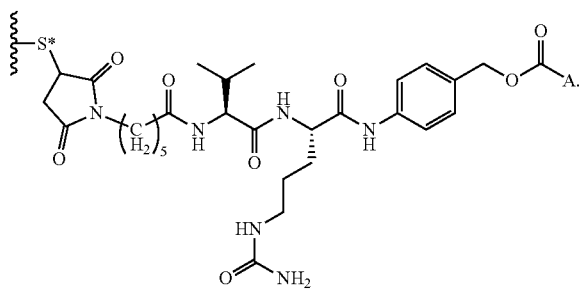

In certain embodiments, the hemoglobin-based therapeutic agent has the Formula 5:

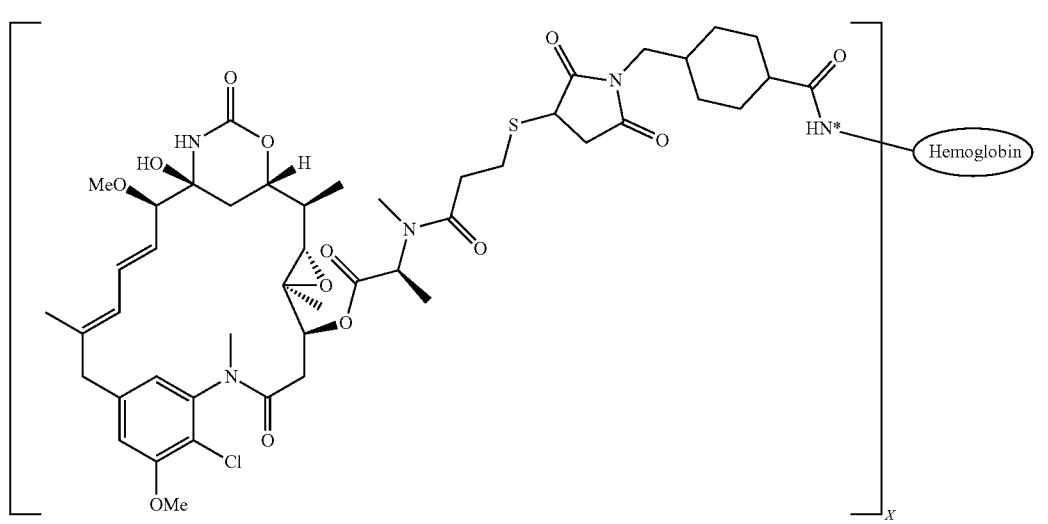

SMCC-DM1 wherein each N* independently represents a nitrogen in a lysine side chain in the hemoglobin or a N-terminal amine in the hemoglobin; and X is the MDR of the hemoglobin-based therapeutic agent of Formula 5, wherein the MDR is between 0.1-5.0.

In certain embodiments, the MDR of hemoglobin-based therapeutic agent of Formula 5 is between 0.5-5.0, 1.0-5.0, 1.5-5.0, 2.0-5.0, 2.5-5.0, 3.0-5.0, 3.5-5.0, 4.0-5.0, or 4.5-5.0. In certain embodiments, the MDR of hemoglobin-based therapeutic agent of Formula 5 is between 2.0-5.0, 2.0-4.5, 2.5-4.5, 3.0-4.5, 3.0-4.0, 3.0-3.5, 3.0-3.5, 3.1-3.5, 3.2-3.5, 3.3-3.5, 3.4-3.5, 3.0-3.4, 3.0-3.3, 3.0-3.2, or 3.1-3.2. In certain embodiments, the MDR of hemoglobin-based therapeutic agent of Formula 5 is between 0.5-5.0, 1.0-5.0, 0.8-5.0, 0.8-4.6, 1.0-4.6, 1.2-4.6, 1.0-3.5, 1.0-3.4, 1.0-3.3, 1.0-3.2, 1.0-3.1, 1.0-3.0, 2.2-3.5, 2.2-3.4, 2.2-3.3, 2.2-3.2, 2.2-3.1, 2.2-3.0, 3.0-3.5, 3.0-3.4, 3.0-3.3, 3.0-3.2, 3.0-3.1, 3.1-3.5, 3.2-3.5, 3.3-3.5, or 3.4-3.5.

In certain embodiments, the hemoglobin-based therapeutic agent has the Formula 6:

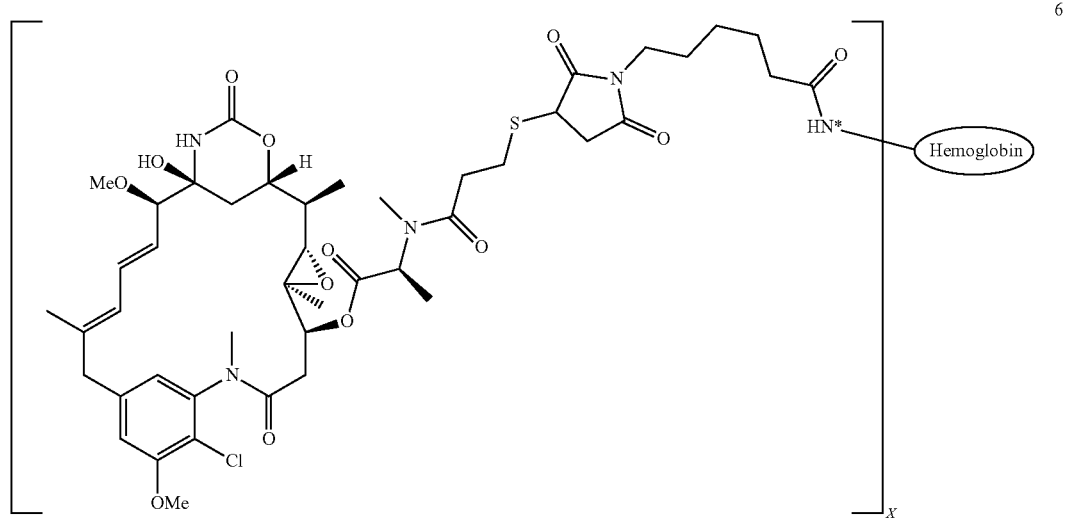

EMCS-DM1 each N* independently represents a nitrogen in a lysine side chain in the hemoglobin or a N-terminal amine in the hemoglobin; and X is the MDR of the hemoglobin-based therapeutic agent of Formula 6, wherein the MDR is between 0.1-5.0.

In certain embodiments, the MDR of hemoglobin-based therapeutic agent of Formula 6 is 0.5-5.0, 1.0-5.0, 1.5-5.0, 2.0-5.0, 2.5-5.0, 3.0-5.0, 3.5-5.0, 4.0-5.0, or 4.5-5.0. In certain embodiments, the MDR of hemoglobin-based therapeutic agent of Formula 6 is between 2.0-5.0, 2.0-4.5, 2.5-4.5, 3.0-4.5, 3.0-4.0, 3.0-3.5, 3.0-3.5, 3.1-3.5, 3.2-3.5, 3.3-3.5, 3.4-3.5, 3.0-3.4, 3.0-3.3, 3.0-3.2, or 3.1-3.2. In certain embodiments, the MDR of hemoglobin-based therapeutic agent of Formula 6 is between 0.5-5.0, 1.0-5.0, 0.8-5.0, 0.8-4.6, 1.0-4.6, 1.2-4.6, 1.0-3.5, 1.0-3.4, 1.0-3.3, 1.0-3.2, 1.0-3.1, 1.0-3.0, 2.2-3.5, 2.2-3.4, 2.2-3.3, 2.2-3.2, 2.2-3.1, 2.2-3.0, 3.0-3.5, 3.0-3.4, 3.0-3.3, 3.0-3.2, 3.0-3.1, 3.1-3.5, 3.2-3.5, 3.3-3.5, or 3.4-3.5.

In certain embodiments, the hemoglobin-based therapeutic agent has the Formula 7:

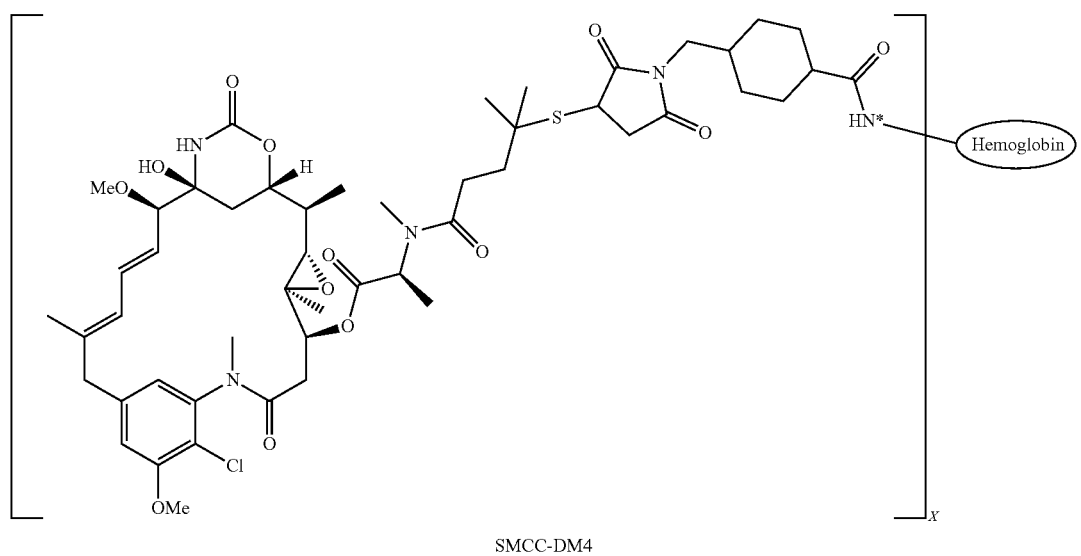

SMCC-DM4 each N* independently represents a nitrogen in a lysine side chain in the hemoglobin or a N-terminal amine in the hemoglobin; and X is the MDR of the hemoglobin-based therapeutic agent of Formula 7, wherein the MDR is between 0.1-5.0.

In certain embodiments, the MDR of hemoglobin-based therapeutic agent of Formula 7 is between 0.5-5.0, 1.0-5.0, 1.5-5.0, 2.0-5.0, 2.5-5.0, 3.0-5.0, 3.5-5.0, 4.0-5.0, or 4.5-5.0. In certain embodiments, the MDR of hemoglobin-based therapeutic agent of Formula 7 is between 2.0-5.0, 2.0-4.5, 2.5-4.5, 3.0-4.5, 3.0-4.0, 3.0-3.5, 3.0-3.5, 3.1-3.5, 3.2-3.5, 3.3-3.5, 3.4-3.5, 3.0-3.4, 3.0-3.3, 3.0-3.2, or 3.1-3.2. In certain embodiments, the MDR of hemoglobin-based therapeutic agent of Formula 7 is between 0.5-5.0, 1.0-5.0, 0.8-5.0, 0.8-4.6, 1.0-4.6, 1.2-4.6, 1.0-3.5, 1.0-3.4, 1.0-3.3, 1.0-3.2, 1.0-3.1, 1.0-3.0, 2.2-3.5, 2.2-3.4, 2.2-3.3, 2.2-3.2, 2.2-3.1, 2.2-3.0, 3.0-3.5, 3.0-3.4, 3.0-3.3, 3.0-3.2, 3.0-3.1, 3.1-3.5, 3.2-3.5, 3.3-3.5, or 3.4-3.5.

In certain embodiments, the hemoglobin-based therapeutic agent has the Formula 8:

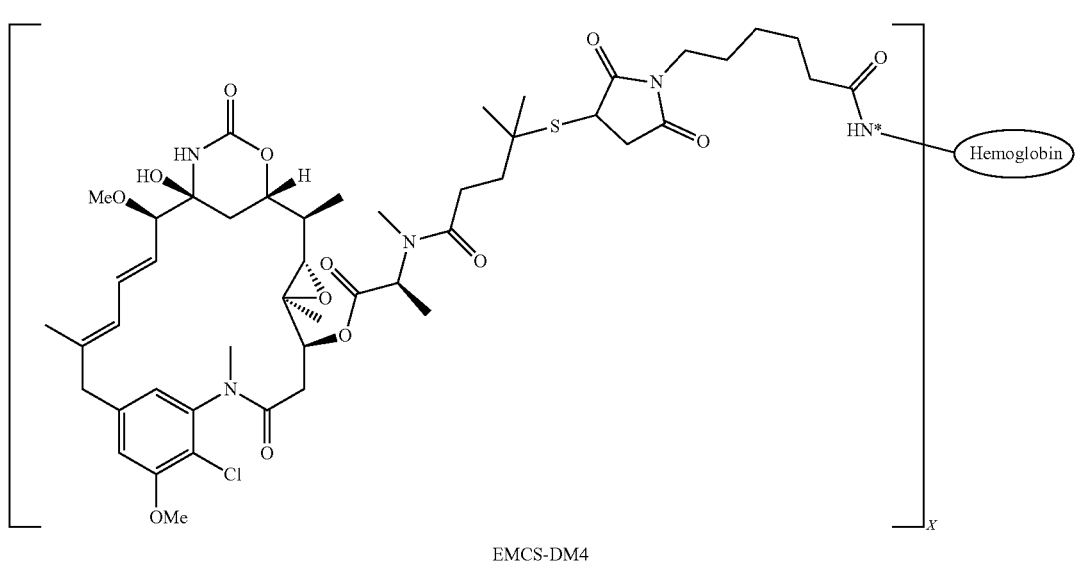

EMCS-DM4

N* represents a nitrogen from a lysine side chain or a nitrogen from a N-terminal amine; and X is the MDR of the hemoglobin-based therapeutic agent of Formula 8, wherein the MDR is between 0.1-5.0.

In certain embodiments, the MDR of hemoglobin-based therapeutic agent of Formula 8 is 0.5-5.0, 1.0-5.0, 1.5-5.0, 2.0-5.0, 2.5-5.0, 3.0-5.0, 3.5-5.0, 4.0-5.0, or 4.5-5.0. In certain embodiments, the MDR of hemoglobin-based therapeutic agent of Formula 8 is 2.0-5.0, 2.0-4.5, 2.5-4.5, 3.0-4.5, 3.0-4.0, 3.0-3.5, 3.0-3.5, 3.1-3.5, 3.2-3.5, 3.3-3.5, 3.4-3.5, 3.0-3.4, 3.0-3.3, 3.0-3.2, or 3.1-3.2. In certain embodiments, the MDR of hemoglobin-based therapeutic agent of Formula 8 is 0.5-5.0, 1.0-5.0, 0.8-5.0, 0.8-4.6, 1.0-4.6, 1.2-4.6, 1.0-3.5, 1.0-3.4, 1.0-3.3, 1.0-3.2, 1.0-3.1, 1.0-3.0, 2.2-3.5, 2.2-3.4, 2.2-3.3, 2.2-3.2, 2.2-3.1, 2.2-3.0, 3.0-3.5, 3.0-3.4, 3.0-3.3, 3.0-3.2, 3.0-3.1, 3.1-3.5, 3.2-3.5, 3.3-3.5, or 3.4-3.5.

Provided herein is a hemoglobin-based therapeutic agent of Formula 9:

benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes.

The present disclosure also provides a pharmaceutical composition comprising a hemoglobin-based therapeutic agent described herein and at least one pharmaceutically acceptable excipient and/or pharmaceutically acceptable carrier.

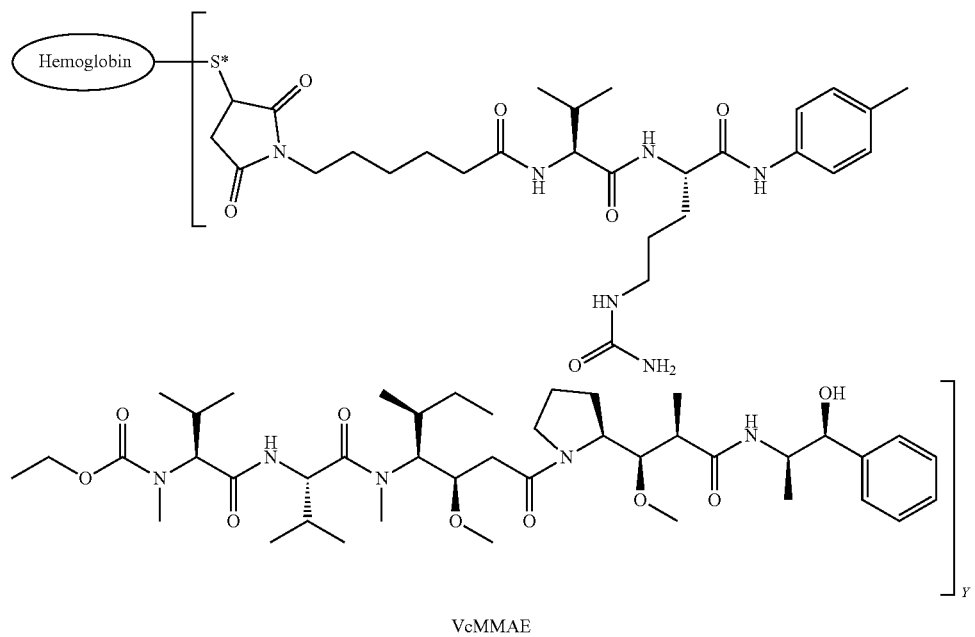

9

VcMMAE each S* independently represents a sulfur in a cysteine side chain in the hemoglobin; and Y is the MDR of the hemoglobin-based therapeutic agent of Formula 9, wherein the MDR is between 0.1-2.0.

In certain embodiments, the MDR of hemoglobin-based therapeutic agent of Formula 9 is between 0.1-2.0, 0.5-2.0, 0.75-2.0, 1.0-2.0, 1.0-1.9, 1.0-1.8, 1.0-1.7, 1.0-1.6, 1.1-1.6, 1.0-1.5, 1.1-1.5, 1.2-1.5, 1.3-1.5, 1.4-1.5, 1.0-1.4, 1.0-1.3, or 1.0-1.2.

Advantageously, the hemoglobin-based therapeutic agent of Formula 9 comprises a cathepsin-cleavable linker. The cathepsin-cleavable linker to the hemoglobin is stable in extracellular fluid, but can be cleaved by cathepsin once the hemoglobin-based therapeutic agent has entered a tumour cell, thus freeing the chemotherapeutic agent.

In certain embodiments, the hemoglobin-based therapeutic agents described herein further comprise a fluorescent dye. The fluorescent agent dye can be connected directly to the hemoglobin-based therapeutic agent or via a linker. Fluorescent dyes are well known in the art, and include, but are not limited to xanthene dyes, e.g., fluorescein and rhodamine dyes, such as fluorescein isothiocyanate (FITC), 6-carboxyfluorescein, 6-carboxy-2',4',7',4,7-hexachlorofluorescein (HEX), 6-carboxy-4', 5'-dichloro-2', 7'-dimethoxyfluorescein, N,N,N',N'-tetramethyl6-carboxyrhodamine, 6-carboxy-xrhodmnine, 5-carboxyrhodamine-6G, 6-carboxyrhodamine-6G, and rhodmnine 110; cyanine dyes, e.g. Cy3, Cy5 and Cy7 dyes; coumarins, e.g umbelliferone;

The hemoglobin-based therapeutic agent described herein can be administered to a subject either alone or in combination with pharmaceutically acceptable carriers or diluents in a pharmaceutical composition according to standard pharmaceutical practice. The hemoglobin-based therapeutic agent can be administered parenterally. Parenteral administration includes intravenous, intramuscular, intraperitoneal, subcutaneous and topical, the preferred method being intravenous administration.

Accordingly, the present disclosure provides pharmaceutically acceptable compositions, which comprise a therapeutically-effective amount of the hemoglobin-based therapeutic agent described herein, formulated together with one or more pharmaceutically acceptable carriers (additives) and/or diluents. The pharmaceutical compositions of the present disclosure may be specially formulated for administration in liquid form, including those adapted for the following: (1) parenteral administration, for example, by intravenous as, for example, a sterile solution or suspension.

Wetting agents, emulsifiers and lubricants, such as sodium lauryl sulfate and magnesium stearate, as well as coloring agents, release agents, coating agents, sweetening, flavoring and perfuming agents, preservatives, solubilizing agents, buffers and antioxidants can also be present in the compositions.

Methods of preparing the pharmaceutical comprising the hemoglobin-based therapeutic agent include the step of bringing into association a hemoglobin-based therapeutic agent described herein with the carrier and, optionally, one or more accessory ingredients. In general, the formulations are prepared by uniformly and intimately bringing into association a hemoglobin-based therapeutic agent described herein with liquid carriers (liquid formulation), liquid carriers followed by lyophilization (powder formulation for reconstitution with sterile water or the like), or finely divided solid carriers, or both, and then, if necessary, shaping or packaging the product.

Pharmaceutical compositions of the present disclosure suitable for parenteral administration can comprise one or more hemoglobin-based therapeutic agents described herein in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, chelating agents, solutes which render the formulation isotonic with the blood of the intended recipient or suspending or thickening agents.

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms upon the compounds of the present disclosure may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In certain embodiments, the pharmaceutical composition comprises one or more of sucrose, trehalose, an amino acid, and phosphate buffer.

The present disclosure also provides a method for preparing the hemoglobin-based therapeutic agents described herein. In certain embodiments, the method for preparing the hemoglobin-based therapeutic agent utilizes a one-step method comprising: contacting a hemoglobin with a compound of Formula 10:

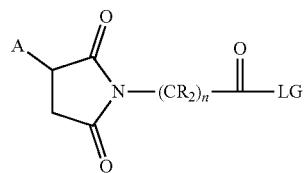

10 wherein A, R, and n are as defined in any embodiment described herein and LG is a leaving group; thereby forming the hemoglobin-based therapeutic agent of Formula 11:

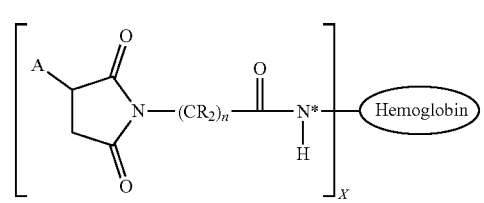

11 wherein N* and X are as defined in any embodiment described herein; or hemoglobin with a compound of Formula 12:

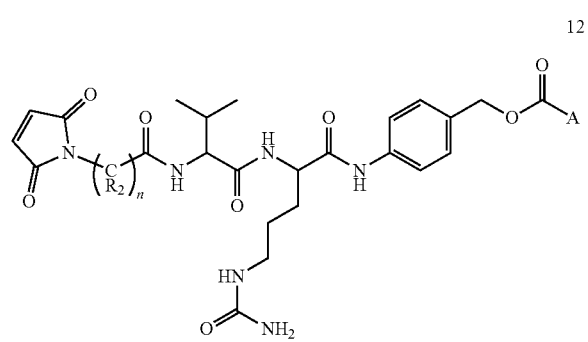

12 wherein A, R, and n are as defined in any embodiment described herein; thereby forming the hemoglobin-based therapeutic agent of Formula 13:

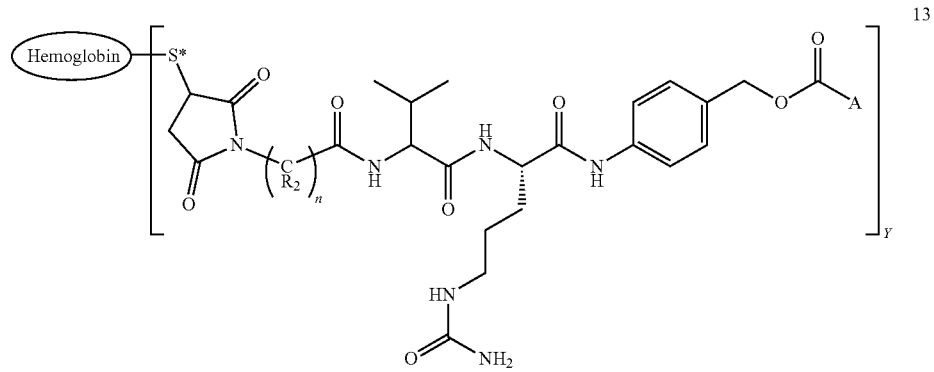

13 wherein S* and Y are as defined in any embodiment described herein.

Any leaving group in the art can be used in connection with the methods described herein. In certain embodiments, LG is selected from the group consisting of: halides,

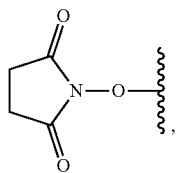 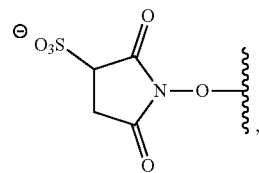 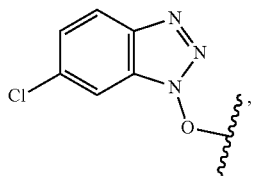 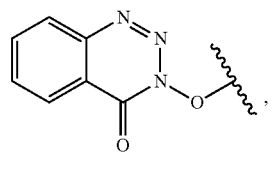

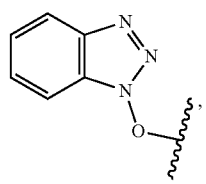 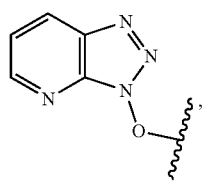 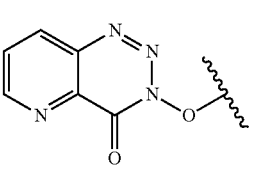 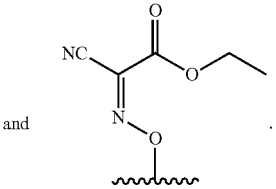, and

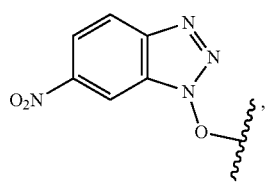 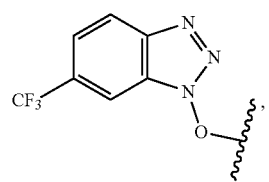

In certain embodiments, the hemoglobin is crosslinked. In such instances, the hemoglobin can be crosslinked, e.g., with DBBF, DBBS, TTDS, or nor-2-formylpyridoxal, prior to the reaction with the compound of Formula 10 or compound of Formula 12.

In certain embodiments, the method for preparing the hemoglobin-based therapeutic agent comprises: contacting hemoglobin with a compound of Formula 14:

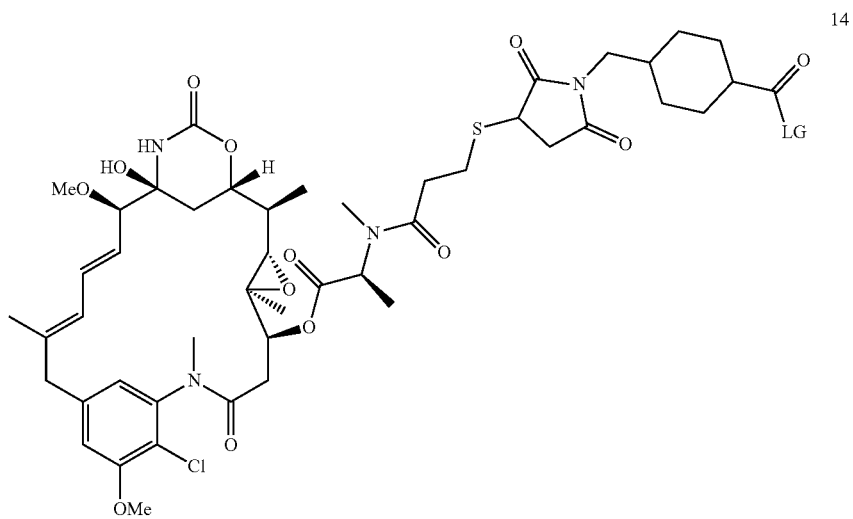

Activated SMCC-DM1 thereby forming the hemoglobin-based therapeutic agent of Formula 5.

In certain embodiments, the method for preparing the hemoglobin-based therapeutic agent comprises: contacting hemoglobin with a compound of Formula 15:

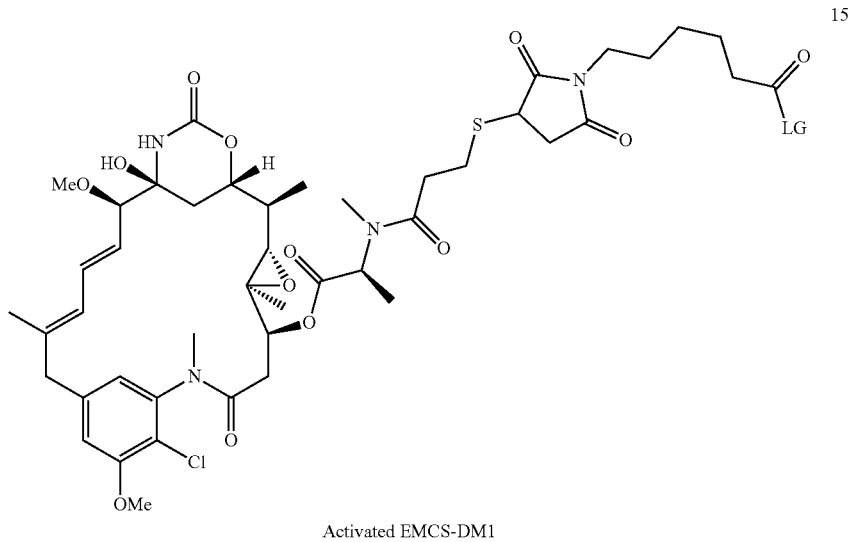

Activated EMCS-DM1 thereby forming the hemoglobin-based therapeutic agent of Formula 6.

In certain embodiments, the method for preparing the hemoglobin-based therapeutic agent comprises: contacting hemoglobin with a compound of Formula 16:

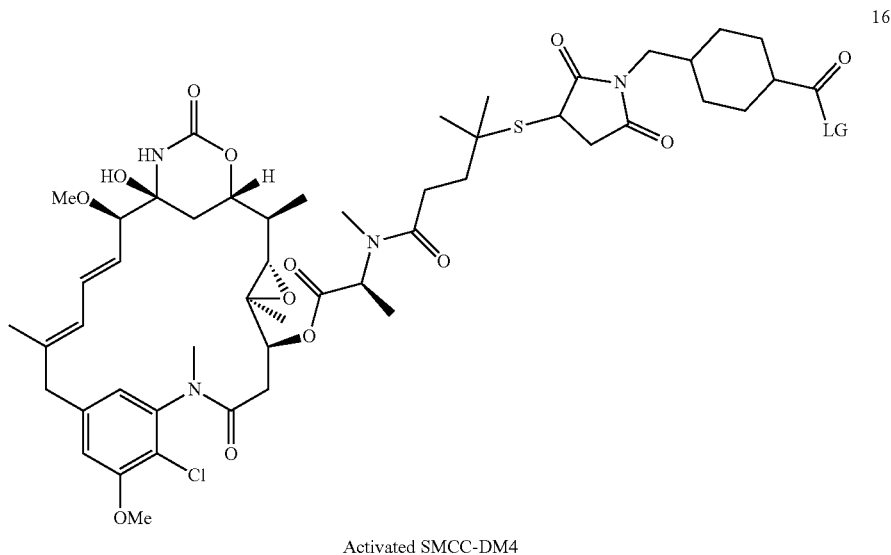

Activated SMCC-DM4 thereby forming the hemoglobin-based therapeutic agent of Formula 7.

In certain embodiments, the method for preparing the hemoglobin-based therapeutic agent comprises: contacting hemoglobin with a compound of Formula 17:

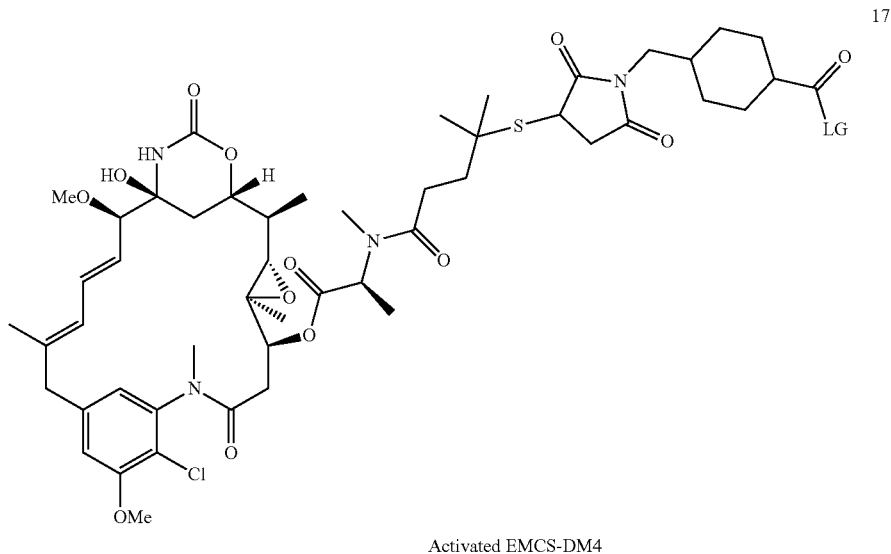

Activated EMCS-DM4 thereby forming the hemoglobin-based therapeutic agent of Formula 8.

Alternatively, the compounds of Formula 10, 14, 15, 16, and 17 can be prepared in situ by reaction of the corresponding carboxylic acids with a peptide coupling agent in the presence of an additive in the presence of hemoglobin thereby forming the hemoglobin-based therapeutic agents of Formula 5, Formula 6, Formula 7, Formula 8, and Formula 11.

The peptide coupling agent can be a carbodiimide, such as DCC, DIC, EDC, CIC, BMC, CPC, BDDC, PIC, PEC, and BEM, a uranium/aminium salt, such as HATU, HBTU, TATU, TBTU, HAPyU, TAPipU, HAPipU, HBPipU, HAMBU, HBMDU, HAMTU, 5,6-B(HATU), 4,5-B (HATU), HCTU, TCTU, and ACTU, phosphonium salts, such as AOP, BOP, PyAOP, PyBOP, PyOxm, PyNOP, PyFOP, NOP, and PyClock, immonium salts, such as BOMI, BDMP, BMMP, BPMP, and AOMP.

The additive can be any peptide coupling additive known in the art, such as HOBt. 6-$NO_2$-HOBt, 6-Cl-HOBt, 6-$CF_3$-HOBt, HOAt, HODhbt, HODhat, HOSu, and Oxyma.

Alternatively, the compounds of Formula 10, 14, 15, 16, and 17 can be prepared by reaction of the corresponding carboxylic acids with disuccinimidyl carbonate (DSC) or N-hydroxysuccinimidyl chloroformate.

The reaction of hemoglobin and he compounds of Formula 10, 14, 15, 16, and 17 can be conducted in a polar aprotic reaction medium, such as DMF, DMA, DMSO, and mixtures thereof. The reaction of hemoglobin and the compounds of Formula 10, 14, 15, 16, and 17 may also be conducted in water or mixtures of water and DMF, DMA, and DMSO.

As demonstrated by the testing results shown in FIGS. 12-14, the MDR of the hemoglobin-based therapeutic agent can be varied by modifying the synthetic route (e.g., one step (FIG. 2B) or two step method (FIG. 2A)) and reaction parameters, such as reagent stoichiometry and concentration (e.g., of the hemoglobin and compounds of Formula 10, 14, 15, 16, and 17), solvent, reaction time, and reaction temperature, the MDR of the hemoglobin-based therapeutic agent can be adjusted to a value between 1.0-4.6.

Depending on the desired MDR of the As demonstrated by the testing results shown in FIGS. 12-14, the MDR of the hemoglobin-based therapeutic agent, the hemoglobin and the compounds of Formula 10, 14, 15, 16, and 17 can be present in the reaction medium in a molar ratio ranging from 1:1 to 1:10. In certain embodiments, the hemoglobin and the compounds of Formula 10, 14, 15, 16, and 17 are present in the reaction medium at a molar ratio of 1:1 to 1:9; 1:1 to 1:8; 1:1 to 1:7; 1:1 to 1:6; 1:2 to 1:6; 1:3 to 1:6; or 1:4 to 1:6.

Alternatively, the method for preparing the hemoglobin-based therapeutic agent can comprise a two-step method comprising: contacting a hemoglobin with a compound of Formula 10A:

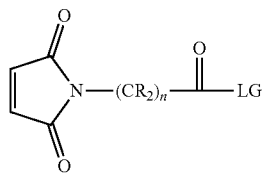

10A wherein R, n, and LG are as defined in any embodiment described herein; thereby forming a compound Formula 11A:

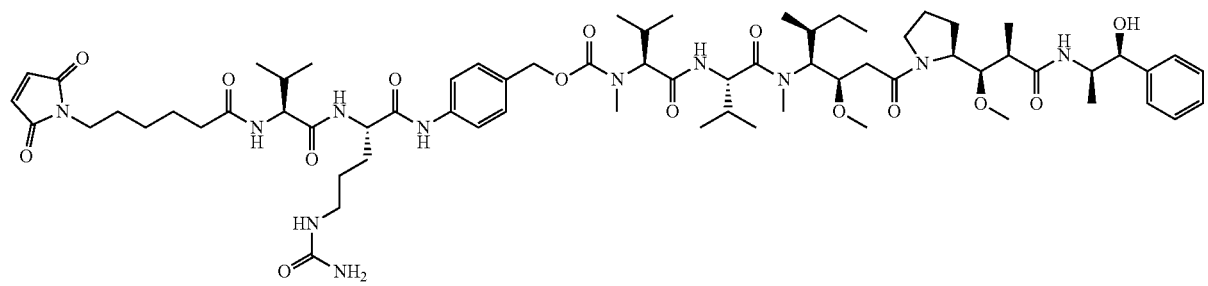

19

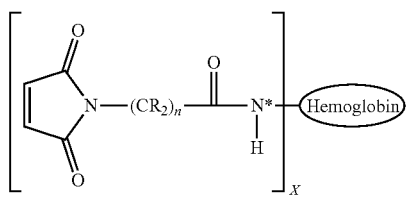

18 wherein N* and X are as defined in any embodiment described herein; and contacting the compound of Formula 11A with the chemotherapeutic agent (e.g., DM1 or DM4) thereby forming a compound of Formula 11:

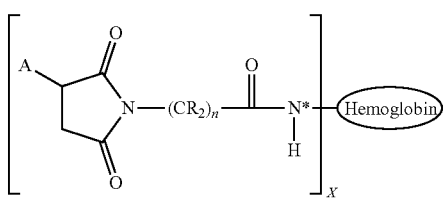

11 wherein N* and X are as defined in any embodiment described herein.

In instances in which a two-step method is used to prepare the compounds described herein, the molar ratio of hemoglobin to the compound of Formula 11A can be present in the reaction medium in a molar ratio ranging from 1:1 to 1:10. In certain embodiments, the hemoglobin and the compound of Formula 11A are present in the reaction medium at a molar ratio of 1:1 to 1:9; 1:1 to 1:8; 1:1 to 1:7; 1:1 to 1:6; 1:2 to 1:6; 1:3 to 1:6; or 1:4 to 1:6.

In instances in which a two-step method is used to prepare the compounds described herein, the molar ratio of the chemotherapeutic agent to the compound of Formula 18 can be present in the reaction medium in a molar ratio ranging from 1:1 to 1:10. In certain embodiments, the hemoglobin and the chemotherapeutic agent to the compound of Formula 18 are present in the reaction medium at a molar ratio of 1:1 to 1:9; 1:1 to 1:8; 1:1 to 1:7; 1:1 to 1:6; 1:2 to 1:6; 1:3 to 1:6; or 1:4 to 1:6.

In certain embodiments, the method for preparing the hemoglobin-based therapeutic agent comprises: contacting hemoglobin with a compound of Formula 19:

thereby forming the hemoglobin-based therapeutic agent of Formula 5.

As discussed in the background, most cancerous tissues, such as cancerous tumors, are hypoxic. Hemoglobin can be used to alleviate the hypoxic condition. Hemoglobin plays an important role in most vertebrates for gaseous exchange between the vascular system and tissue. Hemoglobin is responsible for carrying oxygen from the respiratory system to the body cells via blood circulation and also carries the metabolic waste product carbon dioxide away from body cells to the respiratory system, where the carbon dioxide is exhaled.

Some chemotherapeutic agents (e.g. DM1, DM4, and MMAE) cannot be used clinically, because of high toxicity. In the present disclosure, the chemotherapeutic agents are covalently attached to crosslinked or uncrosslinked hemoglobin (~65 kDa). The source of hemoglobin can be, for example, from bovine, human, canine, porcine, equine and recombinant hemoglobin and/or subunits. Human hemoglobin shares high similarity with bovine, canine, porcine and equine when comparing their amino acid sequences.

The hemoglobin can be modified chemically by different functional groups before linking to the chemotherapeutic agent. In this disclosure, exemplary hemoglobin-based therapeutic agents are prepared by reacting hemoglobin with compounds comprising NHS ester and maleimide, FIG. 1 shows the reaction of hemoglobin with NHS ester and maleimide with different linkers (e.g. SMCC, EMCS, and Vit-Cit) and chemotherapeutic agents (e.g. DM1, DM4, and MMAE).

Figure 2A:
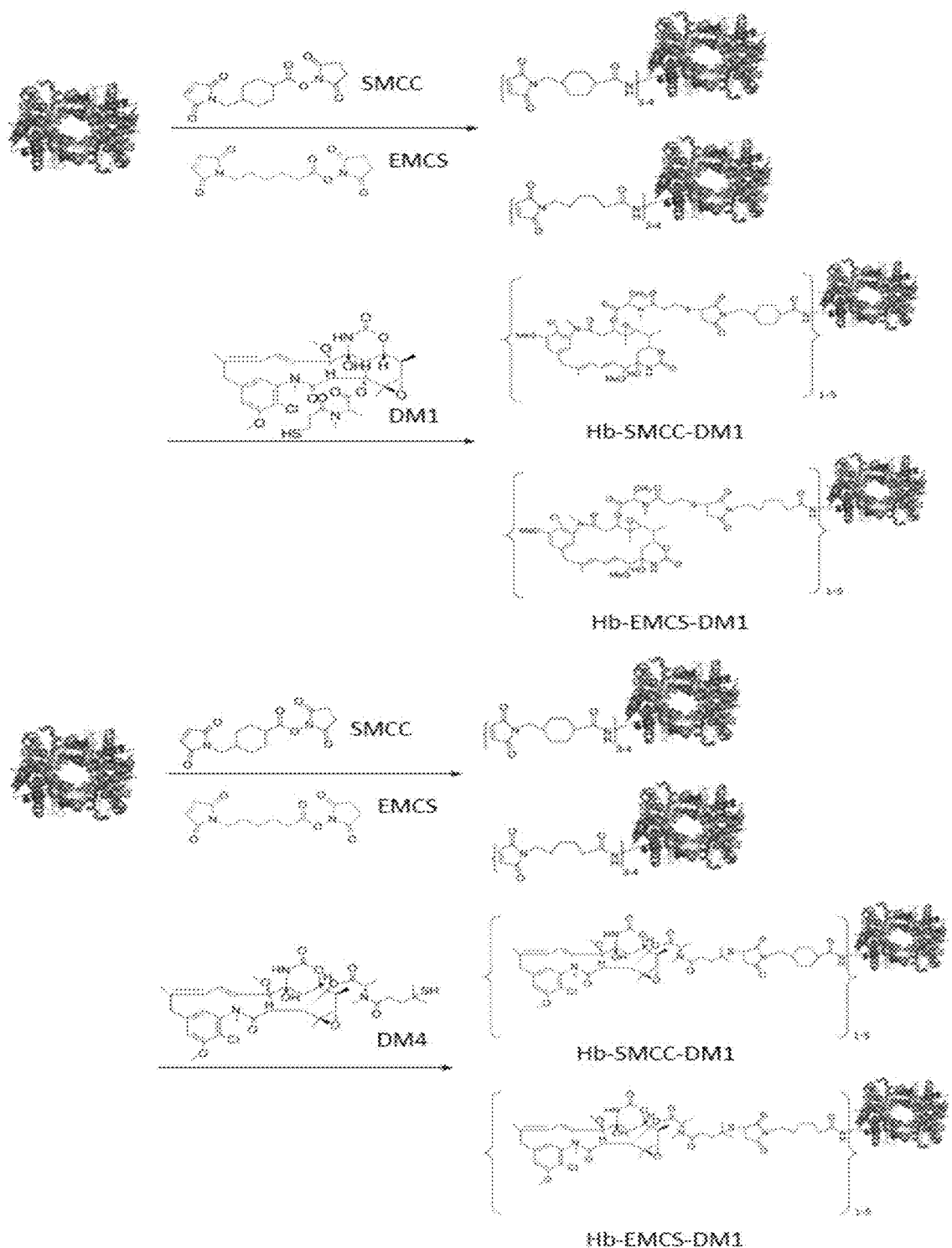
FIG. 2A shows the conjugation scheme for hemoglobin-based therapeutic agents by two-step method in accordance with certain embodiments described herein.
Figure 2B:
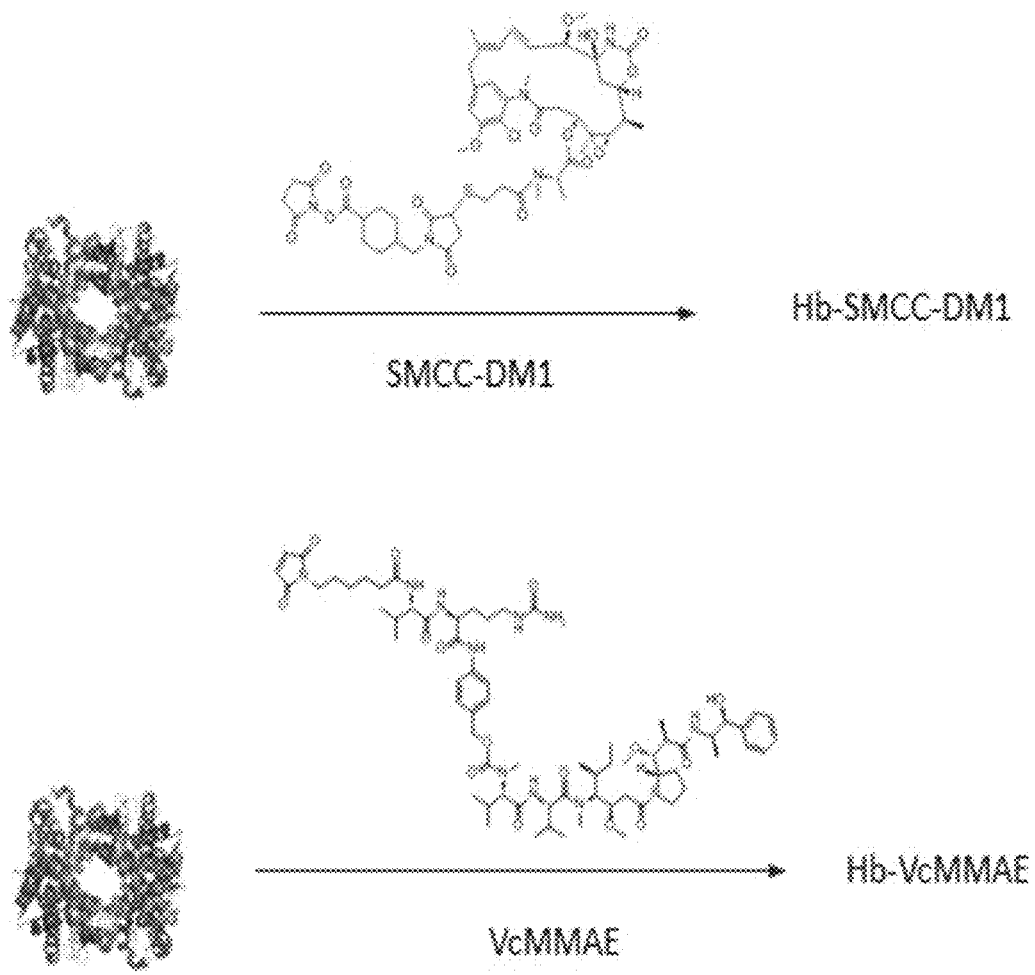
FIG. 2B shows the conjugation scheme for hemoglobin-based therapeutic agents by a one-step method in accordance with certain embodiments described herein.
Figure 3A:
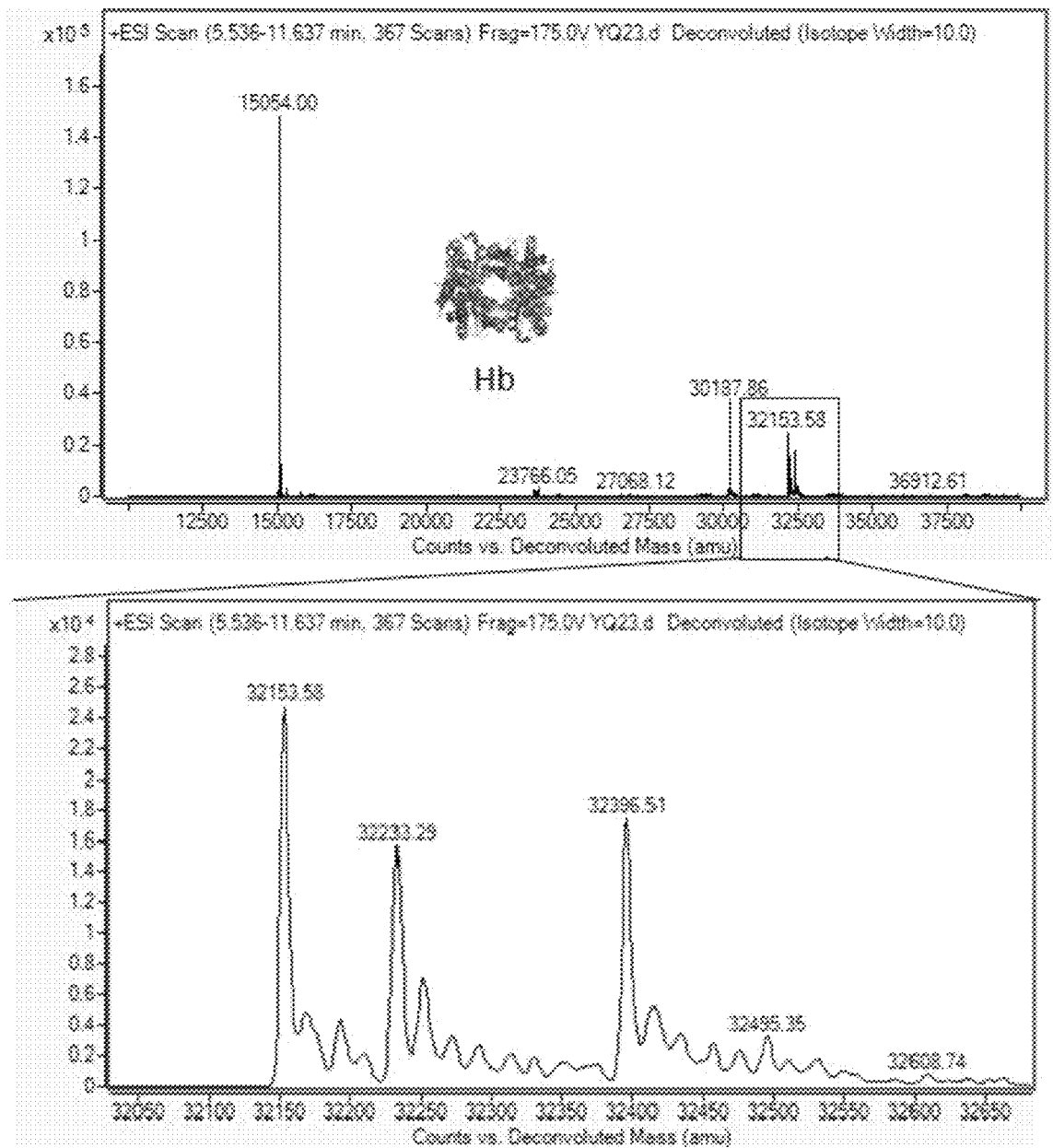
FIG. 3A shows the LC-MS results for hemoglobin.
Figure 3B:
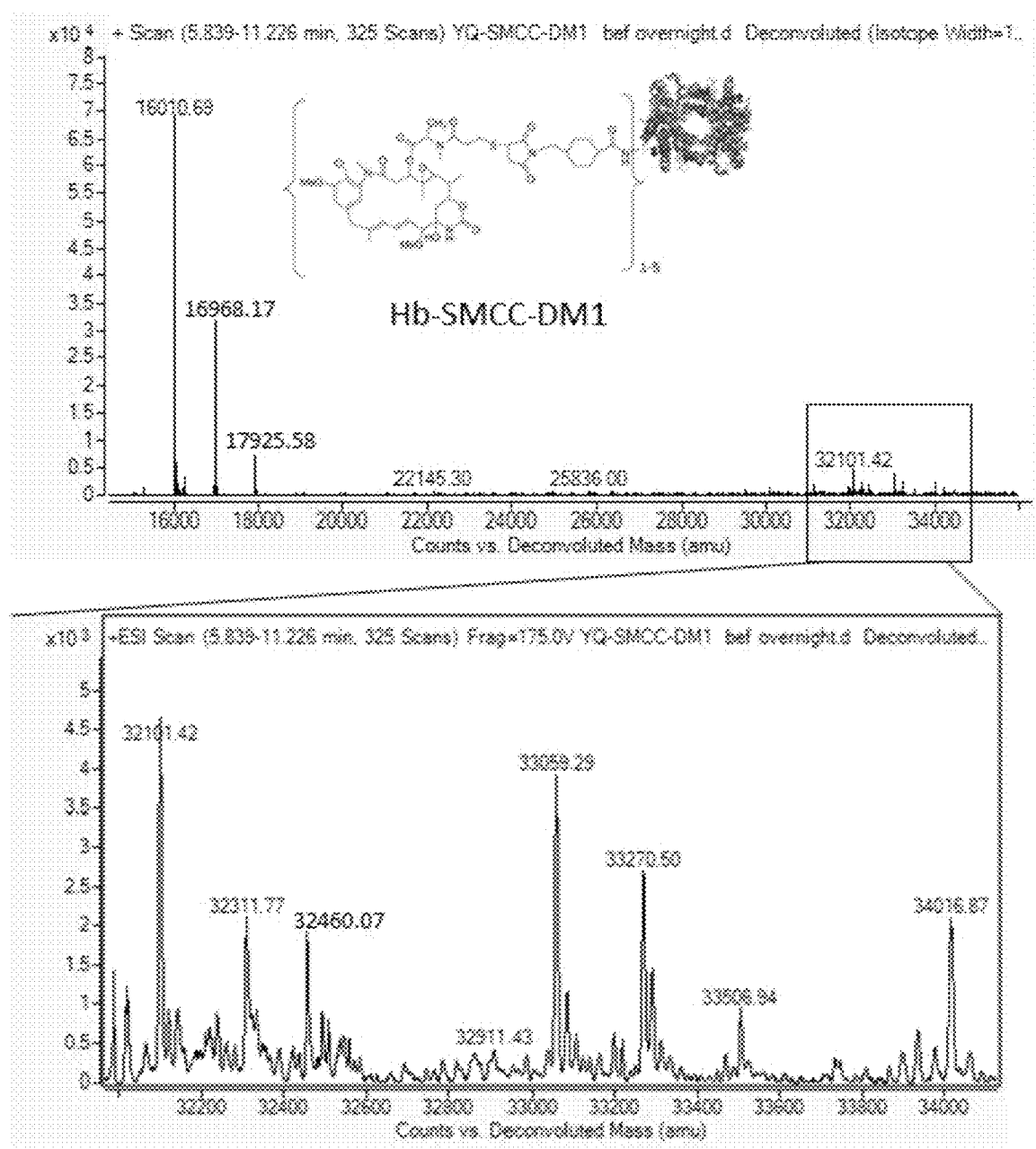
FIG. 3B shows the LC-MS results for Hb-SMCC-DM1 and Hb-EMCS-DM1.
Figure 3B:
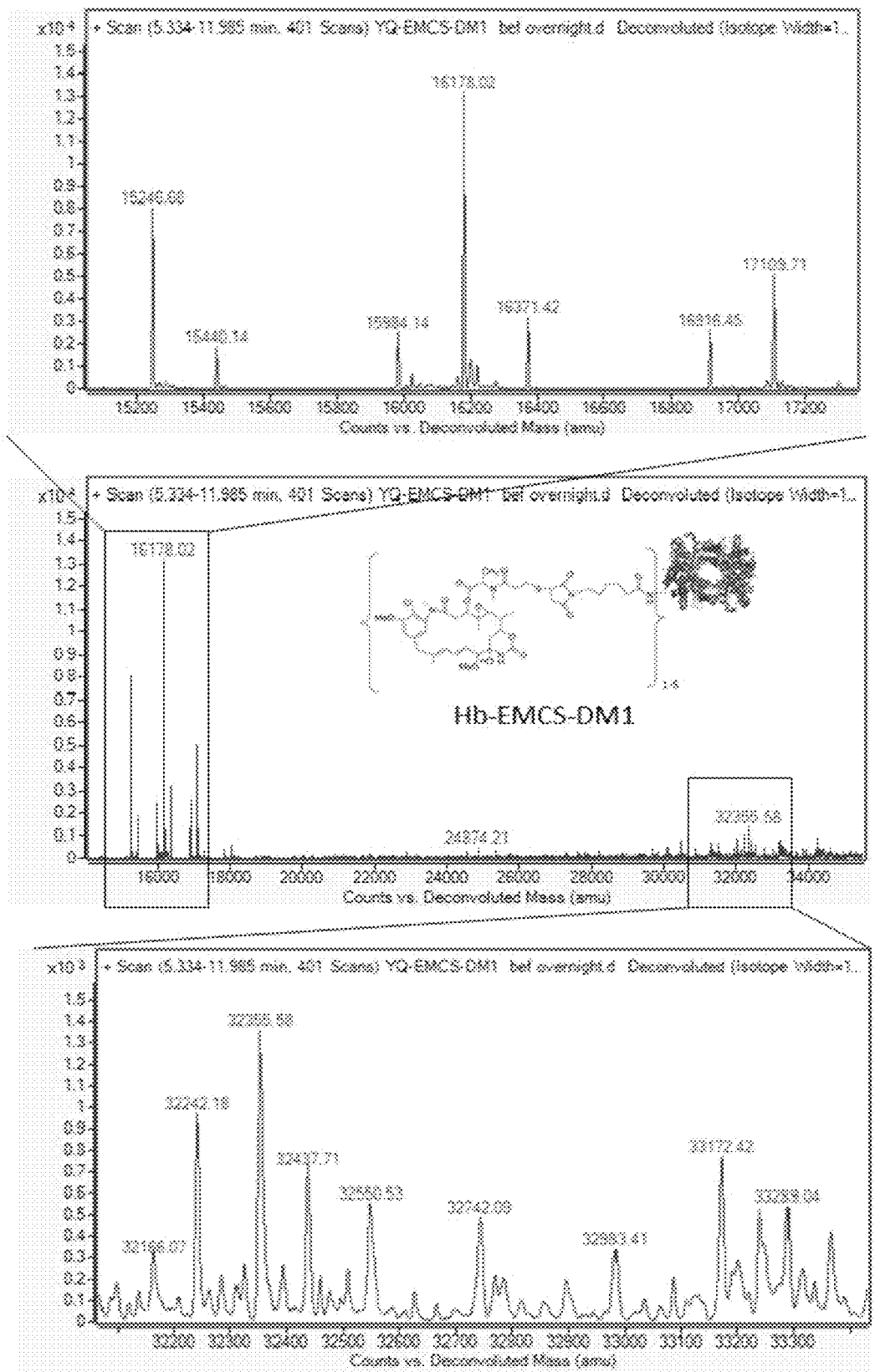
Figure 3C:
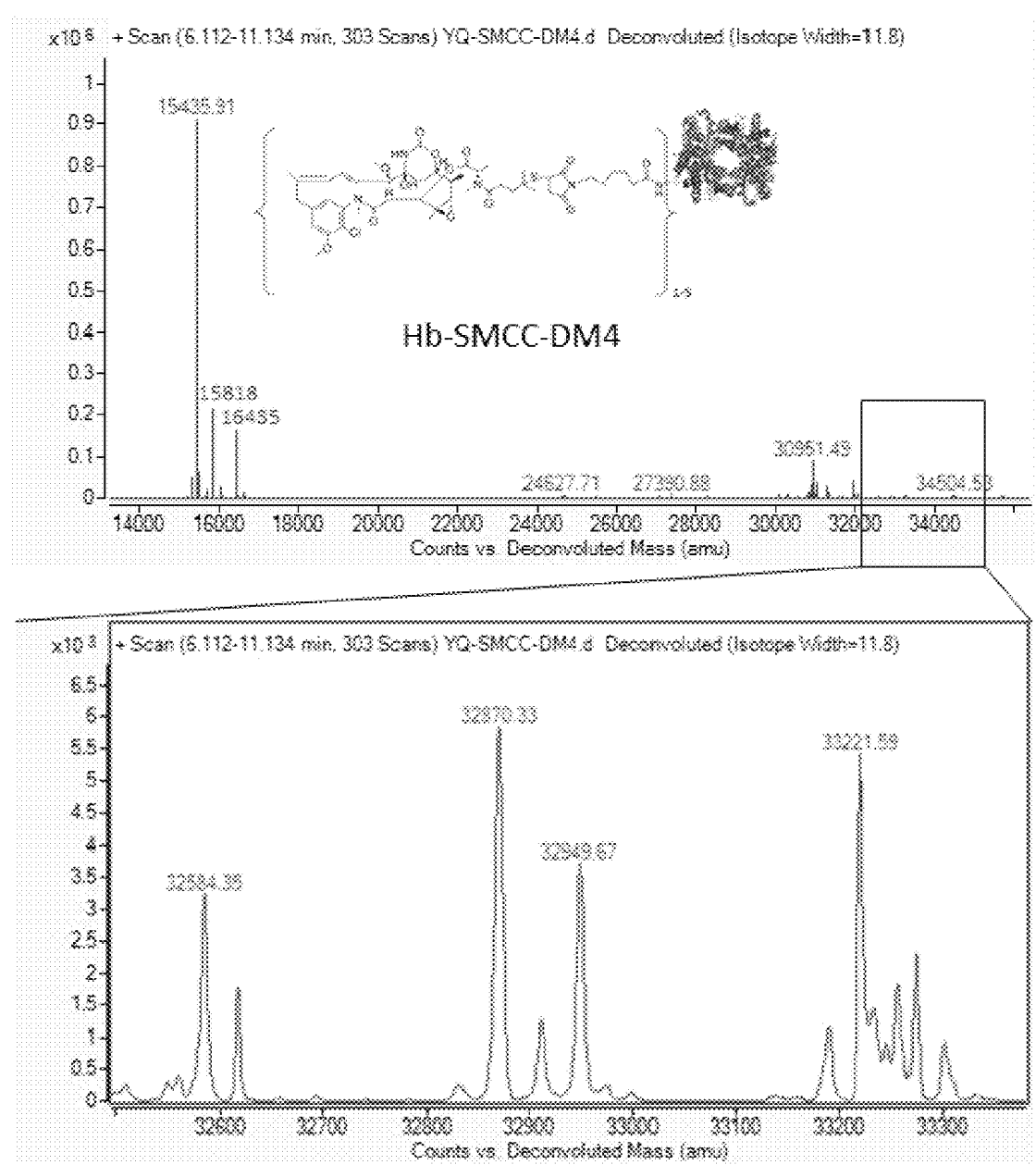
FIG. 3C shows the LC-MS results for Hb-SMCC-DM4 and Hb-EMCS-DM4.
Figure 3C:
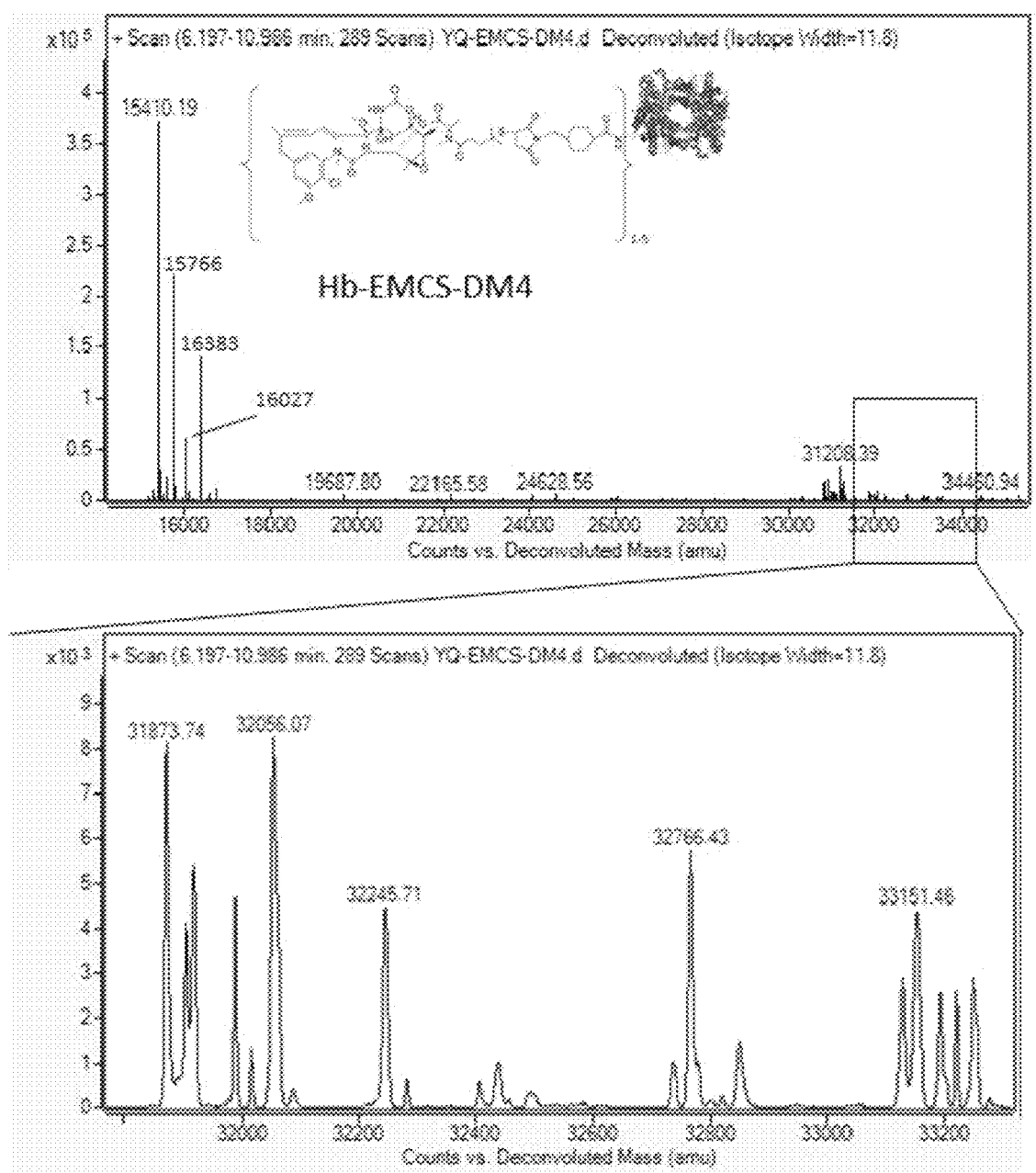
Figure 3D:
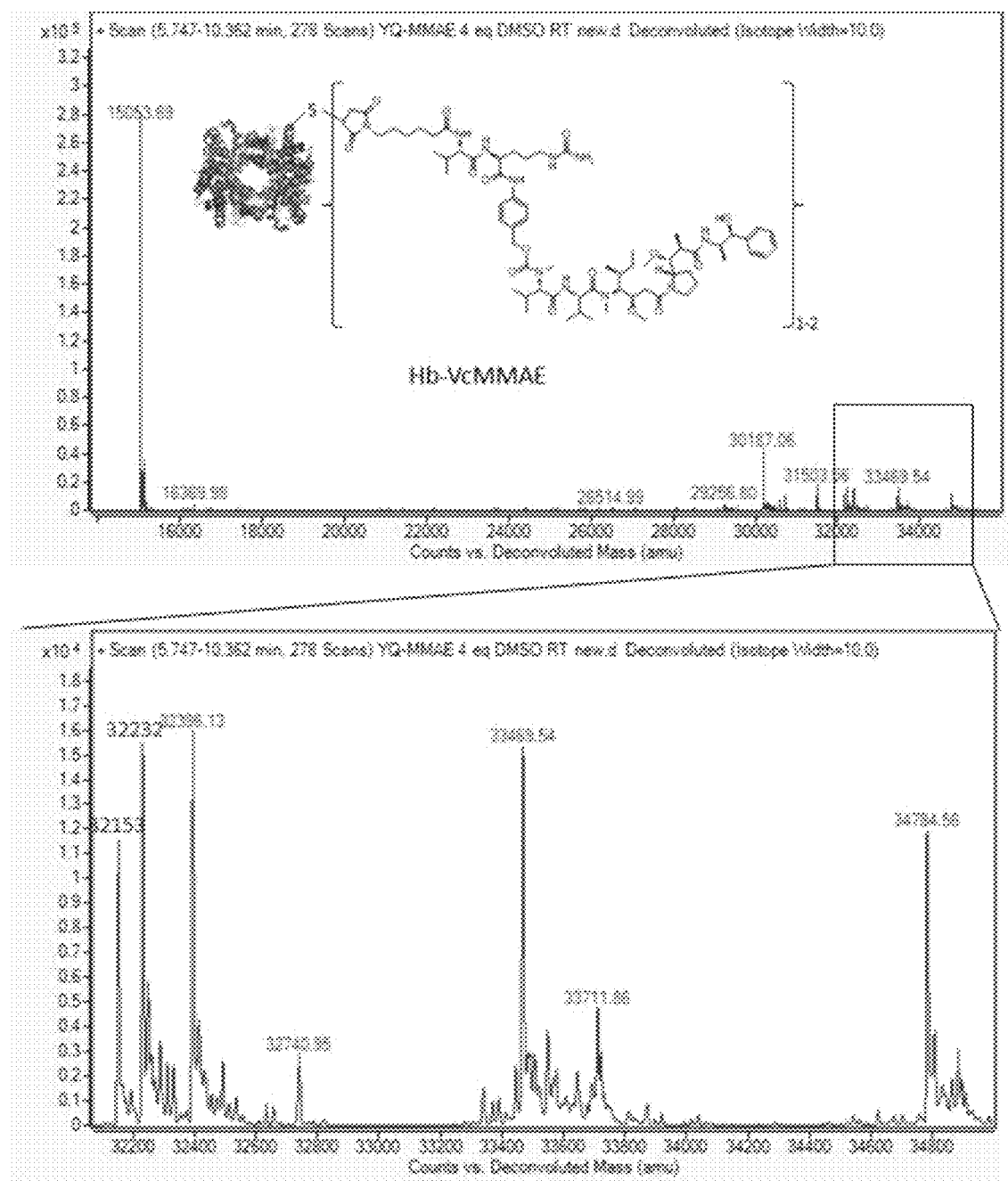
FIG. 3D shows the LC-MS results for Hb-VcMMAE.

Exemplary hemoglobin-based therapeutic agents comprising a chemotherapeutic agents (e.g. DM1 and DM4) and a linker (SMCC and EMCS) prepared by a two-step method is shown in FIG. 2A and the hemoglobin-based therapeutic agent comprising a chemotherapeutic agent (e.g. DM1 and MMAE) using SMCC-DM1 and VcMMAE, respectively, by one-step method is shown in FIG. 2B. It has been successfully demonstrated that the hemoglobin is linked to DM1 and DM4 as shown in the LC-MS experiment. The linkers used between the hemoglobin moiety and the chemotherapeutic agent (e.g. SMCC and EMCS) are substantially non-cleavable by hydrolysis and/or redox reaction under physiological conditions. FIG. 3 shows the LC-MS result for (A) hemoglobin, (B) Hb-SMCC-DM1 and Hb-EMCS-DM1, (C) Hb-SMCC-DM4 and Hb-EMCS-DM4, and (D) Hb-VcMMAE agents for targeting the cancer cells together with therapeutic effect in cancer treatment.

Figure 4:
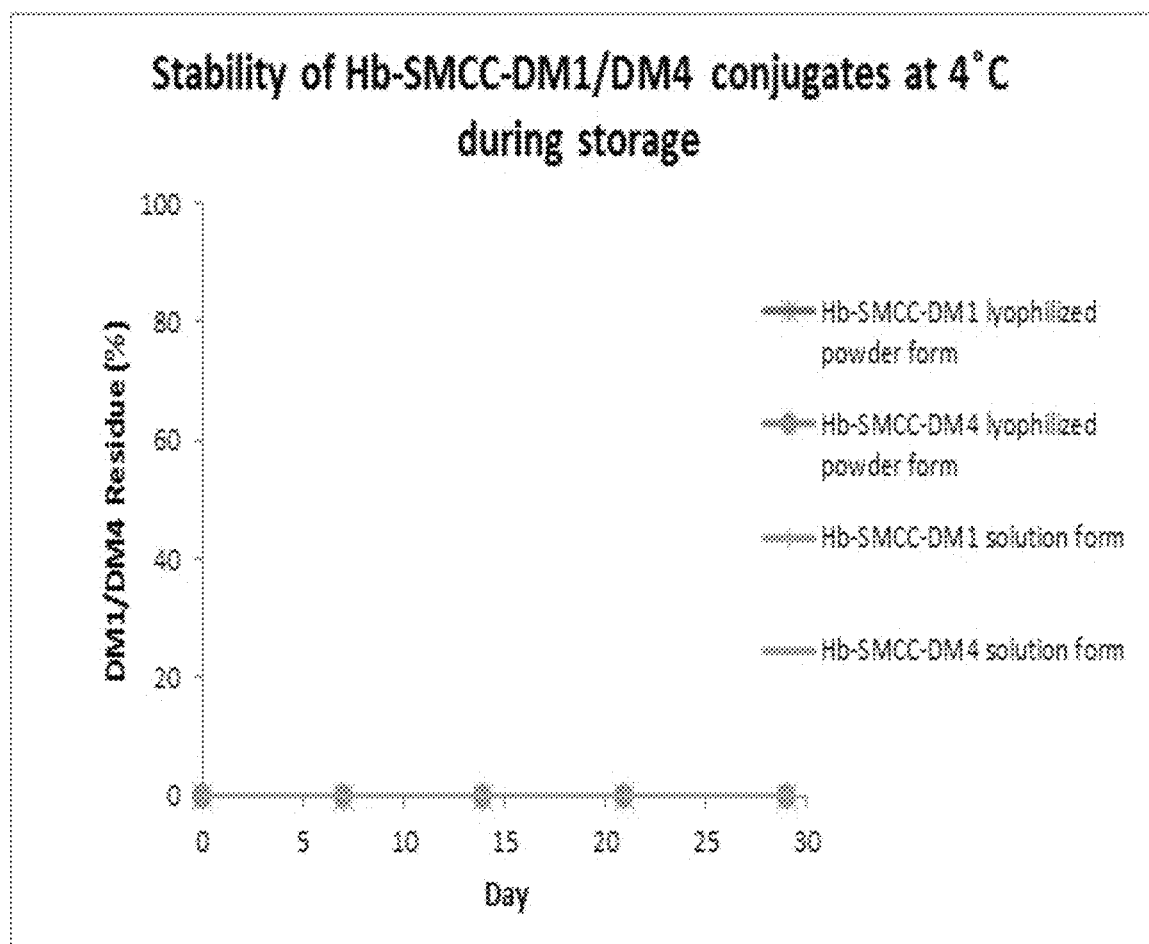
FIG. 4 shows the stability of Hb-SMCC-DM1 and Hb-SMCC-DM4 at 4° C. during storage in lyophilized powder form and solution form.

The stability of Hb-SMCC-DM1 and Hb-SMCC-DM4 at 4° C. during storage in lyophilized powder form and solution form is shown in FIG. 4. Free DM1 and DM4 was not observed by UPLC analysis of Hb-SMCC-DM1 and Hb-SMCC-DM4 (FIG. 4), indicating that Hb-SMCC-DM1 and Hb-SMCC-DM4 are stable at 4° C. during storage in lyophilized powder form and solution form.

Figures 5C, 6A:
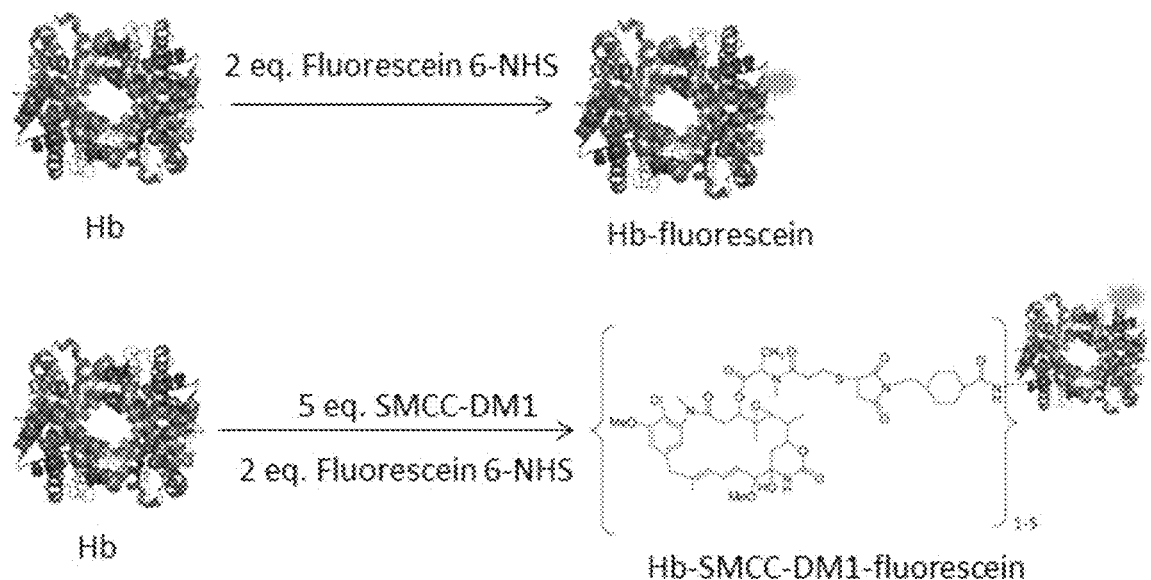
FIG. 5C shows the efficacy (Cytotoxicity) of hemoglobin-based cytotoxic agents with different MDR in liver cancer cell lines, pancreatic cancer cell lines, and colon cancer cell lines in vitro.
FIG. 6A shows the conjugation scheme for hemoglobin-based therapeutic agents with fluorescent dye fluorescein in accordance with certain embodiments described herein.

The captioned (A) Hb-SMCC-DM1 and Hb-EMCS-DM1, (B) Hb-SMCC-DM4 and Hb-EMCS-DM4, and (B) Hb-VcMMAE, ability in killing cancer cells are exemplified in various in vitro models. By employing the MTT assay, the cytotoxicity of these conjugates on various cancer cells was determined with IC50 values (FIG. 5A) toward liver cancer cell lines, leukemia (AML) cell lines, acute lymphocytic leukemia cell lines, pancreatic cancer cell lines, colon cancer cell lines, lymphoma NK cell lines, melanoma cell lines, and breast cancer cell lines respectively. In contrast, unconjugated hemoglobin displayed poor cytotoxic effect (IC50>10 µM), indicating that conversion of hemoglobin into hemoglobin-based DM1/DM4/MMAE conjugates greatly enhances cancer cell killing power. In addition, the captioned Hb-SMCC-DM1 with higher MDR displayed better cytotoxic effect (FIG. 5C).

Figure 6B:
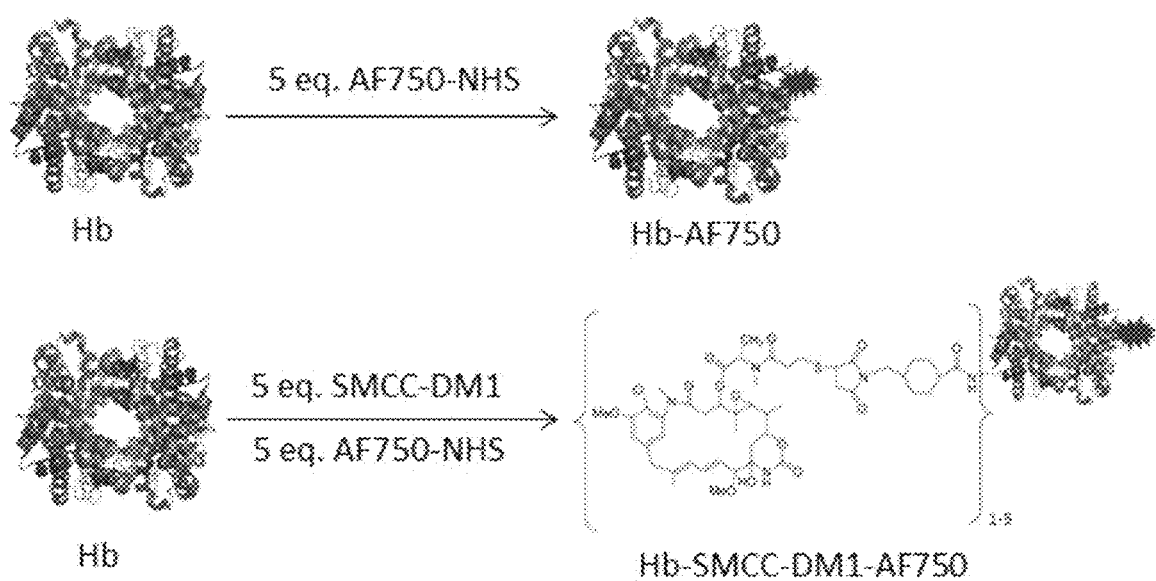
FIG. 6B shows the conjugation scheme for hemoglobin-based therapeutic agents with fluorescent dye Alexa Fluor 750 in accordance with certain embodiments described herein.
Figure 7A:
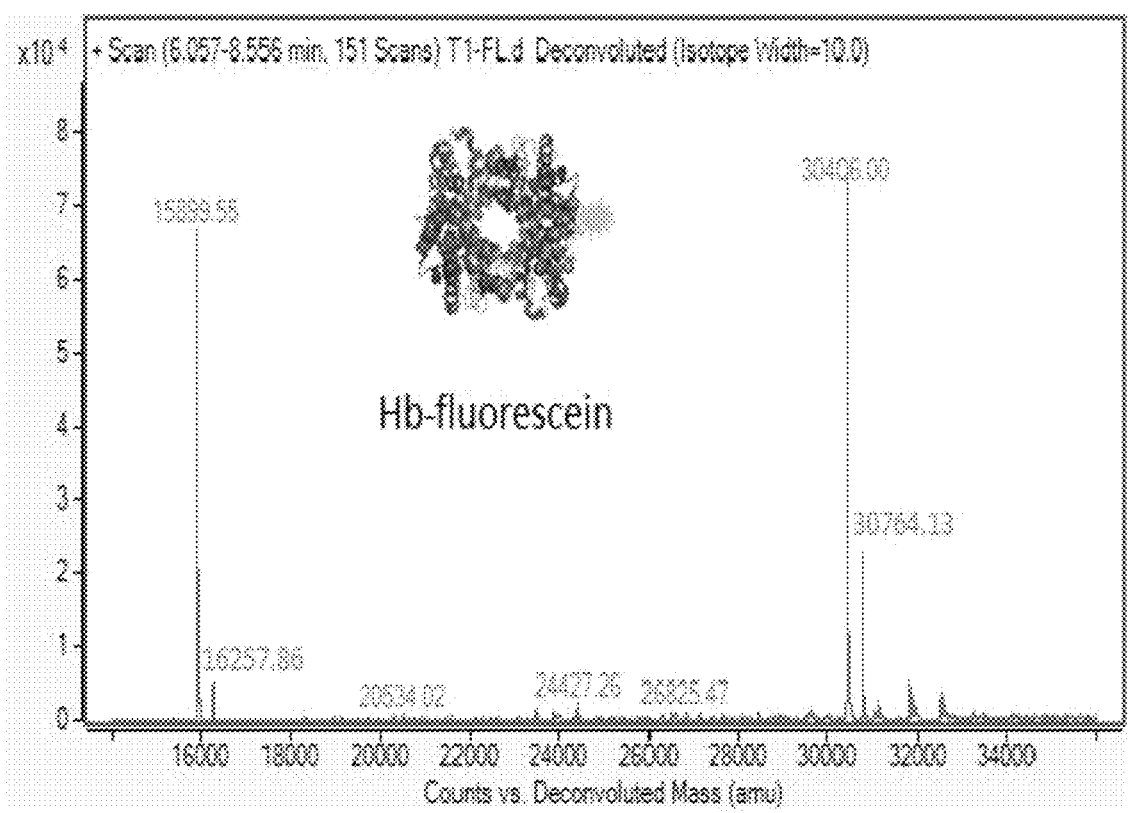
FIG. 7A shows the LC-MS results for Hb-fluorescein.
Figure 7B:
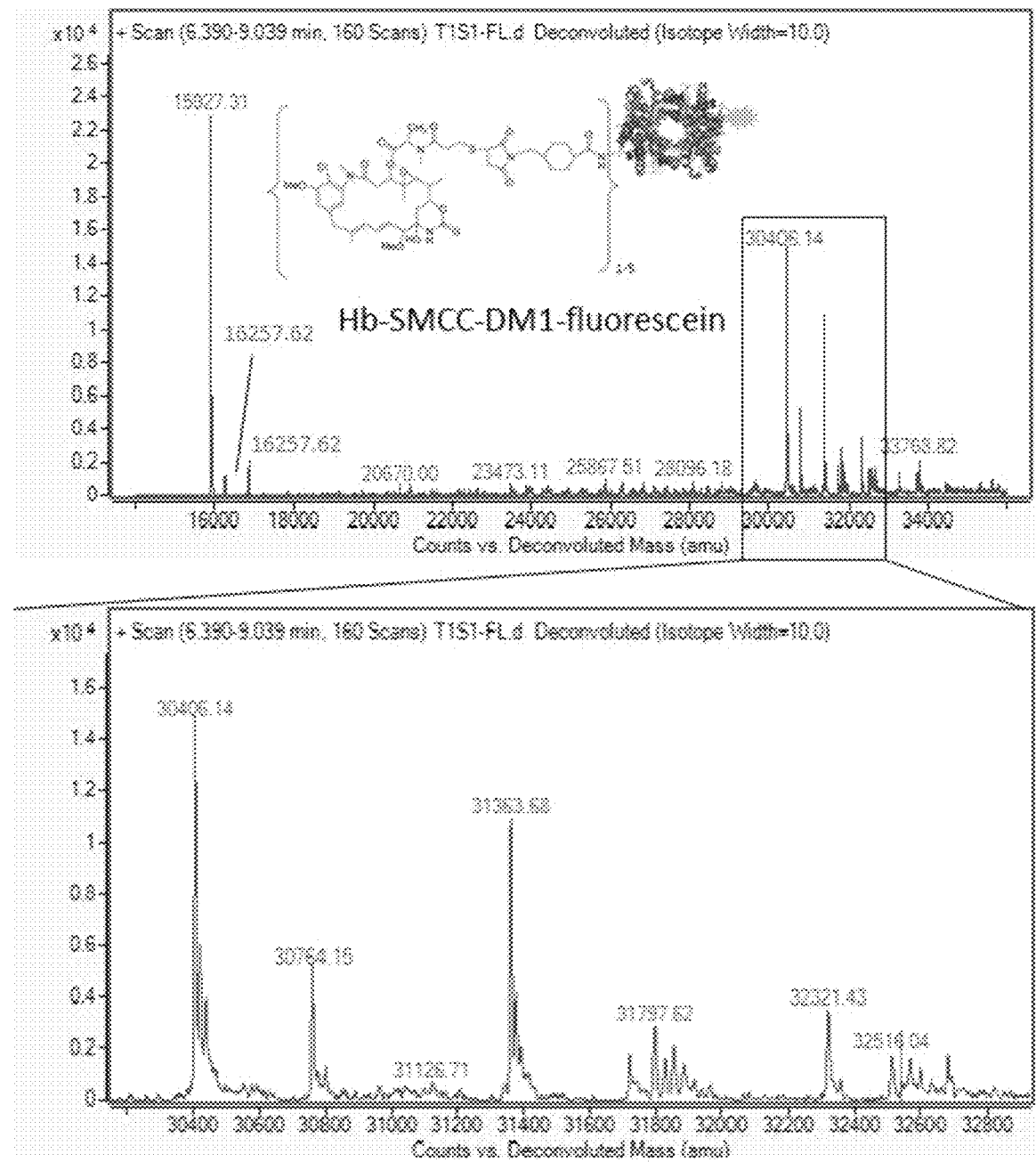
FIG. 7B shows the LC-MS results for Hb-SMCC-DM-fluorescein conjugate.
Figure 7C:
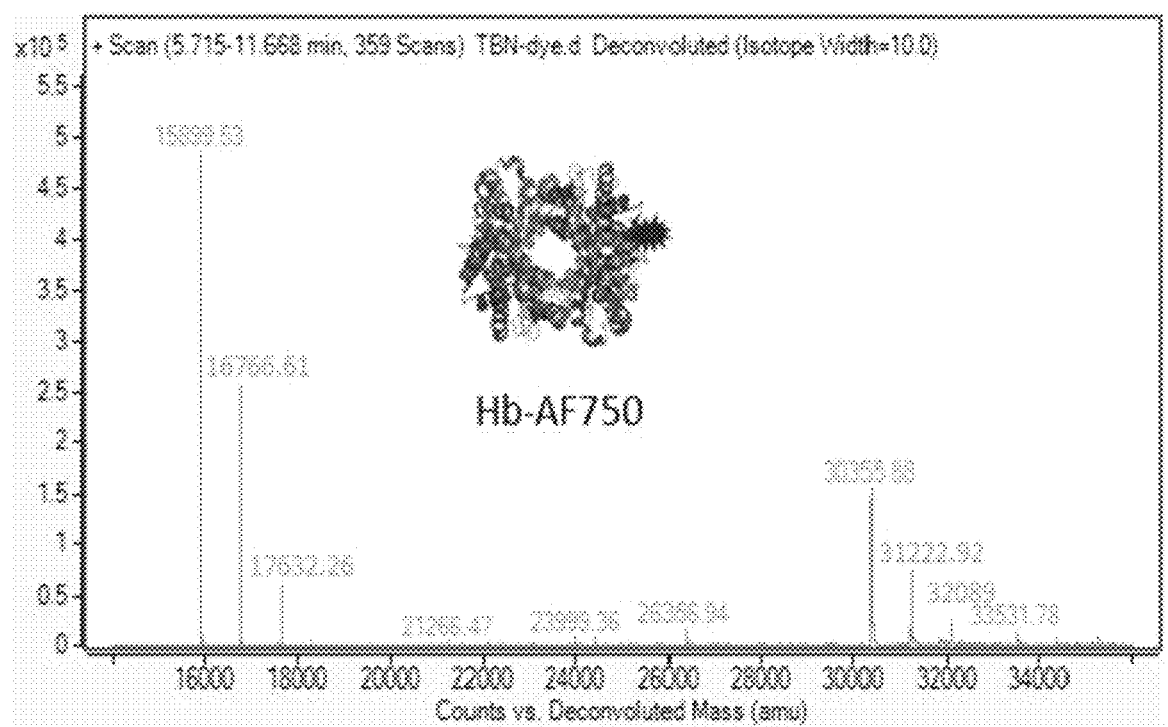
FIG. 7C shows the LC-MS results for Hb-AF750.
Figure 7D:
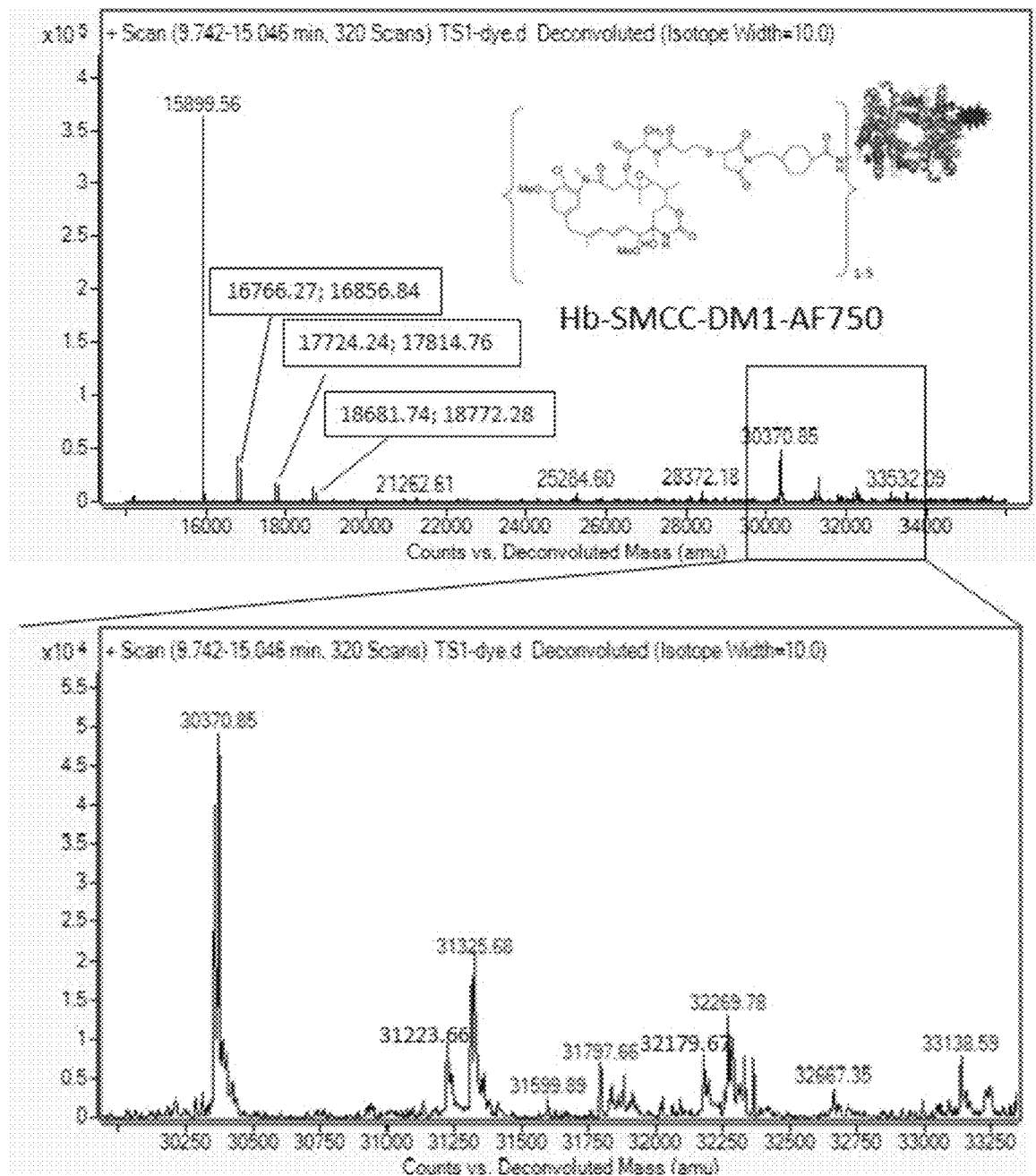
FIG. 7D shows the LC-MS results for Hb-SMCC-DM1-AF750 conjugate.

FIG. 6 shows the conjugation scheme of (A) Hb-fluorescein, (B) Hb-SMCC-DM1-fluorescein, (C) hemoglobin Hb-AF750, and (D) Hb-SMCC-DM1-AF750. FIG. 7 illustrates that fluorescent dyes (e.g. fluorescein 6-carboxysuccinimidyl ester (F-6-NHS) and Alexa Fluo 750 (AF750)) can be successfully linked to a molecule of hemoglobin even with cytotoxic agents DM1.

The fluorescein-labeled hemoglobin can enter into the cancer cells (e.g., liver cancer cells) and the result is illustrated in FIG. 8. It is expected that the modified hemoglobin-based cytotoxic agent can also kill the cancer cells effectively. Live cell imaging can be employed in the present application to monitor the uptake of various forms of Hb-SMCC-DM1 into the cancer cells. Breast cancer cell 4T1 (FIG. 8A), Colon cancer cell HCT116 (FIG. 8B), and Liver cancer cell SMMC7721 (FIG. 8C), are exposed to 0.01 mg/mL for 45 min prior to live cell acquisition. Hb-SMCC-DM1 is observed to be uptaken into the cytoplasm of the cancer cells after 45 min of exposure. The time lapse for 24 h of exposure is also performed (FIG. 8D). Cell death is observed from 6 h and most cells are dead at 24 h.

Figure 9A:
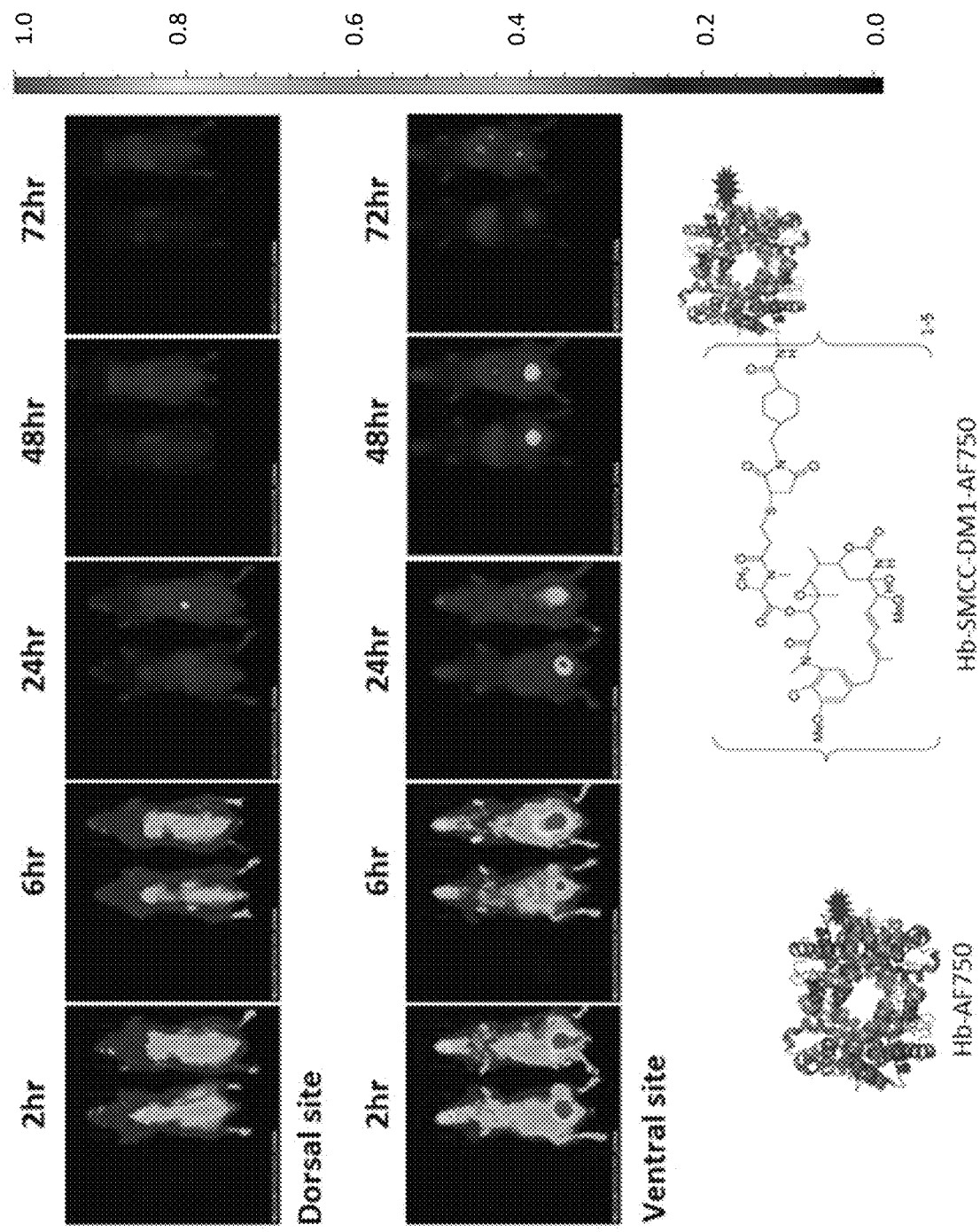
FIG. 9A illustrates the biodistribution of Hb-AF750 and Hb-SMCC-DM1-AF750 conjugate in normal mice.
Figure 9B:
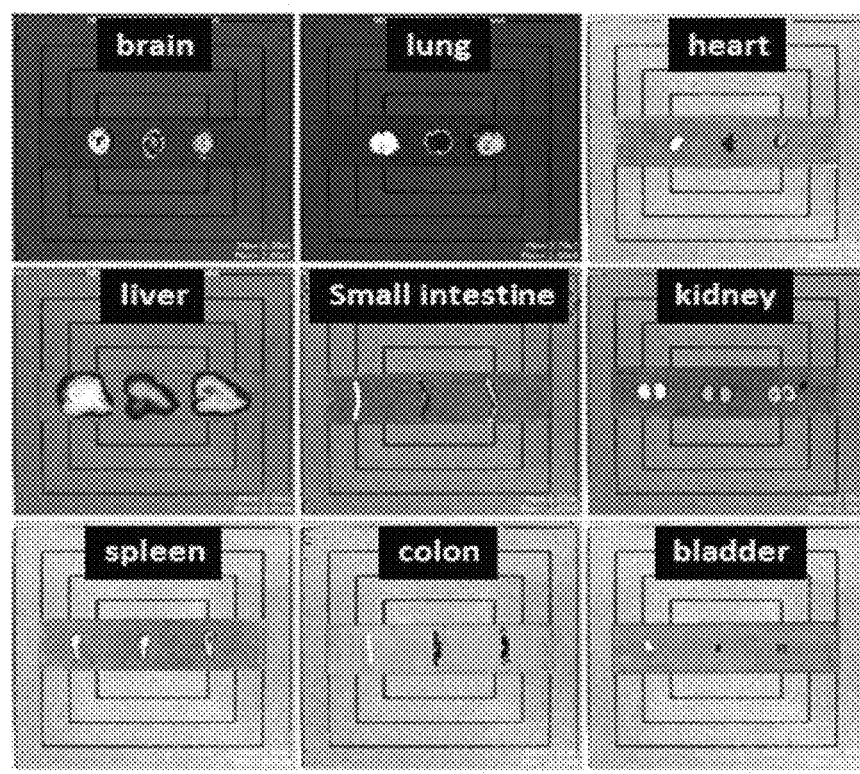
FIG. 9B illustrates the biodistribution of Hb-AF750 and Hb-SMCC-DM1-AF750 conjugate in various kinds of organs collected from sacrificed mice.
Figure 9B:
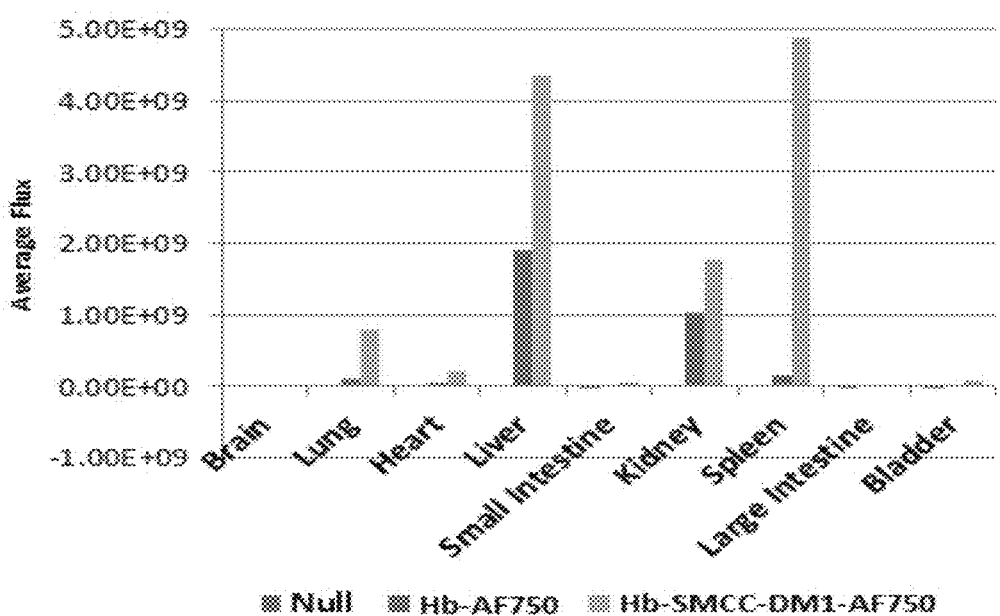

The biodistribution of AF750-labeled hemoglobin is performed for 72 h on normal mouse model and the result is illustrated in FIG. 9. The fluorescence signal of hemoglobin is observed mainly in liver and kidney at 72 h post-injection, and for Hb-SMCC-DM1 mainly in liver and spleen in FIG. 9B.

Figure 10A:
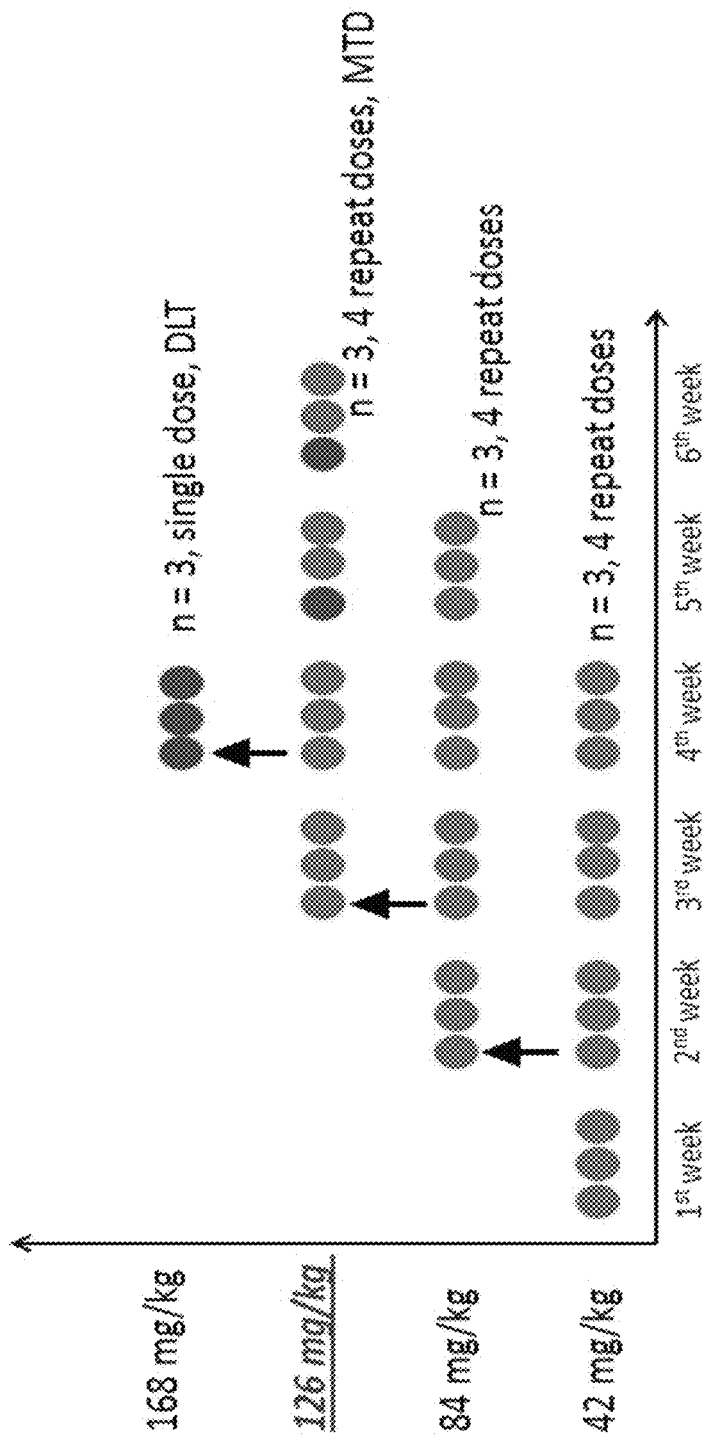
FIG. 10A illustrates the toxicity of Hb-SMCC-DM1 by dose escalation model.
Figure 10B:
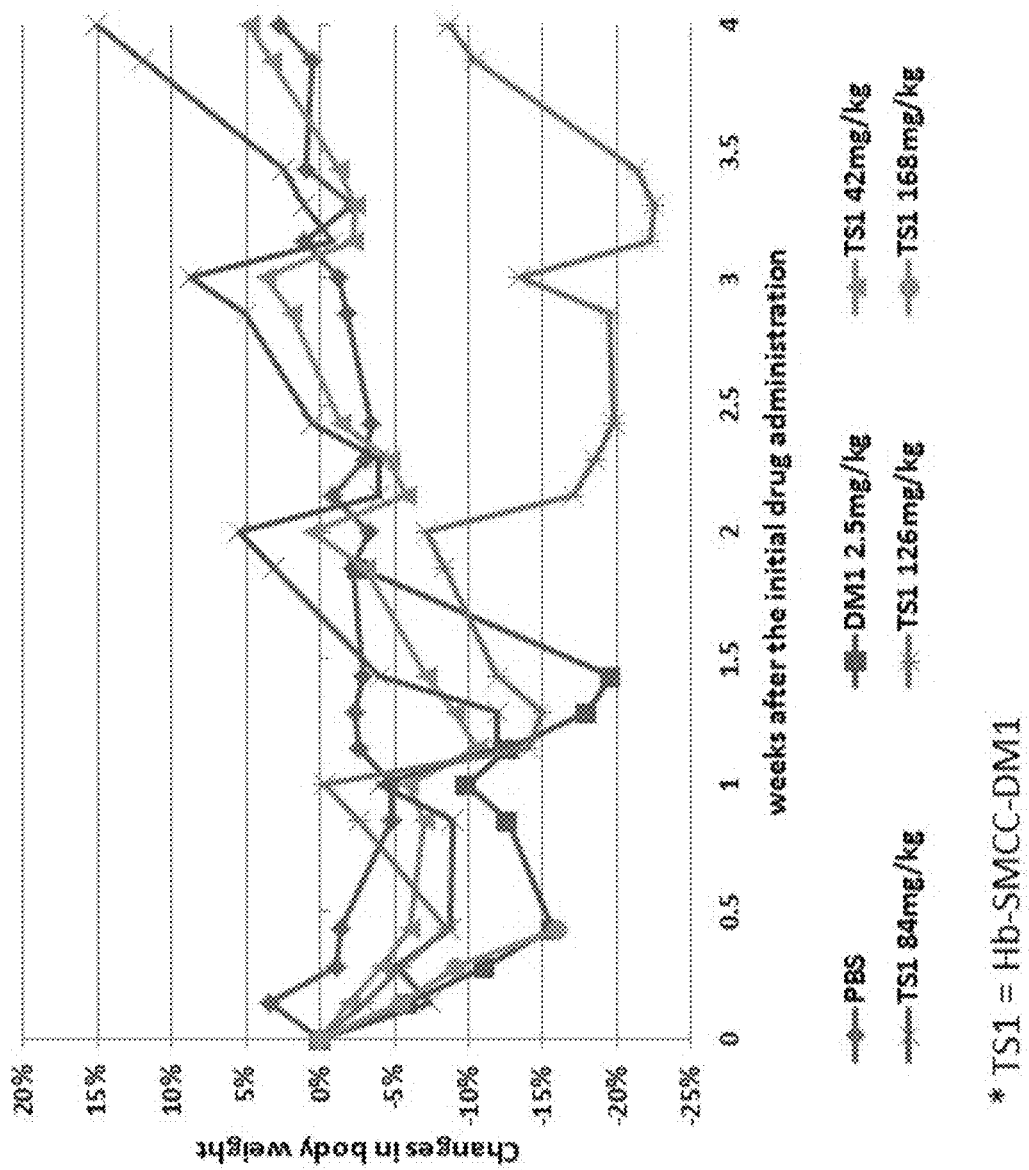
FIG. 10B illustrates the toxicity of Hb-SMCC-DM1 by the body weight change of mice with different dosage injections.

The therapeutic premise of Hb-SMCC-DM1 based on the hypothesis that target delivery of potent cytotoxic drugs to tumors will provide better tolerability and efficacy compared with non-targeted delivery, where poor tolerability can limit efficacious doses. Preliminary toxicity studies in normal mice are presented for Hb-SMCC-DM1, including limited assessment of unconjugated DM1. Hb-SMCC-DM1-DM1 is well tolerated at doses up to 126 mg/kg (~7.5 mg/kg DM1) (FIG. 10). In contrast, unconjugated-DM1 was only tolerated up to 2.5 mg/kg. This suggests that around two-fold higher doses of the cytotoxic agent are tolerated in Hb-SMCC-DM1, supporting the premise that Hb-SMCC-DM1 exhibits improved toxicity as compared with DM1.

Figure 11A:
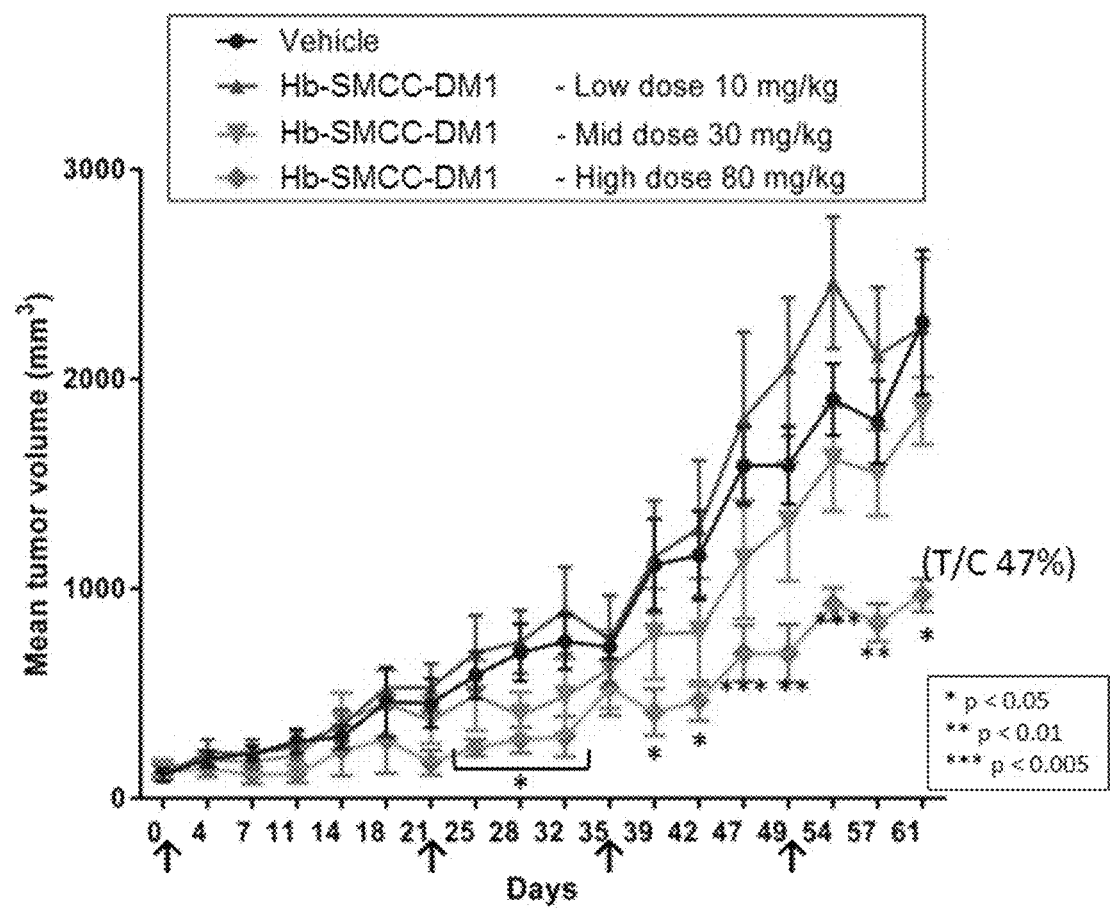
FIG. 11A shows the efficacy (anti-tumor growth) of hemoglobin-based cytotoxic agents in colorectal cancer HCT116 xenograft nude mice model in vivo.
Figure 11B:
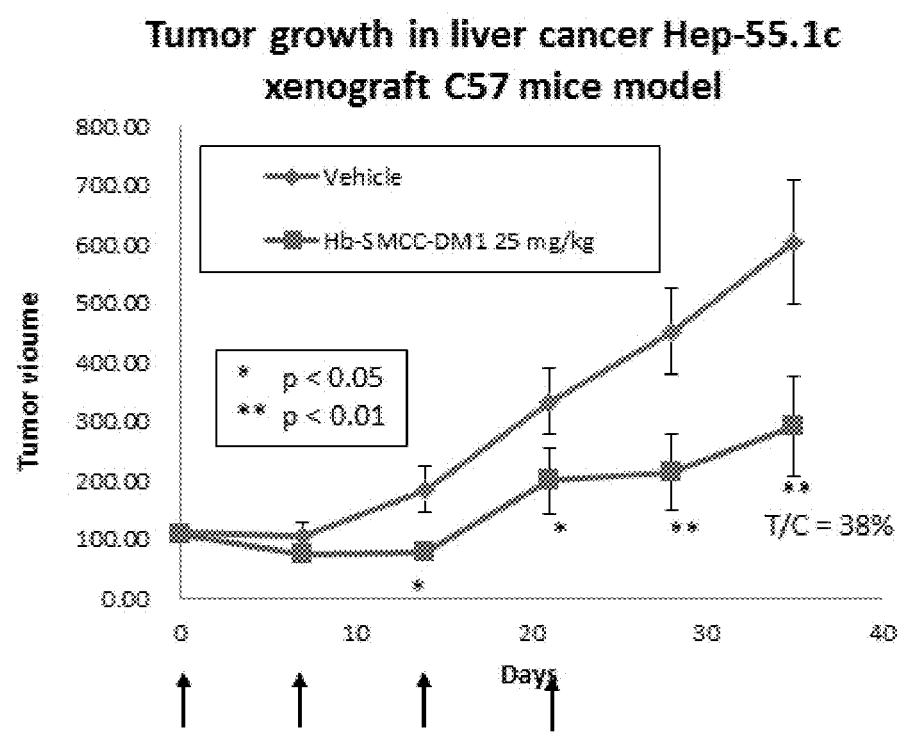
FIG. 11B shows the efficacy (anti-tumor growth) of hemoglobin-based cytotoxic agents in liver cancer Hep-55.1c xenograft C57 mice model in vivo.
Figure 11C:
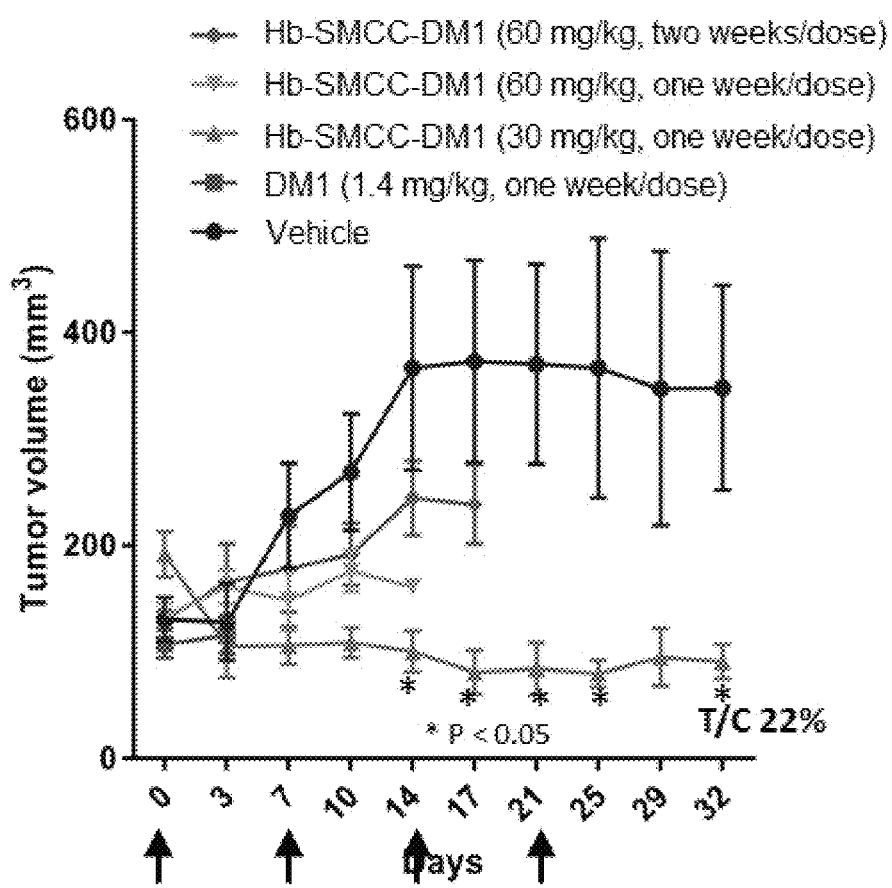
FIG. 11C shows the efficacy (anti-tumor growth) of hemoglobin-based cytotoxic agents in pancreatic cancer Mia PaCa-2 xenograft nude mice model in vivo.

The efficacy studies (anti-tumor activity) of Hb-SMCC-DM1 in colorectal cancer HCT116 xenograft nude mice model, liver cancer Hep-55.1c xenograft C57 mice model, and pancreatic cancer Mia PaCa-2 xenograft nude mice model are performed and the result is showed in FIG. 11A, FIG. 11B, and FIG. 11C. The tumor volume was suppressed significantly in these models, even up to 22% in pancreatic cancer Mia PaCa-2 xenograft nude mice model, indicating therapeutic premise of Hb-SMCC-DM1 provide better tolerability and efficacy compared with DM1.

The conditions for modification of hemoglobin-based therapeutic agents by two-step method were optimized for different parameters, such as drug stoichiometry, protein concentration, and reaction time. FIG. 12 shows the conversion and MDR of Hb-SMCC-DM1, Hb-EMCS-DM1, Hb-SMCC-DM4, and Hb-EMCS-DM4 under different conditions. The preferred condition for chemical modification of crosslinked hemoglobin is 100 mg/mL of hemoglobin with 10 eq. of linker at pH 7.8 in the first step and 10 mg/mL of hemoglobin-linker with 4 eq. of DM1 or DM4 at pH 7.8 in the second step.

The conditions for modification of hemoglobin-based therapeutic agents by one-step method were optimized for different parameters, such as drug stoichiometry, protein concentration, and reaction time. FIG. 13 shows the conversion and MDR of Hb-SMCC-DM1 under different conditions. The preferred condition for chemical modification of crosslinked hemoglobin is 10 mg/mL of hemoglobin with 5 eq. of SMCC-DM1 at pH 7.8 for 20 h.

FIG. 14 shows the conversion and MDR of Hb-VcMMAE under different conditions. The preferred condition for chemical modification of crosslinked hemoglobin is 10 mg/mL of hemoglobin with 4 eq. of VcMMAE in dimethylacetamide (DMA) at pH 7.8 for 20 hrs.

Hemoglobin has oxygen transport properties and it can target cancerous cells or tissues in a human or animal body. In certain embodiments, a reducing agent, e.g. sodium dithionite, is utilized to reduce redox potential in aqueous solution and reduce oxygenated hemoglobin to deoxygenated hemoglobin, which will retain the oxygen transport feature of hemoglobin to alleviate the hypoxic condition.

EXAMPLES

The following examples are provided by way of describing specific embodiments of this disclosure without intending to limit the scope of this invention in any way.

Example 1—Preparation of Hemoglobin $2\alpha\beta_2$ (TBM1)

TBM1 was prepared according to the procedure described in U.S. patent application Ser. No. 16/777,932.

Example 2—Modification of Hemoglobin with SMCC and DM1 by Two-Step Method

A 1 mL solution of TBM1 (10 g/dL, 1.56 mM, pH 7.8) is added with 50 µL of SMCC (10 equivalents) in DMSO (dimethyl sulfoxide). The reaction solution is stirred at room temperature for 2 h, followed by purification using PD-10 desalting column and characterization by LC-MS. The estimated conversion yield of Hb-SMCC is 100%. About 6 molecules of SMCC are conjugated onto one molecule of modified hemoglobin. The purified Hb-SMCC is diluted to 10 mg/mL. 50 µL of DM1 (5 equivalents) in DMSO is added into 1 mL of Hb-SMCC (10 mg/mL) and stirred at room temperature for 20 h, followed by purification using PD-10 desalting column and characterization by LC-MS. The estimated conversion yield of Hb-SMCC-DM1 is 100%. About 3 molecules of DM1 are conjugated onto one molecule of hemoglobin.

Example 3—Modification of Hemoglobin with SMCC-DM1 by One-Step Method

A 1 mL solution of TBM1 (5 mg/mL, pH 7.8) is added with 50 µL of SMCC-DM1 (5 molar equivalents relative to the hemoglobin) in DMSO (dimethyl sulfoxide). The reaction solution is stirred at room temperature for 20 h, followed by purification using PD-10 desalting column and characterization by LC-MS. The estimated conversion yield of Hb-SMCC-DM1 is 87%. About 4.6 molecules of DM1 are conjugated onto one molecule of hemoglobin.

Example 4—Modification of Hemoglobin with VcMMAE by One-Step Method

A 1 mL solution of TBM1 (10 mg/mL, pH 7.8) is added with 50 µL of VcMMAE (4 equivalents) in DMA (dimethylacetamide). The reaction solution is stirred at room temperature for 20 h at room temperature, followed by purification using PD-10 desalting column and characterization by LC-MS. The estimated conversion yield of Hb-VcMMAE is 51%. About 1.3 molecules of MMAE are conjugated onto one molecule of hemoglobin.

Example 5—Synthesis of Hb-SMCC-DM1 Conjugate Using One-Step Method and Stability Studies in Solution and Lyophilized Forms 10% of sodium dithionite solution is prepared with deoxygenated phosphate buffer (100 mM, pH 8.0). 0.6 mL of the above sodium dithionite solution is added to 60 mL of TBM1 solution (5 mg/mL, pH 7.8), resulting hemoglobin solution with 0.1% of sodium dithionite. To the above hemoglobin solution is added 3 mL of SMCC-DM1 (5 molar equivalents) in DMSO (dimethyl sulfoxide). The reaction solution is stirred at room temperature for 20 h, followed by purification using TFF (tangential flow filtration) with 30 k membrane filter and characterization by ESI-MS. The estimated conversion yield of Hb-SMCC-DM1 is 87%. About 3 molecules of DM1 are conjugated onto one molecule of modified hemoglobin.

The purified conjugate is aliquoted into glass vial with 1 mL/vial. Half was frozen at −80° C. overnight and half stored at 4° C. The frozen products are lyophilized and then stored at −4° C. Stability tests of the products in solution form and lyophilized form are performed at interval times by UPLC (Ultra-performance liquid chromatography). The results of the stability tests are depicted in FIG. 4.

Example 6—Modification of Hemoglobin with Fluorescein 6-NHS and SMCC-DM1

A 1 mL of modified hemoglobin solution (5 mg/mL, pH 7.8) is added with 25 µL of fluorescein 6-NHS (2 equivalents) in DMSO and 25 µL of SMCC-DM1 (5 equivalents) in DMSO (dimethyl sulfoxide). The reaction solution is stirred at room temperature for 6 h, followed by purification using PD-10 desalting column and characterization by ESI-MS. About 0.3 molecules of DM1 and 1.7 molecules of fluorescein are conjugated onto one molecule of modified hemoglobin.

Example 7—Modification of Hemoglobin with AF750-NHS and SMCC-DM1

A 1 mL of modified hemoglobin solution (5 mg/mL, pH 7.8) is added with 25 µL of AF750-NHS (5 equivalents) in DMSO and 25 µL of SMCC-DM1 (5 equivalents) in DMSO (dimethyl sulfoxide). The reaction solution is stirred at room temperature for 6 h, followed by purification using PD-10 desalting column and characterization by ESI-MS. About 1.3 molecules of DM1 and 0.5 molecules of AF750 are conjugated onto one molecule of modified hemoglobin.

Example 8—Culture and Reagents for Different Cancer Cell Lines

Cancer cells are cultured in medium (Invitrogen) with 10% Fetal bovine serum (FBS), 100 U/mL penicillin and 100 µg/mL streptomycin at 37° C. For normoxic condition, cells are incubated with ambient $O_2$ concentration and 5% $CO_2$, for hypoxic condition, cells are incubated with 0.1-0.5% $O_2$ (Quorum FC-7 automatic $CO_2/O_2/N_2$ gas mixer) and 5% $CO_2$. Culture conditions for both adherent and non-adherent cancer cell lines used are comparable, including liver cancer cells HepG2 and SMMC7221, breast cancer cells 4T1, MCF7 and MDA-MB231, Colorectal carcinoma cells Colo205, HCT116 and HT29, Pancreatic cancer cells Panc-1, Mia PaCa-2, and Capan-1.

Example 9—Live Cell Time-Lapse Microscopy in Cancer Cells

Figure 8A:
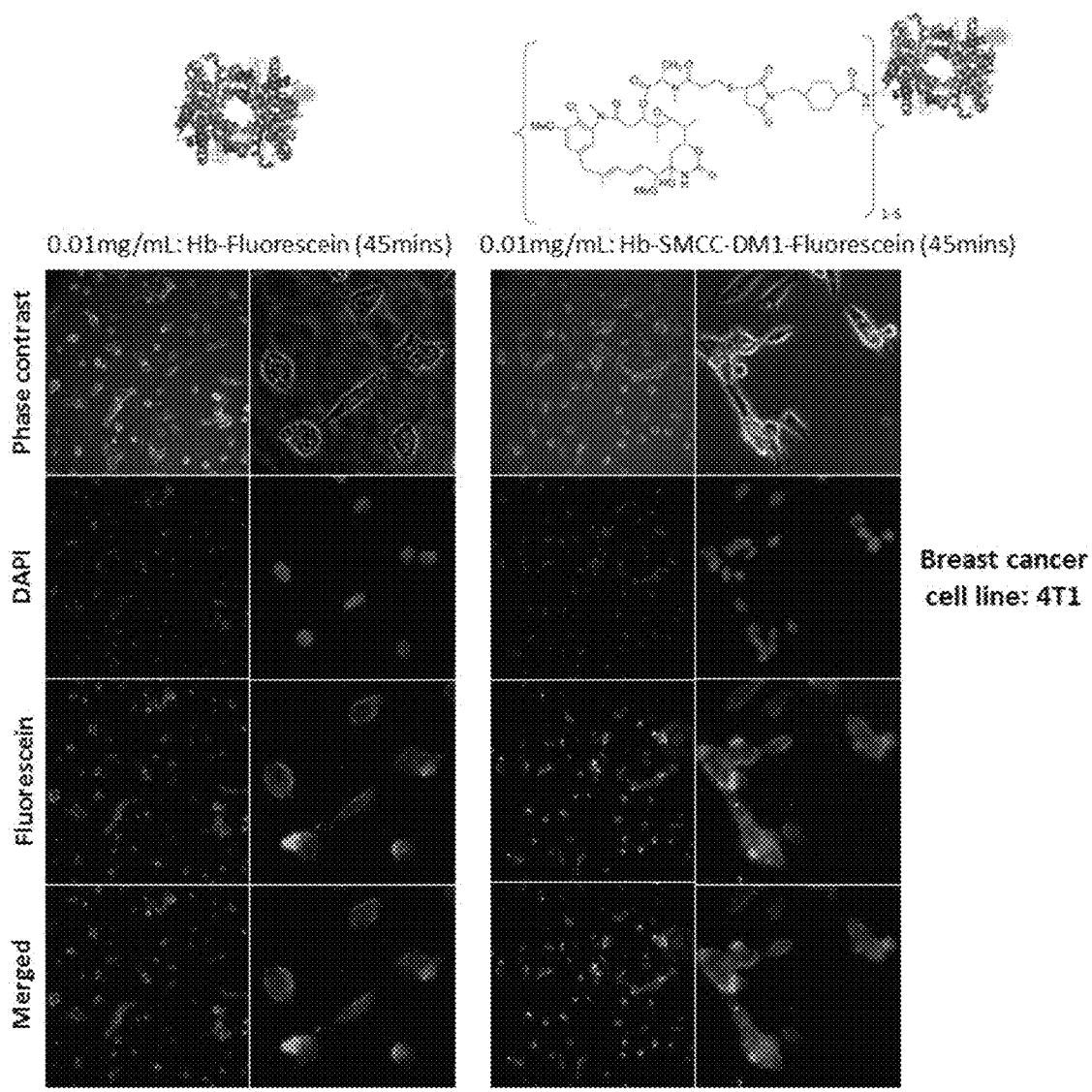
FIG. 8A illustrates that the fluorescein labeled modified hemoglobin Hb-fluorescein and Hb-SMCC-DM1-fluorescein conjugate can enter into breast cancer cells 4T1.
Figure 8B:
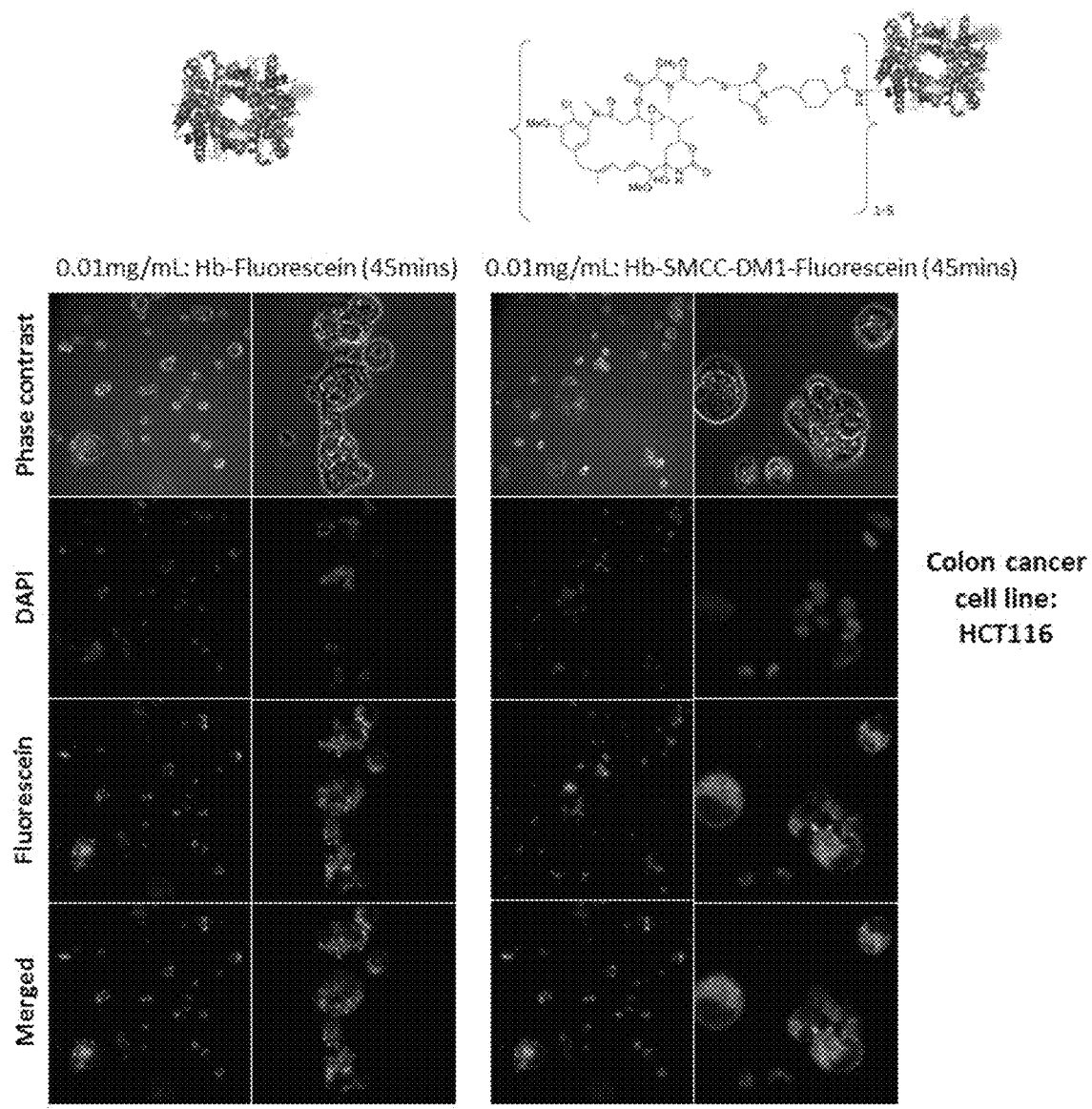
FIG. 8B illustrates that the fluorescein labeled modified hemoglobin Hb-fluorescein and Hb-SMCC-DM1-fluorescein conjugate can enter into colon cancer cells HCT116.
Figure 8C:
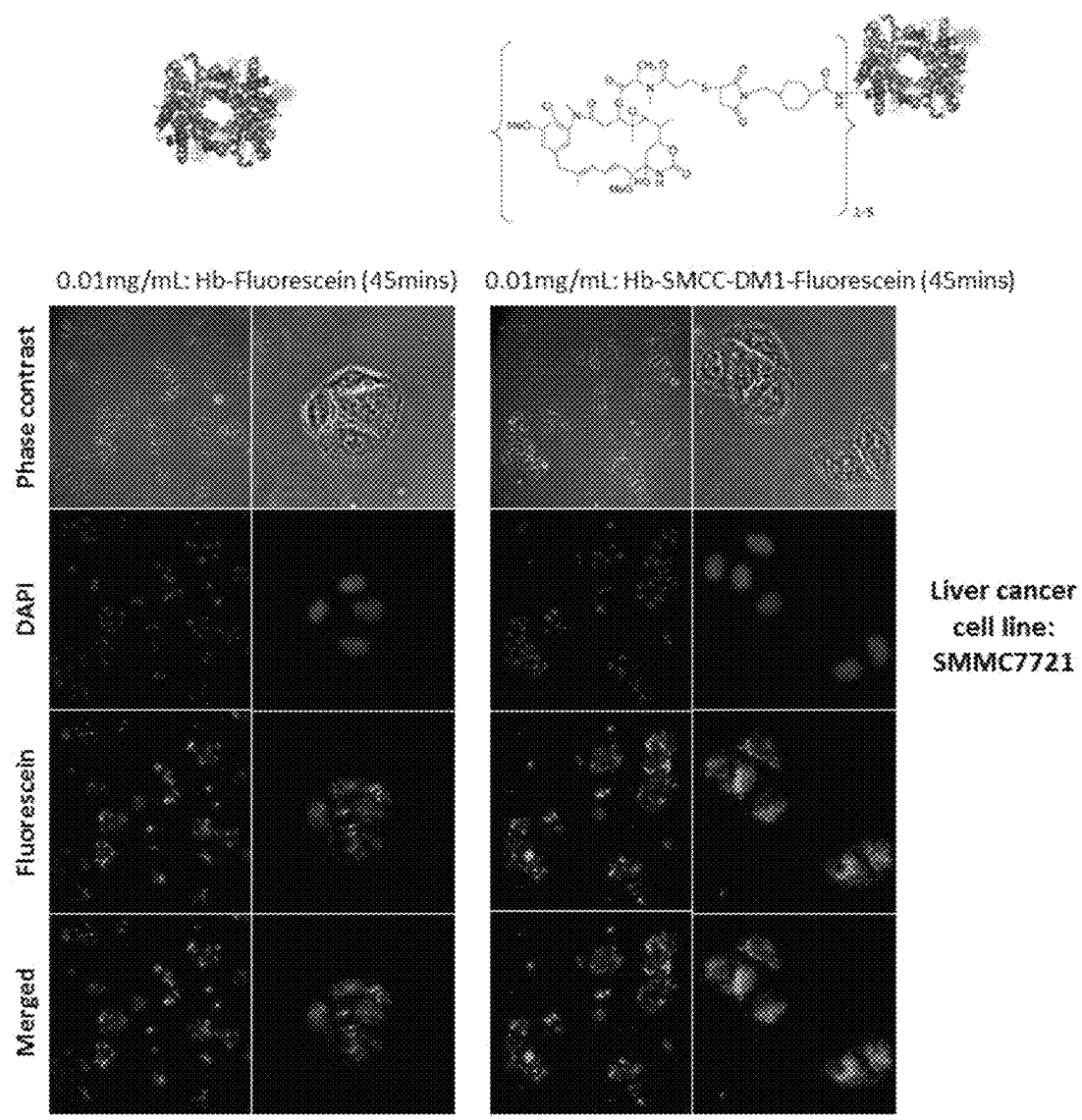
FIG. 8C illustrates that the fluorescein labeled modified hemoglobin Hb-fluorescein and Hb-SMCC-DM1-fluorescein conjugate can enter into liver cancer cells SMMC7721.
Figure 8D:
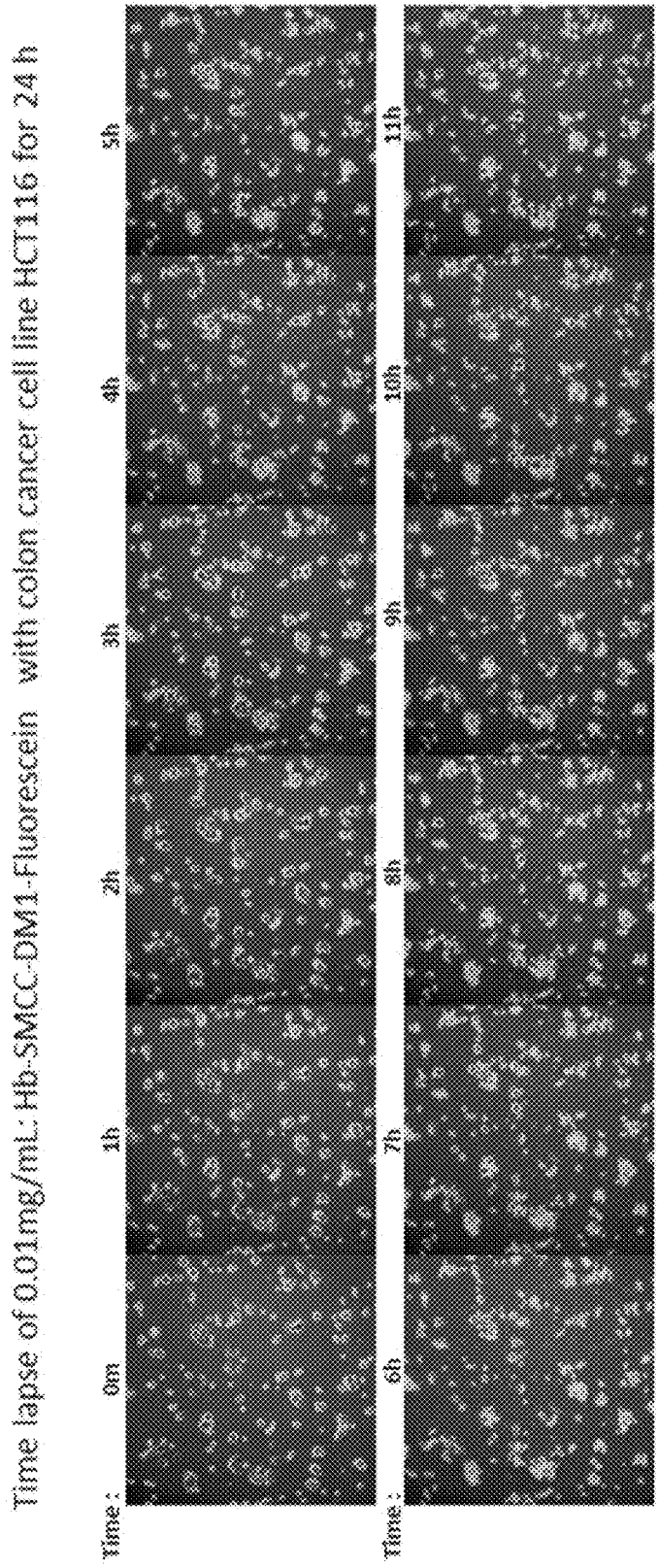
FIG. 8D illustrates that the fluorescein labeled modified hemoglobin Hb-fluorescein and Hb-SMCC-DM1-fluorescein conjugate can enter into colon cancer cells HCT116 and colon cancer cells HCT116 are observed dead when incubated with Hb-SMCC-DM1-fluorescein conjugate (0.01 mg/mL) from 6 h to 24 h.
Figure 8D:
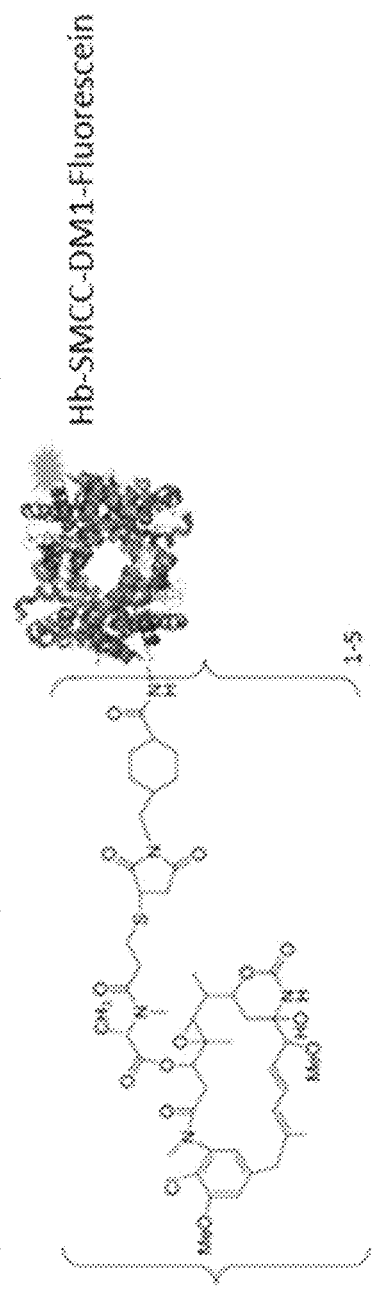
Figure 8D:
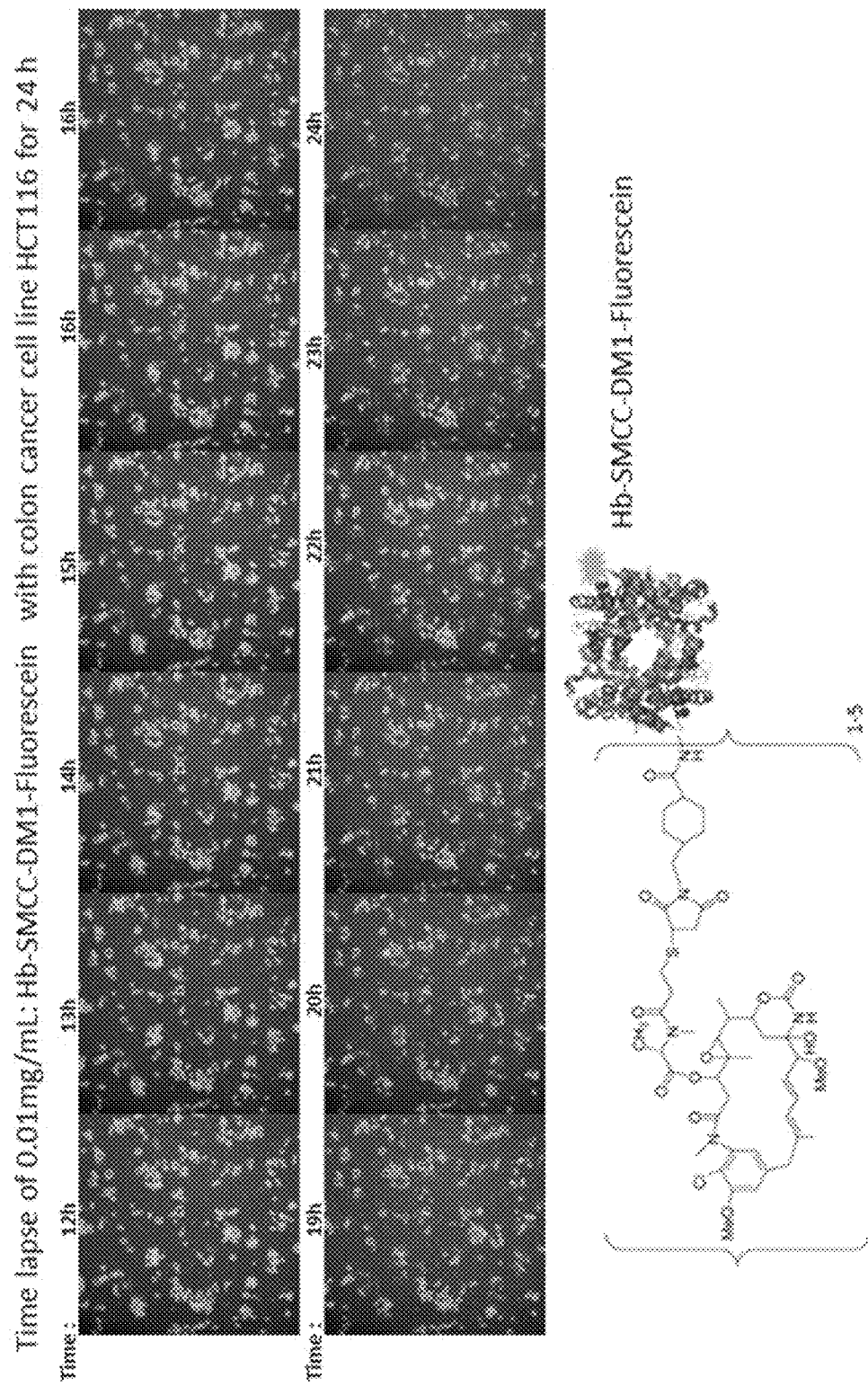

Cancer cells (e.g. HCT116 colorectal cancer cells) are seeded onto glass bottom microwell dishes (MatTek Corporation). Live cells at defined zooms (63×, 20×) are acquired using Zeiss Observer Z1 widefield microscope, equipped with atmospheric/temperature-controlled chamber and motorized stage for multi-positional acquisition. The incubation is performed in an enclosed live cell imaging system purged with 0.1% 02 and 5% $CO_2$ (premixed). Cells are exposed to (1) Hb-fluorescein and (2) Hb-SMCC-DM1-fluorescein for 45 min prior to the acquisition of images every 1 h for a period of 24 h. The images are shown in FIG. 8D.

Example 10—Cytotoxicity Assay on Cancer Cell Lines

Cell viability is measured using a 3-(4,5-dimethylthiazol-2-yl)-2,5-diphenyltetrazolium bromide (MTT) proliferation assay. Briefly, cancer cell lines (e.g. HCT116, 4T1, and SMMC7721) are seeded in a 96-well flat-bottomed microplate and cultured in 100 µL growth medium at 37° C. and 5% $CO_2$ for 24 h. Cell culture medium in each well is then replaced by 100 µL cell growth medium, containing either no drug, DM1 alone or modified hemoglobin-based cytotoxic agents at series concentrations. Incubation of drugs for 24 h, cell culture medium containing drugs is replaced by 100 µL MTT labeling reagent (1 mg/mL in PBS solution) in each well and incubation for further 4 h at 37° C. The medium is removed gently, and 50 µL DMSO is then added to each well as solubilizing agent to dissolve the formazan crystals completely. The absorbance at the wavelength of 570 nm is measured by iMark Microplate Absorbance Example 11—Biodistribution of Hb-SMCC-DM1 (MDR=3.0) in Normal Mice Biodistribution of Hb-SMCC-DM1 (Prepared using one-step method in Example 5, MDR of 3.0) in normal mice is performed by using normal mice model. Briefly, normal BALB/c mice are injected intravenously with 40 mg/kg of Hb-AF750 and Hb-SMCC-DM1-AF750, respectively, and imaged serially from 2 hour to 72 hour post-injection. The dorsal site and ventral site are both imaged as shown in FIG. 9A. The mice are sacrificed at 72 hour of drug administration to collect various kinds of organ for imaging.

Example 12—Preliminary Toxicity of Hb-SMCC-DM1 (MDR=3.0) in Normal Mice

The toxicity of Hb-SMCC-DM1 with an (Prepared using one-step method in Example 5, MDR of 3.0) is evaluated in repeat-dose study in normal BALB/c mice. Briefly, mice (n=3, females/group) are administered with unconjugated-DM1 and Hb-SMCC-DM1 weekly for a total of four IV doses at PBS, 2.5 mg/kg of unconjugated-DM1, and 42, 84, 126, and 168 mg/kg of Hb-SMCC-DM1, respectively. Body weights are recorded at every 3 days.

Example 13A—In Vivo Efficacy of Hb-SMCC-DM1 in Colorectal Cancer HCT116 Xenograft Nude Mice Model Naive female nude mice (4-6 weeks age) were inoculated in the right hind flank with 2 million of HCT116 tumor cells suspended in 50% phenol red-free Matrigel mixed with PBS buffer. All animals were randomly assigned into treatment groups, such that the mean tumor volume for each group was 100 to 200 mm$^3$. Hb, DM1 and Hb-SMCC-DM1 (Prepared using one-step method in Example 5, MDR of 3.0) were given by i.v. (10-20 mg/mL Hb-SMCC-DM, in 25 mM sodium phosphate at pH 8.5, formulated in 5% trehalose, w/v) injection once every week. Vehicle control was PBS. All treatment groups consisted of 6 animals per groups, and tumor size was monitored twice weekly using caliper measurement.

Example 13B—In Vivo Efficacy of Hb-SMCC-DM1 in Liver Cancer Hep-55.1c Xenograft C57 Mice Model Female C57 mice (4-6 weeks age) were inoculated in the right hind flank with tumor cells (5 million of Hep-55.1c) suspended in 50% phenol red-free Matrigel mixed with PBS buffer. All animals were randomly assigned into treatment groups, such that the mean tumor volume for each group was 100 to 200 mm$^3$. Hb-SMCC-DM1 (Prepared using one-step method in Example 5, MDR of 3.0) was given by i.v. (10-20 mg/mL Hb-SMCC-DM, in 25 mM sodium phosphate at pH 8.5, formulated in 5% trehalose, w/v) injection once every week. Vehicle control was PBS. All treatment groups consisted of 10 animals per groups, and tumor size was monitored twice weekly using caliper measurement.

Example 13C—In Vivo Efficacy of Hb-SMCC-DM1 (MDR=3.0) in Pancreatic Cancer Mia PaCa-2 Xenograft Nude Mice Model Naive female nude mice (4-6 weeks age) were inoculated in the right hind flank with 5 million of Mia PaCa-2 tumor cells suspended in 50% phenol red-free Matrigel mixed with PBS buffer. All animals were randomly assigned into treatment groups, such that the mean tumor volume for each group was 100 to 200 mm$^3$. Hb, DM1 and Hb-SMCC-DM1 (Prepared using one-step method in Example 5, MDR of 3.0) were given by i.v. (10-20 mg/mL Hb-SMCC-DM, in 25 mM sodium phosphate at pH 8.5, formulated in 5% trehalose, w/v) injection once every week. Vehicle control was PBS. All treatment groups consisted of 6 animals per groups, and tumor size was monitored twice weekly using caliper measurement.

What is claimed is:

1. A hemoglobin-based therapeutic agent comprising a hemoglobin and a chemotherapeutic agent selected from the group consisting of maytansinoid, an auristatin, and a calicheamicin, wherein the chemotherapeutic agent is covalently attached to the hemoglobin via a linker, and wherein the linker has the Formula 1:

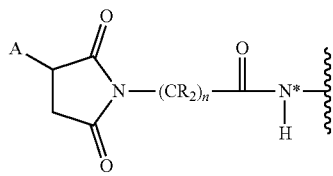

the linker has the Formula 2:

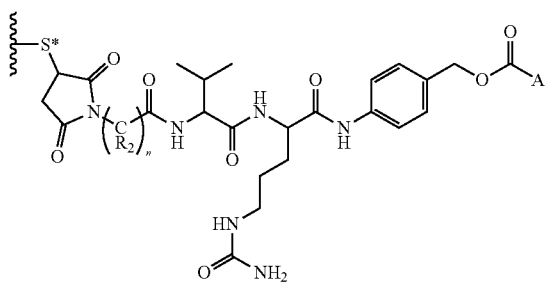

wherein A is the chemotherapeutic;
N* represents a nitrogen in a lysine side chain in the hemoglobin or a N-terminal amine in the hemoglobin;
S* represents a sulfur in a cysteine side chain in the hemoglobin; n is a whole number selected from 1-10; and
each R is hydrogen; or two R taken together with the carbons to which they are attached form a 3-7 membered cycloalkane and each remaining R is hydrogen.

2. The hemoglobin-based therapeutic agent of claim 1, wherein the hemoglobin is selected from the group consisting of bovine hemoglobin, human hemoglobin, canine hemoglobin, porcine hemoglobin, equine hemoglobin, recombinant hemoglobin and a subunit thereof.

3. The hemoglobin-based therapeutic agent of claim 1, wherein the hemoglobin comprises a di-alpha chain and two beta chains, wherein the di-alpha chain comprises a polypeptide sequence having at least 98.93% sequence homology with SEQ ID NO: 1, wherein the amino acids at position 1 and position 143 of SEQ ID NO: 1 must be methionine, the amino acids at position 29 and position 171 of SEQ ID NO: 1 must be phenylalanine, and the amino acids at position 58 and position 200 of SEQ ID NO: 1 must be glutamine; and the each of the two beta chains comprises a polypeptide sequence having at least 97.94% sequence homology with SEQ ID NO: 2, wherein the amino acid at position 1 must be methionine.

4. The hemoglobin-based therapeutic agent of claim 1, wherein the molar drug ratio (MDR) of the hemoglobin-based therapeutic agent is between 1.0-5.0.

5. The hemoglobin-based therapeutic agent of claim 1, wherein the chemotherapeutic agent is selected from the group consisting of mertansine (DM1), ravtansine (DM4), and monomethylauristatin E (MMAE).

6. The hemoglobin-based therapeutic agent of claim 1, wherein n is a whole number between 2-6 and each R is hydrogen; or n is a whole number between 4-6; two R taken together with the carbons to which they are attached form a 4-6 membered cycloalkane and each remaining R is hydrogen.

7. The hemoglobin-based therapeutic agent of claim 1, wherein the hemoglobin-based therapeutic agent is selected from the group consisting of:

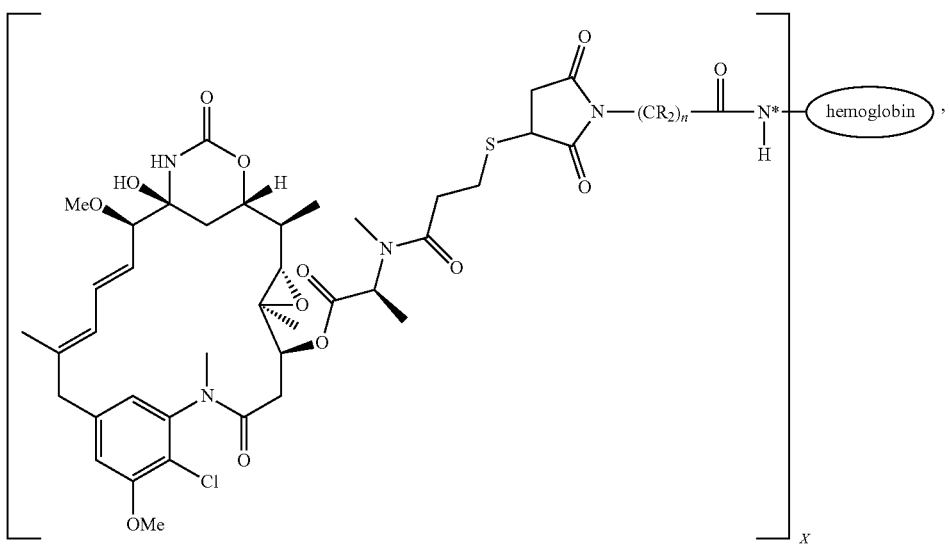

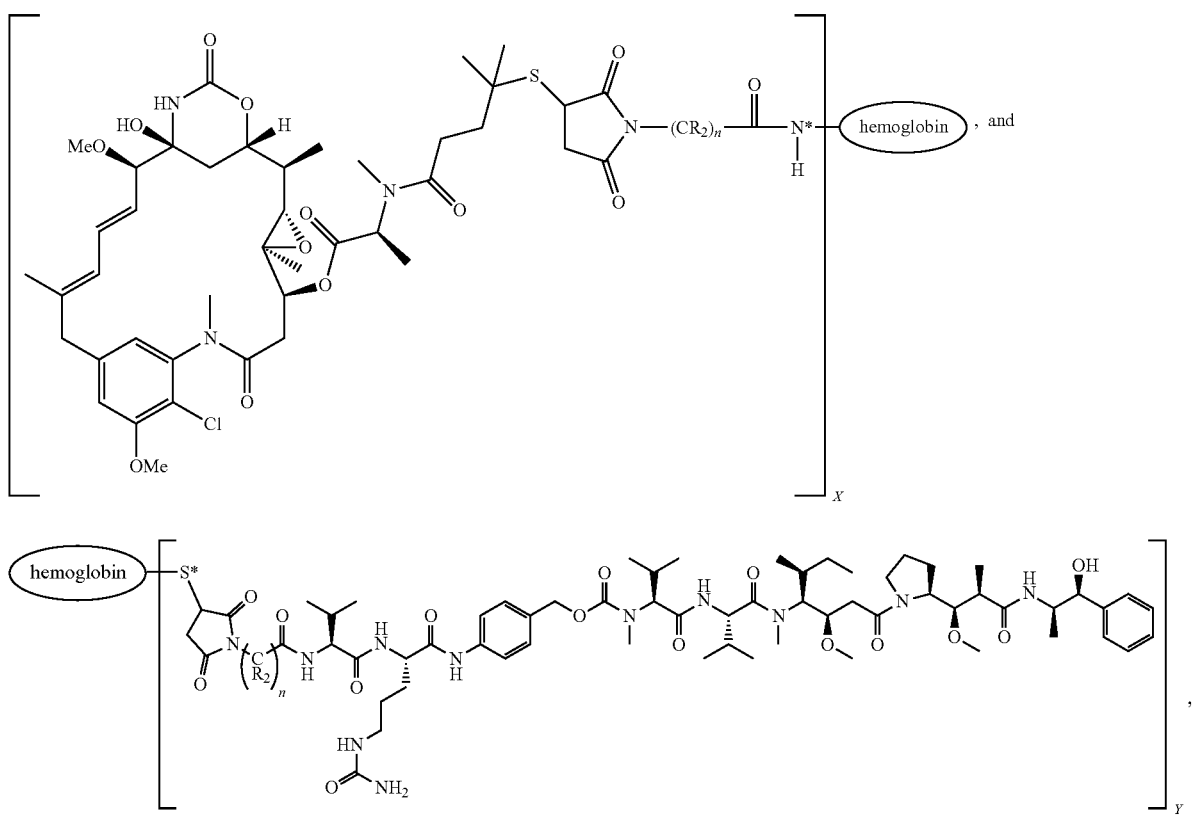

wherein each N* independently represents a nitrogen in a lysine side chain in the hemoglobin or a N-terminal amine in the hemoglobin;

S* independently represents a sulfur in a cysteine side chain in the hemoglobin;

n is a whole number between 1-10;

each R is hydrogen; or two R taken together with the carbons to which they are attached form a 3-7 membered cycloalkane and each remaining R is hydrogen;

X is the MDR of the hemoglobin-based therapeutic agent, wherein X has a value between 1.0-5.0; and Y is the MDR of the hemoglobin-based therapeutic agent, wherein Y has a value between 1.0-2.0.

8. The hemoglobin-based therapeutic agent of claim 1, wherein the hemoglobin-based therapeutic agent is selected from the group consisting of:

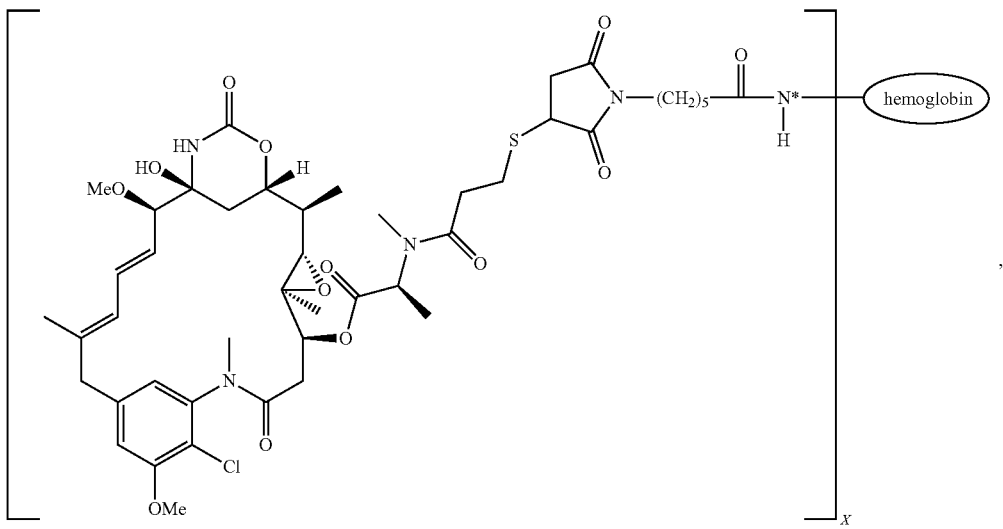

-continued
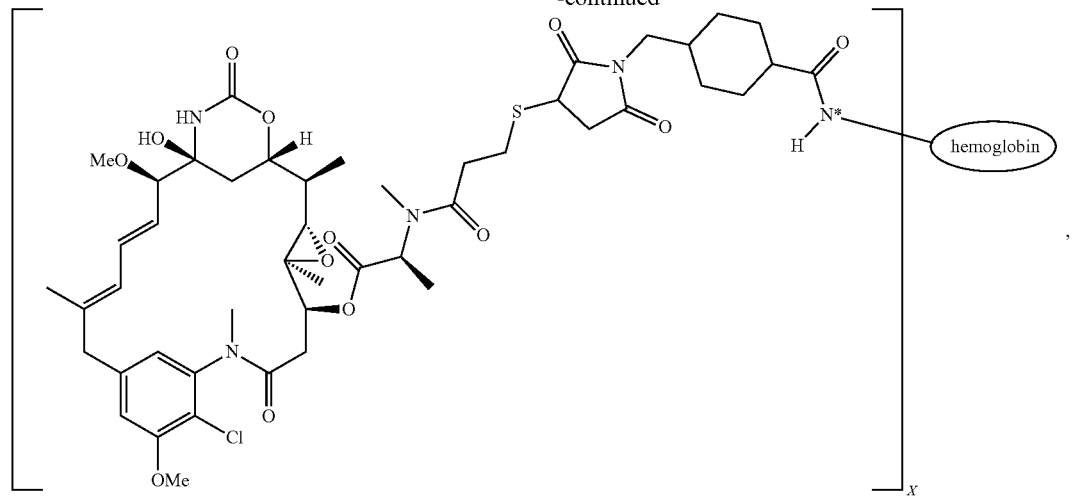
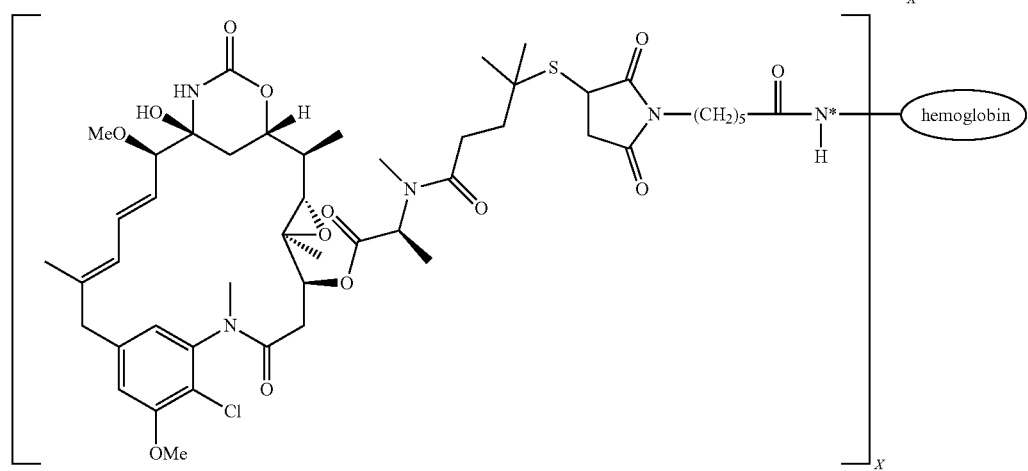
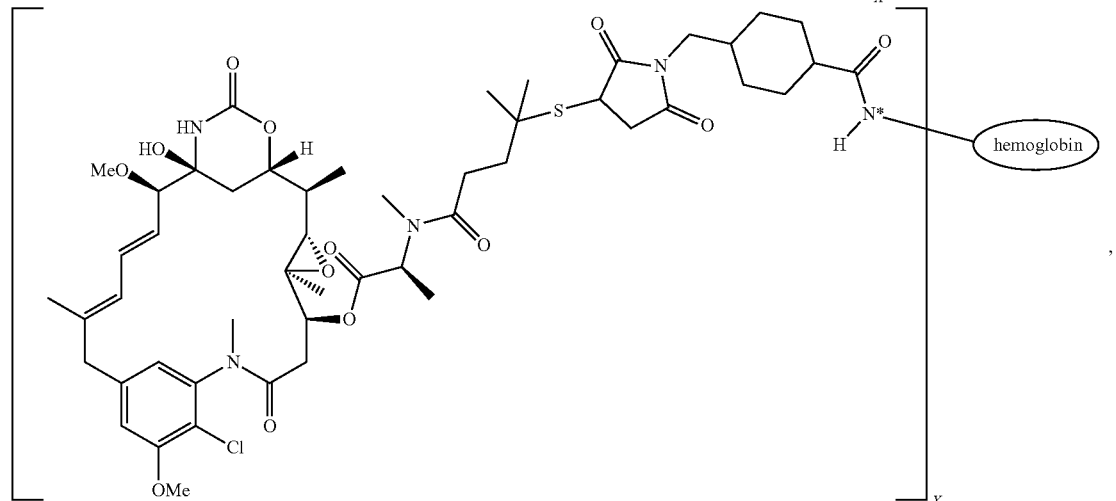
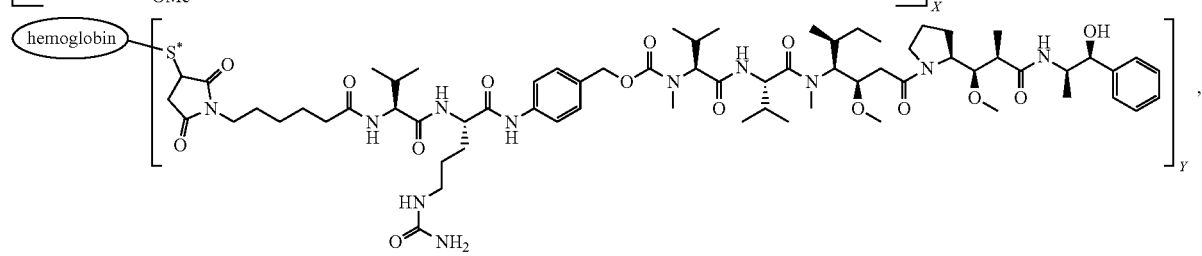

wherein each N* independently represents a nitrogen in a lysine side chain in the hemoglobin or a N-terminal amine in the hemoglobin;

S* independently represents a sulfur in a cysteine side chain in the hemoglobin;

X is the MDR of the hemoglobin-based therapeutic agent, wherein X has a value between 1.0-5.0; and Y is the MDR of the hemoglobin-based therapeutic agent, wherein Y has a value between 1.0-2.0.

9. The hemoglobin-based therapeutic agent of claim 1, wherein the hemoglobin-based therapeutic agent has the formula:

13. A method for preparing a hemoglobin-based therapeutic agent of Formula 3:

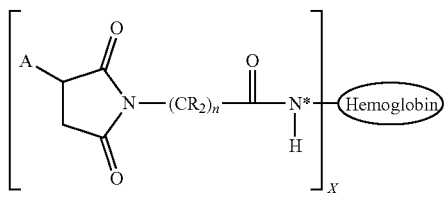

wherein A is DM1 or DM4;

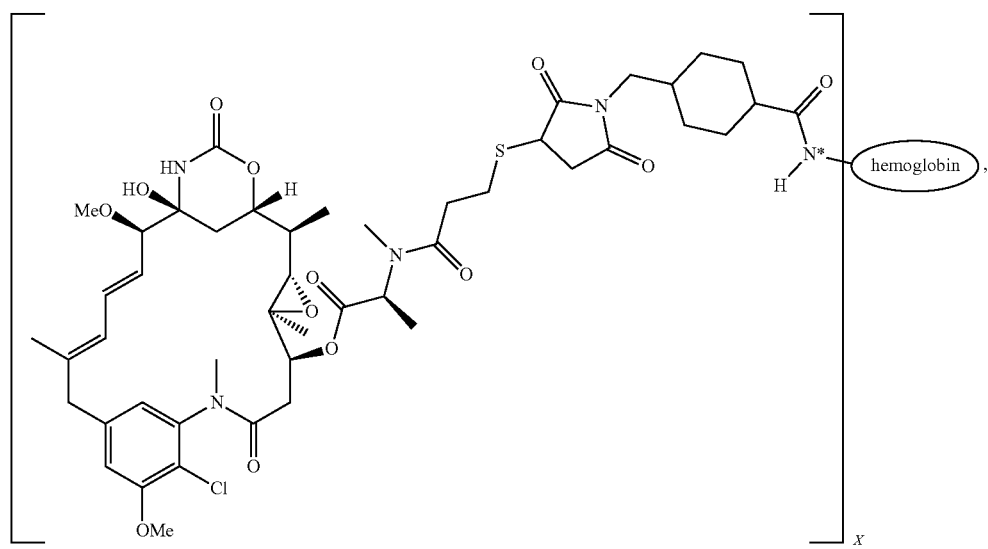

wherein N* independently represents a nitrogen in a lysine side chain in the hemoglobin or a N-terminal amine in the hemoglobin; and X is the MDR of the hemoglobin-based therapeutic agent, wherein X has a value between 2.0-5.0.

10. The hemoglobin-based therapeutic agent of claim 9, wherein X has a value between 2.5-3.5.

11. The hemoglobin-based therapeutic agent of claim 1 further comprising a fluorescent dye.

12. A pharmaceutical composition comprising a hemoglobin-based therapeutic agent of claim 1 and at least one pharmaceutically acceptable carrier.

X is the MDR of the hemoglobin-based therapeutic agent, wherein X has a value between 1.0-5.0;

N* independently represents a nitrogen in a lysine side chain in the hemoglobin or a N-terminal amine in the hemoglobin;

n is a whole number selected from 1-10; and each R is hydrogen; or two R taken together with the carbons to which they are attached form a 3-7 membered cycloalkane and each remaining R is hydrogen, the method comprising:

contacting a hemoglobin with a compound of Formula 4:

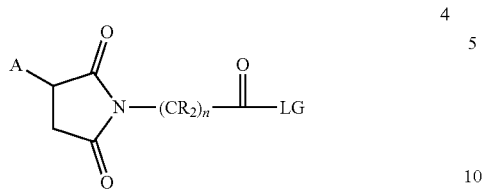

wherein LG is a leaving group, thereby forming the hemoglobin-based therapeutic agent of Formula 3.

14. The method of claim 13, wherein the molar ratio of hemoglobin to the compound of Formula 4 is between 1:4 to 1:6.

15. The method of claim 13, wherein the compound of Formula 4 has the structure:

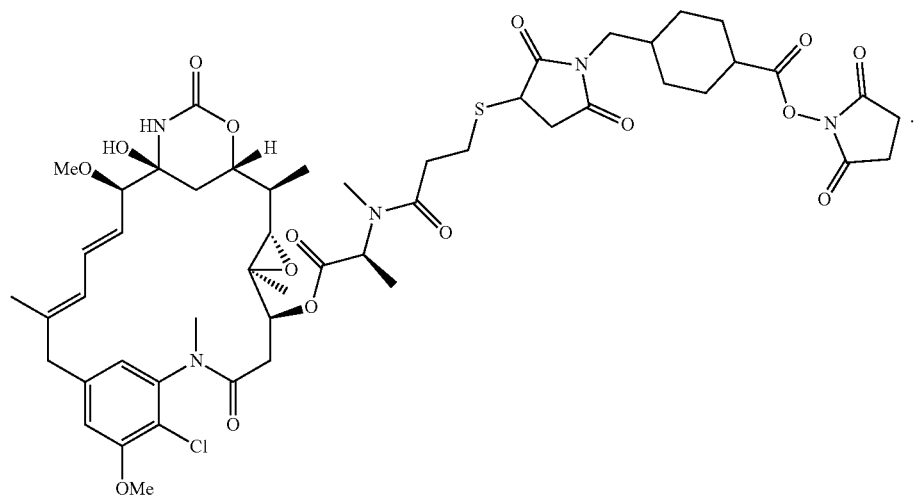 [SMILES: COc1cc2cc(c1Cl)N(C)C(=O)C[C@H](OC(=O)[C@H](C)N(C)C(=O)CCSC1CC(=O)N(CC3CCC(C(=O)ON4C(=O)CCC4=O)CC3)C1=O)[C@]1(C)O[C@H]1[C@H](C)[C@@H]1C[C@@](O)(NC(=O)O1)[C@H](OC)/C=C/C=C(\C)C2]

16. A method of treating cancer in a subject in need thereof, the method comprising administering a therapeutically effective amount of a hemoglobin-based therapeutic agent of claim 1 to the subject.

17. The method of claim 16, wherein the cancer is selected from the group consisting of pancreatic cancer, leukemia, head and neck cancer, colorectal cancer, lung cancer, breast cancer, liver cancer, nasopharyngeal cancer, esophageal cancer, lymphoma, melanoma, and brain cancer.

18. The method of claim 16, wherein said cancer is hepatocellular carcinoma, liver cancer progenitor cells-induced tumor, glioblastoma, or triple negative progenitor cells-induced tumor.

19. The method of claim 16, wherein the hemoglobin-based therapeutic agent is administered intravenously, intraperitoneally, or subcutaneously.

* * * * *

SEQUENCE LISTING

```
<160> NUMBER OF SEQ ID NOS: 2

<210> SEQ ID NO 1
<211> LENGTH: 283
<212> TYPE: PRT
<213> ORGANISM: Artificial Sequence
<220> FEATURE:
<223> OTHER INFORMATION: di-alpha chain, synthesized in lab

<400> SEQUENCE: 1

Met Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Phe Glu Arg Met
            20                  25                  30

Phe Leu Ser Phe Pro Thr Thr Lys Thr Tyr Phe Pro His Phe Asp Leu
        35                  40                  45

Ser His Gly Ser Ala Gln Val Lys Gly Gln Gly Lys Lys Val Ala Asp
    50                  55                  60

Ala Leu Thr Asn Ala Val Ala His Val Asp Asp Met Pro Asn Ala Leu
65                  70                  75                  80

Ser Ala Leu Ser Asp Leu His Ala His Lys Leu Arg Val Asp Pro Val
                85                  90                  95
```

```
Asn Phe Lys Leu Leu Ser His Cys Leu Leu Val Thr Leu Ala Ala His
                100                 105                 110
Leu Pro Ala Glu Phe Thr Pro Ala Val His Ala Ser Leu Asp Lys Phe
            115                 120                 125
Leu Ala Ser Val Ser Thr Val Leu Thr Ser Lys Tyr Arg Gly Met Leu
        130                 135                 140
Ser Pro Ala Asp Lys Thr Asn Val Lys Ala Ala Trp Gly Lys Val Gly
145                 150                 155                 160
Ala His Ala Gly Glu Tyr Gly Ala Glu Ala Phe Glu Arg Met Phe Leu
                165                 170                 175
Ser Phe Pro Thr Thr Lys Thr Tyr Phe Pro His Phe Asp Leu Ser His
            180                 185                 190
Gly Ser Ala Gln Val Lys Gly Gln Gly Lys Lys Val Ala Asp Ala Leu
        195                 200                 205
Thr Asn Ala Val Ala His Val Asp Asp Met Pro Asn Ala Leu Ser Ala
210                 215                 220
Leu Ser Asp Leu His Ala His Lys Leu Arg Val Asp Pro Val Asn Phe
225                 230                 235                 240
Lys Leu Leu Ser His Cys Leu Leu Val Thr Leu Ala Ala His Leu Pro
                245                 250                 255
Ala Glu Phe Thr Pro Ala Val His Ala Ser Leu Asp Lys Phe Leu Ala
            260                 265                 270
Ser Val Ser Thr Val Leu Thr Ser Lys Tyr Arg
        275                 280

<210> SEQ ID NO 2
<211> LENGTH: 146
<212> TYPE: PRT
<213> ORGANISM: Artificial Sequence
<220> FEATURE:
<223> OTHER INFORMATION: beta chain, synthesized in lab

<400> SEQUENCE: 2

Met His Leu Thr Pro Glu Glu Lys Ser Ala Val Thr Ala Leu Trp Gly
1               5                   10                  15
Lys Val Asn Val Asp Glu Val Gly Gly Glu Ala Leu Gly Arg Leu Leu
                20                  25                  30
Val Val Tyr Pro Trp Thr Gln Arg Phe Phe Glu Ser Phe Gly Asp Leu
            35                  40                  45
Ser Thr Pro Asp Ala Val Met Gly Asn Pro Lys Val Lys Ala His Gly
50                  55                  60
Lys Lys Val Leu Gly Ala Phe Ser Asp Gly Leu Ala His Leu Asp Asn
65                  70                  75                  80
Leu Lys Gly Thr Phe Ala Thr Leu Ser Glu Leu His Cys Asp Lys Leu
                85                  90                  95
His Val Asp Pro Glu Asn Phe Arg Leu Leu Gly Asn Val Leu Val Cys
                100                 105                 110
Val Leu Ala His His Phe Gly Lys Glu Phe Thr Pro Pro Val Gln Ala
            115                 120                 125
Ala Tyr Gln Lys Val Val Ala Gly Val Ala Asn Ala Leu Ala His Lys
        130                 135                 140
Tyr His
145
```